US009181305B2

(12) United States Patent
Haack et al.

(10) Patent No.: US 9,181,305 B2
(45) Date of Patent: Nov. 10, 2015

(54) EXENDIN-4 PEPTIDE ANALOGUES

(71) Applicant: SANOFI, Paris (FR)

(72) Inventors: Torsten Haack, Frankfurt am Main (DE); Andreas Evers, Frankfurt am Main (DE); Michael Wagner, Frankfurt am Main (DE); Bernd Henkel, Frankfurt am Main (DE); Siegfried Stengelin, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 13/916,757

(22) Filed: Jun. 13, 2013

(65) Prior Publication Data
US 2013/0336893 A1 Dec. 19, 2013

(30) Foreign Application Priority Data

Jun. 14, 2012 (EP) ..................................... 12172010

(51) Int. Cl.
| C07K 14/62 | (2006.01) |
| C07K 14/00 | (2006.01) |
| A61K 38/16 | (2006.01) |
| A61K 38/26 | (2006.01) |
| A61K 38/28 | (2006.01) |
| A61K 45/06 | (2006.01) |
| C07K 14/605 | (2006.01) |
| A61K 38/22 | (2006.01) |

(52) U.S. Cl.
CPC .................. C07K 14/00 (2013.01); A61K 38/16 (2013.01); A61K 38/22 (2013.01); A61K 38/26 (2013.01); A61K 38/28 (2013.01); A61K 45/06 (2013.01); C07K 14/605 (2013.01)

(58) Field of Classification Search
None
See application file for complete search history.

(56) References Cited

U.S. PATENT DOCUMENTS

| 5,424,286 | A | 6/1995 | Eng |
| 6,858,576 | B1 | 2/2005 | Young et al. |
| 2009/0098130 | A1* | 4/2009 | Bradshaw et al. ......... 424/139.1 |
| 2009/0298757 | A1* | 12/2009 | Bloom et al. .................... 514/12 |
| 2011/0237503 | A1 | 9/2011 | Alsina-Fernandez et al. |
| 2012/0148586 | A1 | 6/2012 | Chou et al. |

FOREIGN PATENT DOCUMENTS

| WO | WO 2004/035623 A2 | 4/2004 |
| WO | WO 2006/134340 A2 | 12/2006 |
| WO | 2007139941 A2 | 12/2007 |
| WO | 2008023050 A1 | 2/2008 |
| WO | 2008071972 A1 | 6/2008 |
| WO | 2008081418 A1 | 7/2008 |
| WO | 2008101017 A2 | 8/2008 |
| WO | 2008152403 A1 | 12/2008 |
| WO | 2009155258 A2 | 12/2009 |
| WO | 2010070251 A1 | 6/2010 |
| WO | 2010070252 A1 | 6/2010 |
| WO | 2010070253 A1 | 6/2010 |
| WO | 2010070255 A1 | 6/2010 |
| WO | 2010096052 A1 | 8/2010 |
| WO | 2010096142 A1 | 8/2010 |
| WO | 2011006497 A1 | 1/2011 |
| WO | 2011075393 A1 | 6/2011 |
| WO | 2011094337 A1 | 8/2011 |
| WO | 2011117415 A1 | 9/2011 |
| WO | 2011117416 A1 | 9/2011 |
| WO | 2011152181 A1 | 12/2011 |
| WO | 2011152182 A1 | 12/2011 |
| WO | 2011160630 A2 | 12/2011 |

OTHER PUBLICATIONS

Byetta product information, accessed Feb. 9, 2014 at http://www.accessdata.fda.gov/drugsatfda_docs/label/2008/021773s012lbl.pdf.*
Braga et al., "Making Crystals from Crystals: a green route to crystal engineering and polymorphism," Chem. Commun., 2005, pp. 3635-3645.*
Seddon, K.R., "Pseudopolymorph: a polemic," Crystal Growth & Design, 2004, 4(6), pp. 1087, web release date Oct. 19, 2004.*
Vippagunta et al. "Crystalline Solids," Advanced Drug Delivery Reviews, 2001, 48, pp. 3-26.*
Siv A. Hjorth, et al., Glucagon and Glucagon-like Peptide 1: Selective Receptor Recognition via Distinct Peptide Epitopes, The Journal of Biological Chemistry, (Dec. 2, 1994), vol. 269, No. 48, pp. 30121-30124.
Brian L. Furman, The development of Byetta (exenatide) from the venom of the Gilo monster as an anti-diabetic agent, Toxicon, (Mar. 15, 2012), vol. 59, pp. 464-471.
European Search Report dated Apr. 19, 2013 issued in EP 12 17 2010.
Krstenansky, J.L. et al., Importance of the 10-13 Region of Glucagon for Its Receptor Interaction and Activation of Adenylate Cyclase, Biochemistry, (1986), vol. 25, No. 13, pp. 3833-3839.
Bunck, M.G. et al. 'Effects of Exenatide on MEasures of B-Cell Function After 3 Years in Metformin-Treated Patients With Type 2 Diabetes'. Diabetes Care. 2011, vol. 34, pp. 2041-2047.
Buse, J.B. et al. 'Liraglutide once a day versus exenatide twice a day for type 2 diabetes: a 26-week randomised, parallel group, multinational, open-label trial (LEAD-6)'. The Lacenet. 2009, vol. 374, pp. 39-47.
Chhabra et al. 'An Appraisal of New Variants of Dde Amine Protecting Group for Solid Phase Peptide Synthesis'. Tetrahedron Letters. 1998, vol. 39, pp. 1603-1606.
Drucker et al. 'Liraglutide'. New Reviews—Drug Discovery. 2010, vol. 9, No. 4, pp. 267-268.
Eng et al. 'Isolation and Characterization of Exendin-4, an Exendin-3 Analogue, from Heloderma Suspectum Venom'. The Journal of Biological Chemistry. 1992, vol. 267, No. 11, pp. 7402-7405.
Eng et al. 'Prolonged Effect of Exendin-4 on Hyperglycemia of db/db Mice'. Diabetes. 1996, vol. 45, pp. 152A, Abstract 554.
Gentilella et al. 'Exenatide: A Review from Pharmacology to Clinical Practice'. Diabetes, Obesity, and Metabolism. 2009, vol. 11, pp. 544-556.

(Continued)

Primary Examiner — Julie Ha
Assistant Examiner — Kristina M Hellman
(74) Attorney, Agent, or Firm — Lathrop & Gage LLP; James H. Velema, Esq.

(57) ABSTRACT

The present invention relates to exendin-4 peptide analogs and their medical use, for example in the treatment of disorders of the metabolic syndrome, including diabetes and obesity, as well as reduction of excess food intake.

44 Claims, 4 Drawing Sheets

(56) References Cited

OTHER PUBLICATIONS

Hargrove et al. 'Biological Activity of AC3174, A Peptide Analog of Exendin-4'. Regulatory Peptides. 2007, vol. 141, pp. 113-119.

King et al. 'A Cleavage Method which Minimizes Side Reactions Following Fmoc Solid Phase Peptide Synthesis'. International Journal of Peptide Protein Research. 1990, vol. 36, pp. 255-266.

Norris et al. 'Exenatide Efficacy and Safety: A Systematic Review'. Diabetic Medicine. 2009, vol. 26, pp. 837-846.

Day et al. 'A New Glucagon and GLP-1 co-agonist Eliminates Obesity in Rodents'. Nature Chemical Biology. 2009, vol. 5, No. 10, pp. 749-757.

Ficht et al. 'Solid-phase Synthesis of Peptide and Glycopeptide Thioesters through Side-Chain-Anchoring Strategies'. Chem. Eur. J. 2008, vol. 14, pp. 3620-3629.

Chae et al. 'The fatty acid conjugated exendin-4 analogs for type 2 antidiabetic therapeutics'. Journal of Controlled Release. 2010, vol. 144, pp. 10-16.

European Search Report dated Apr. 19, 2013 issued in EP 12306232.

European Search Report dated Jul. 15, 2013 issued in EP 13505222.

European Search Report from EP Application EP12306647.4, dated May 22, 2013.

Office Action in related U.S. Appl. No. 14/049,597, filed Oct. 9, 2013, mailed Aug. 29, 2014.

International Preliminary Report on Patentability for application No. PCT/EP2013/062090, dated Nov. 24, 2014 (20 pages).

\* cited by examiner

EXENDIN-4 PEPTIDE ANALOGUES

FIELD OF THE INVENTION

The present invention relates to exendin-4 peptide analogues and their medical use, for example in the treatment of disorders of the metabolic syndrome, including diabetes and obesity, as well as reduction of excess food intake.

BACKGROUND OF THE INVENTION

Exendin-4 is a 39 amino acid peptide which is produced by the salivary glands of the Gila monster (*Heloderma suspectum*) (Eng, J. et al., J. Biol. Chem., 265: 20259-62,1990; Ng, J. et al., J. Biol. Chem., 267:7402-05, 1992). Like GLP-1, exendin-4 is an activator of the GLP-1 receptor. Unlike GLP-1, exendin-4 has a prolonged glucose-lowering action in vivo (Eng J., Diabetes, 45(Suppl 2):152A (abstract 554), 1996).

The amino acid sequence of exendin-4 is shown as SEQ ID NO: 1:

```
HGEGTFTSDLSKQMEEEAVRLFIEWLKNGGPSSGAPPPS-NH2
```

The amino acid sequence of GLP-1 is shown as SEQ ID NO: 2:

```
HAEGTFTSDVSSYLEGQAAKEFIAWLVKGR
```

Its actions include stimulation of insulin synthesis and secretion, inhibition of glucagon secretion, and inhibition of food intake. GLP-1 has been shown to reduce hyperglycemia in diabetics.

There is also evidence that GLP-1 and exendin-4 may reduce food intake and promote weight loss (Buse J. B. et al., Lancet, 374:39-47, 2009). This effect would be beneficial not only for diabetics but also for patients suffering from obesity. Such patients with obesity have a higher risk of diabetes, hypertension, hyperlipidemia, cardiovascular disease, and musculoskeletal diseases.

Glucagon is a 29-amino acid peptide which is released into the bloodstream when circulating glucose is low. Glucagon has the amino acid sequence as shown in SEQ ID NO: 3:

```
HSQGTFTSDYSKYLDSRRAQDFVQWLMNT
```

During hypoglycemia, when blood glucose levels drop below normal, glucagon signals the liver to break down glycogen and release glucose, causing blood glucose levels to rise towards a normal level. Hypoglycemia is a common side effect of insulin therapy in patients with hyperglycemia (elevated blood glucose levels) due to diabetes. Thus, glucagon's most recognized role in glucose regulation is to counteract the action of insulin and maintain blood glucose levels.

Other peptides which bind and activate both the glucagon and the GLP-1 receptor (Hjort et al. Journal of Biological Chemistry, 269, 30121-30124, 1994) and suppress body weight gain and reduce food intake are described in WO 2011/075393, WO 2011/006497, WO 2011/152181, and WO 2011/152182, the contents of which are herein incorporated by reference.

The use of exendin-4 agonists has been proposed for the treatment of diabetes mellitus, reduce of gastric motility, delay of gastric emptying and the prevention of hyperglycemia (U.S. Pat. No. 5,424,286, U.S. Pat. No. 6,858,576, WO98/05351). The use of exendin-4 agonists for reducing food intake is described in WO98/30231, the contents of which are herein incorporated by reference.

Exendin-4 analogues have been described in WO99/43708, WO9/035540, the contents of which are herein incorporated by reference.

BRIEF SUMMARY OF THE INVENTION

The invention provides a peptidic compound having the formula (I):

$$R1-Z-R2 \quad\quad\quad (I)$$

wherein Z is a peptide moiety having the formula (II)

$$X0m\text{-}X1\text{-}X2\text{-}X3\text{-}Gly\text{-}Thr\text{-}Phe\text{-}Thr\text{-}Ser\text{-}Asp\text{-}Leu\text{-}Ser\text{-}$$
$$Lys\text{-}Gln\text{-}X14\text{-}X15\text{-}X16\text{-}X17\text{-}X18\text{-}X19\text{-}X20\text{-}X21\text{-}$$
$$Phe\text{-}Ile\text{-}Glu\text{-}Trp\text{-}Leu\text{-}Lys\text{-}X28\text{-}X29\text{-}Gly\text{-}Pro\text{-}Ser\text{-}$$
$$Ser\text{-}Gly\text{-}X35\text{-}Pro\text{-}Pro\text{-}Pro\text{-}X39\text{-}X40n \quad\quad (II)$$

X0 is absent or represents an amino acid residue selected from Gly,

X1 represents an amino acid residue selected from His, D-His, and Des-amino-His, X2 represents an amino acid residue selected from Gly, Ser or functionalized-Ser, e.g. Ser (OCH3), D-Ser or functionalized D-Ser, e.g. D-Ser (OCH3), Aib, Ala, or D-Ala, wherein Ser may be functionalized in that the H of the OH side chain group is substituted by C1-4 alkyl, e.g. methyl, X3 represents an amino acid residue selected from Glu, Gln, His and α-amino-functionalized Gln, e.g. Gln (α-NHCH3), wherein Gln may be functionalized in that an H of the α-NH2 group is substituted by C1-4 alkyl, e.g. methyl, X14 represents an amino acid residue selected from Met, Phe, Aib, Nle, or Cycloalkyl-Ala, e.g. Cyclohexyl (Chx)-Ala, Cyclopentyl (Cp)-Ala or Cyclobutyl (Cb)-Ala, wherein Ala may be functionalized in that one H of the CH3 side chain group is substituted by C3-8 cycloalkyl, X15 represents an amino acid residue selected from Glu or Asp, X16 represents an amino acid residue selected from Ser, Glu and Lys, X17 represents an amino acid residue selected from Arg, Glu, Gln, Aib and Lys, X18 represents an amino acid residue selected from Arg, Ala and Lys, X19 represents an amino acid residue selected from Ala and Val, X20 represents an amino acid residue selected from Gln, Arg, Lys, His and Aib, X21 represents an amino acid residue selected from Asp, Leu and Glu, X28 represents an amino acid residue selected from Asn, Arg, Lys, Aib, Ser, Glu and Ala, X29 represents an amino acid residue selected from Gly, Ala, D-Ala or Thr, and X35 represents an amino acid residue selected from Ala, Glu, Arg and Lys, X39 represents an amino acid residue selected from Ser, an amino acid residue having a side chain with an —NH2 group, particularly Lys, Orn, Dab or Dap, wherein the —NH2 side chain group is optionally functionalized and an amino acid residue having a side chain with an —SH group, particularly Cys, wherein the —SH side chain group is optionally functionalized, and X40 represents an amino acid residue selected from an amino acid residue having a side chain with an —NH2 group, particularly Lys, Orn, Dab or Dap, wherein the —NH2 side chain group is optionally functionalized and an amino acid residue having a side chain with an —SH group, particularly Cys, wherein the —SH side chain group is optionally functionalized, R1 represents the N-terminal group of the peptidic compound and is selected from NH2 or mono- or bisfunctionalized NH2, R2 represents the C-terminal group of the peptidic compound and is selected from (i) OH or functionalized OH and (ii) NH2 or mono- or bisfunctionalized NH2, m and n are in each case independently selected from 0 or 1 or a salt or solvate thereof with the proviso that Exendin-4 (SEQ ID NO: 1) is not encompassed.

The compounds of the invention are typically GLP-1 and/or glucagon receptor agonists, preferably dual GLP-1 and glucagon receptor agonists as determined by the observation that they are capable of stimulating intracellular cAMP formation upon binding at least one of the receptors for GLP-1, as well as glucagon. The compounds may e.g. exhibit an EC50 value (determined by an in vitro cellular assay as described in the Examples) for the GLP1 receptor, which is less than 5 nM, preferably less than 1 nM, more preferably less than 500 pM and even more preferably of less than 200 pM. Further, the compounds may exhibit an EC50 value (as determined according to the Examples) for the glucagon receptor which is less than 5 nM, preferably less than 1 nM, more preferably less than 500 pM and even more preferably less than 200 pM. Furthermore, the compounds may exhibit an EC50 value for the GLP1 receptor and an EC50 value for the glucagon receptor, which is less than 5 nM, preferably less than 1 nM, more preferably less than 500 pM, and even more preferably less than 200 pM.

Further, the compounds of the invention preferably have a high solubility at pH 4.5 and/or at pH 7.4 at 25° C. (determined as described in the Examples), preferably at least 0.5 mg/ml and more preferably at least 1.0 mg/ml.

Furthermore, the compounds of the invention preferably have a high stability when stored for 7 days at 25° C. (determined by chromatographic analyses as described in the Examples), preferably a remaining peptide amount of at least 80%, more preferably of at least 85%, even more preferably at least 90% and even more preferably of at least 95%.

Preferably, the compounds of the present invention comprise a peptide moiety Z (II) which is a linear sequence of 39-41 amino carboxylic acids, particularly α-amino carboxylic acids linked by peptide, i.e. carboxamide bonds.

The peptide moiety Z has variable positions X0, X1, X2, X3, X14, X15, X16, X17, X18, X19, X20, X21, X28, X29, X35, X39 and X40, which in each case independently represent an amino acid residue as described above, with the proviso that X0 and/or X40 may be absent. The amino acid residue at the variable positions is preferably an α-amino carboxylic acid residue having a side chain which may be non-functionalized or functionalized. The amino acid residues at non-variable positions are amino carboxylic acids, particularly L-amino carboxylic acids with a side chain corresponding to the indicated meaning in formula (II).

At least one amino acid residue at the variable positions differs from the corresponding amino acid residue in Exendin-4 (SEQ ID NO. 1). The difference may constitute the presence of a different side chain, e.g. Ser or functionalized Ser instead of Gly or the presence of a functionalized side chain instead of a non-functionalized side chain, e.g. N-functionalized Lys instead of Lys.

R1 represents the N-terminal group and is selected from NH2 or mono- or bisfunctionalized NH2. The term "mono- or bisfunctionalized NH2" for R1 means that at least one H of the NH2 group is substituted by a different moiety, e.g. an organic moiety of up to 20 or up to 30 carbon atoms and optionally comprising heteroatoms, such as halo (F, Cl, Br, or I), N, O, S and/or P, or an organic polymer, particularly a hydrophilic organic polymer. Preferred polymers are (poly) alkylene oxide-based polymers comprising up to 2000 alkylene oxide groups, particularly (poly)ethylene oxide-based polymers. Examples of functional groups for R1 are alkyl, formyl, (poly)alkoxyalkyl, —C(O)-alkyl or —C(O)-(poly) alkoxyalkyl, wherein each alkoxy or alkyl may comprise 1-12, preferably 1-8, and more preferably 1-5 C-atoms, and may be substituted by halo and/or OH, and wherein a (poly) alkoxyalkyl group may comprise up to 2000 alkylene oxide groups, particularly $CH_2$-$CH_2$-O groups. Specific examples of functional groups are methyl, ethyl, formyl, acetyl, trifluoroacetyl or benzoyl.

R2 represents the C-terminal group of the peptidic compound and is selected from OH or functionalized OH and NH2 or mono- or bisfunctionalized NH2. The terms "functionalized OH" and "mono- or bisfunctionalized NH2" for R2 mean that the H of the OH group is substituted by a different moiety, e.g. an organic moiety or that at least one H of the NH2 group is substituted by a different moiety, e.g. an organic moiety, e.g. an organic moiety of up to 30 or up to 40 carbon atoms and optionally comprising heteroatoms, such as halo (F, Cl, Br, or I), N, O, S and/or P, or an organic polymer, particularly a hydrophilic organic polymer. Preferred polymers are (poly)alkylene oxide-based polymers comprising up to 2000 alkylene oxide groups, particularly (poly)ethylene oxide-based polymers. Examples of functional groups for R2 are moieties of the formula R3-R4, wherein R3 is alkylene or (poly)alkoxy-alkylene, wherein each alkoxy or alkylene may comprise 1-12, preferably 1-8 and more preferably 1-5 C-atoms and may be substituted by halo, and/or OH, wherein a (poly)alkoxy-alkylene may comprise up to 2000 alkylene oxide groups, particularly CH2-CH2-O groups, and R4 is H, NH2, NH(C1-4 alkyl), N(C1-C4 alkyl), N(C1-4 alkyl)2, OH, O(C1-4 alkyl), SH, S(C1-4 alkyl). Alternatively, an amino group may also be functionalized by OH or NH2. Specific examples of functional groups are 2-mercapto-ethyl, 2-tert-butyl sulfanyl-ethyl, 5-hydroxy-pentyl, 4-amino-butyl, 5-amino-pentyl, or 3-{2-[2-(5-amino-pentyloxy)-ethoxy]-ethoxy}-propyl.

In an embodiment, the N-terminal group R1 is NH2. In a further embodiment, the C-terminal group R2 is NH2. In still a further embodiment the N-terminal group R1 and the C-terminal group R2 are NH2.

In a further embodiment 1, 2 or 3 amino acids residues selected from X2, X3, X19 are amino acid residues which differ from corresponding amino acid residues in Exendin-4 (SEQ ID NO: 1).

In a still further embodiment, at least 2, 3, 4, 5, 6, 7, 8, 9, 10, 11 or 12 amino acid residues selected from X1, X2, X3, X14, X15, X16, X17, X18, X19, X20, X21, X28, X29, X35 and X39 are amino acid residues which differ from corresponding amino acid residues in Exendin-4 (SEQ ID NO: 1).

For example, 3, 4, 5, 6, 7, 8, 9, 10, 11 or 12 amino acid residues selected from X1, X2, X3, X14, X15, X16, X17, X18, X19, X20, X21, X28, X29, X35 and X39 may be amino acid residues which differ from the corresponding amino acid residues in Exendin-4 (SEQ ID NO: 1).

In an embodiment of the invention X0 is absent. In a further embodiment, X40 is absent. In still a further embodiment, X0 is absent and X40 is present. In a still further embodiment, X0 is present and X40 is absent. In still a further embodiment, X0 is present and X40 is present.

If X40 is absent, X39 preferably represents Ser or an amino acid residue with a non-functionalized or functionalized —NH2 side chain group, such as Lys or functionalized Lys, Orn, functionalized Orn, Dab, functionalized Dab, Dap, or functionalized Dap, more preferably Lys or functionalized Lys and even more preferably functionalized Lys.

If X40 is present, X39 preferably represents Ser. If X40 is present, it preferably represents an amino acid residue with a non-functionalized or functionalized —NH2 side chain group or an amino acid residue with a functionalized —SH side chain group, such as Lys or functionalized Lys, Orn, functionalized Orn, Dab, functionalized Dab, Dap, functionalized Dap, or functionalized Cys, more preferably Lys or functionalized Lys and even more preferably functionalized Lys.

An amino acid residue with an —NH2 side chain group, e.g. Lys, Orn, Dab or Dap, may be functionalized in that at least one H atom of the —NH2 side chain group is replaced by —C(O)—R5, —S(O)$_2$—R5 or R5, preferably by —C(O)—R5, wherein R5 may be (i) a moiety comprising up to 50 or up to 100 carbon atoms and optionally heteroatoms selected from halo, N, O, S and/or P, and/or (ii) an organic polymer, particularly a hydrophilic organic polymer. Preferred groups R5 may be comprise a lipophilic moiety, e.g. an acyclic linear or branched C12-30 saturated or unsaturated hydrocarbon group, and/or a cyclic saturated, unsaturated or aromatic group, e.g. cyclohexyl, phenyl, biphenyl, chromanyl, phenanthrenyl or naphthyl, wherein the acyclic or cyclic group may be unsubstituted or substituted e.g. by halo, —OH and/or CO2H. The lipophilic moiety may be attached to the —NH2 side chain group by a linker, e.g. a linker comprising one or more, e.g. 2 amino acid linker groups such as γ-aminobutyric acid (γ-Abt), ϵ-aminohexanoic acid (ϵ-Ahx), γ-Glu and/or β-Ala. Specific examples of amino acid linker groups are (β-Ala)1-4, (γ-Glu)1-4, (ϵ-Ahx)1-4, or (γ-Abt)1-4. Still further preferred groups R5 may comprise a C1-4 acyl group, e.g. acetyl. Still further preferred groups R5 may comprise at least one amino acid residue, e.g. γ-Abt, ϵ-Ahx, γ-Glu and/or β-Ala. Preferred polymers are (poly)alkylene oxide-based polymers, particularly (poly)ethylene oxide-based polymers, e.g. polymers comprising a (CH2-CH2-O)q-R6 group, wherein q is 1-2000 and R6 is H or C1-4 alkyl. Examples are (poly)ethylenglycols having an average weight-based molecular mass from about 1000 up to about 100,000 Da, e.g. about 2000, about 5000, about 20,000, about 40,000 or about 80,000 Da.

An amino acid residue with an —SH side chain, e.g. Cys may be functionalized in that the H atom of the —SH side chain group is replaced by —Y—R7, wherein Y is a bond or a thiol linker group, e.g. a maleimide or acetamide group or thiol and R7 represents a group as defined for R5 above. Preferably R7 is an organic polymer, particularly a (poly) ethyleneoxide-based polymer as defined above.

Specific preferred examples for —C(O)—R5 groups are listed in the following Table 1. Further preferred are stereoisomers, particularly enantiomers of these groups, either S- or R-enantiomers. The term "R" in Table 1 is intended to mean the attachment site of —C(O)—R5 at the peptide back bone, i.e. particularly the ϵ-amino group of Lys.

TABLE 1

| CHEMISTRY | IUPAC name | alternative name |
|---|---|---|
| | (S)-4-Carboxy-4-hexadecanoylamino-butyryl- | γ-Glu(N-α-hexadecanoyl) |
| | (S)-4-Carboxy-4-octadecanoylamino-butyryl- | γ-Glu(N-α-octadecanoyl) |
| | octadecanoyl- | N-α-octadecanoyl |
| | Hexadecanoyl- | N-α-hexadecanoyl |
| | (S)-4-Carboxy-4-{3-[(R)-2,5,7,8-tetramethyl-2-((4R,8R)-4,8,12-trimethyl-tridecyl)-chroman-6-yloxycarbonyl]-propionylamino}-butyryl- | γ-Glu(N-α-tocopherylsuccinyl) |
| | (S)-4-Carboxy-4-(15-carboxy-pentadecanoylamino)-butyryl- | γ-Glu(N-α-(ω-carboxy-pentadecanoyl)) |

TABLE 1-continued

| CHEMISTRY | IUPAC name | alternative name |
|---|---|---|
| | (S)-4-Carboxy-4-((S)-4-carboxy-4-hexadecanoylamino-butyrylamino)-butyryl- | γ-Glu(N-α-(γ-Glu(N-α-hexadecanoyl))) |
| | (S)-4-Carboxy-4-octadecanoylamino-butyryl- | |
| | 3-(3-Hexadecanoylamino-propionyla-mino)-propionyl- | β-Ala(N-α-(β-Ala(N-α-hexadecanoyl))) |
| | 3-Hexadecanoylamino-propionyl- | β-Ala(N-α-hexadecanoyl) |
| | 6-[(4,4-Diphenyl-cyclohexyloxy)-hydroxy-phosphoryloxy]-hexanoyl- | |

TABLE 1-continued

| CHEMISTRY | IUPAC name | alternative name |
|---|---|---|
| (structure) | (S)-4-Carboxy-4-[(R)-4-((3R,5S,7R,8R,9R,10S,12S,13R,14R,17R)-3,7,12-trihydroxy-8,10,13-trimethyl-hexadecahydro-cyclopenta[a]phenanthren-17-yl)-pentanoylamino]-butyryl- | γ-Glu(N-α-cholyl) |
| (structure) | (S)-4-Carboxy-4-[(R)-4-((3R,5R,8R,9S,10S,13R,14S,17R)-3-hydroxy-10,13-dimethyl-hexadecahydro-cyclopenta[a]phenanthren-17-yl)-pentanoylamino]-butyryl- | γ-Glu(N-α-lithocholyl) |
| (structure) | (S)-4-Carboxy-4-((9S,10R)-9,10,16-trihydroxy-hexadecanoylamino)-butyryl- | γ-Glu(N-α-aleuritolyl) |
| (structure) | (S)-4-Carboxy-4-{3-[(R)-2,5,7,8-tetramethyl-2-((4R,8R)-4,8,12-trimethyl-tridecyl)-chroman-6-yloxycarbonyl]-propionylamino}-butyryl- | γ-Glu(N-α-tocopheryl-succinyl) |

TABLE 1-continued

| CHEMISTRY | IUPAC name | alternative name |
|---|---|---|
| | (S)-4-Carboxy-4-((9Z,12Z)-octadeca-9,12-dienoylamino)-butyryl- | γ-Glu(N-α-linoleoyl) |
| | (S)-4-Carboxy-4-(4-dodecyloxy-benzoylamino)-butyryl- | γ-Glu(N-α-(4-dodecyclo-benzoyl)) |
| | (S)-4-Carboxy-4-henicosanoylamino-butyryl- | γ-Glu(N-α-heneicosanoyl) |
| | (S)-4-Carboxy-4-docosanoylamino-butyryl- | γ-Glu(N-α-behenoyl) |

TABLE 1-continued

| CHEMISTRY | IUPAC name | alternative name |
|---|---|---|
| (structure) | (S)-4-Carboxy-4-((Z)-nonadec-10-enoylamino)-butyryl- | γ-Glu(N-α-(cis-1-nonadecanoyl)) |
| (structure) | (S)-4-Carboxy-4-(4-decyloxy-benzoylamino)-butyryl- | γ-Glu(N-α-(4-n-decyloxy-benzoyl)) |
| (structure) | (S)-4-Carboxy-4-[(4'-octyloxy-biphenyl-4-carbonyl)-amino]-butyryl- | γ-Glu(N-α-(4'-octyloxy-biphenyl-4-carbonyl)) |

TABLE 1-continued

| CHEMISTRY | IUPAC name | alternative name |
|---|---|---|
| [structure: phenyl-dodecanoylamino-glutamyl linked to R via amide] | (S)-4-Carboxy-4-(12-phenyl-dodecanoylamino)-butyryl- | γ-Glu(N-α-(12-phenyl-dodecanoyl)) |
| [structure: acetyl-R] | acetyl | acetyl |
| [structure: hexadecanoylamino-butyryl-R] | 4-Hexadecanoylamino-butyryl- | γ-amino-butyroyl(N-γ-hexadecanoyl) |
| [structure: isobutyrylamino-glutamyl-R] | (S)-4-Carboxy-4-isobutyrylamino-butyryl- | γ-Glu(N-α-propionyl) |
| [structure: tetradecanoylamino-glutamyl-R] | (S)-4-Carboxy-4-tetradecanoylamino-butyryl- | γ-Glu(N-α-tetradecanoyl) |
| [structure: tetradecanoyl-R] | tetradecanoyl- | N-α-tetradecanoyl |
| [structure: 11-carboxy-undecanoyl-R] | 11-Carboxy-undecanoyl- | N-α-(ω-carboxy-dodecanoyl) |

TABLE 1-continued

| CHEMISTRY | IUPAC name | alternative name |
|---|---|---|
| [structure] | 11-Benzyloxycarbonyl-undecanoyl | |
| [structure] | (S)-4-Carboxy-4-((S)-4-carboxy-4-tetradecanoylamino-butyrylamino)-butyryl- | γ-Glu(N-α-(γ-Glu(N-α-tetradecanoyl))) |
| [structure] | (S)-4-Carboxy-4-((S)-4-carboxy-4-octadecanoylamino-butyrylamino)-butyryl- | γ-Glu(N-α-(γ-Glu(N-α-octadecanoyl))) |
| [structure] | 3-Aminopropionyl- | β-Ala |
| [structure] | 3-(3-Amino-propionylamino)-propionyl- | β-Ala-β-Ala |
| [structure] | 3-[3-(3-Amino-propionylamino)-propionylamino]-propionyl | β-Ala-β-Ala-β-Ala |

TABLE 1-continued

| CHEMISTRY | IUPAC name | alternative name |
|---|---|---|
| (structure) | 3-{3-[3-(3-Amino-propionylamino)-propionylamino]-propionylamino}-propionyl- | β-Ala-β-Ala-β-Ala-β-Ala |
| (structure) | 3-(3-{[(R)-2,5,7,8-Tetramethyl-2-((4R,8R)-4,8,12-trimethyl-tridecyl)-chroman-6-yloxycarbonyl]-propionylamino}-propionylamino)-propionyl- | β-Ala-β-Ala(N-α-tocopheryl-succinyl)) |
| (structure) | 6-Amino-hexanoyl- | ε-Ahx |
| (structure) | 6-(6-Amino-hexanoylamino)-hexanoyl- | ε-Ahx-ε-Ahx |
| (structure) | (2S,3R,4S,5R)-5-Carboxy-2,3,4,5-tetrahydroxy-pentanoyl | |
| (structure) | 8-Amino-octanoyl | |
| (structure) | 3-{2-[2-(2-Methoxy-ethoxy)-ethoxy]-ethoxy}-propionyl | |

TABLE 1-continued

| CHEMISTRY | IUPAC name | alternative name |
|---|---|---|
| | 3-[2-(2-{2-[2 [2-(2-{2-[2-(2-{2-[2-{2-Methoxy-ethoxy)-ethoxy]-ethoxy}-ethoxy)-ethoxy]-ethoxy}-ethoxy)-ethoxy]-ethoxy}-ethoxy)-ethoxy]propionyl- | |
| | 8-Hexadecanoylamino-octanoyl- | |
| | 6-[Hydroxy-(naphthalen-2-yloxy)-phosphoryloxy]-hexanoyl- | |
| | 6-[Hydroxy-(5-phenyl-pentyloxy)-phosphoryloxy]-hexanoyl- | |
| | 7-[4-(1-Carboxy-ethyl)-phenylcarbamoyl]-heptanoyl- | |

TABLE 1-continued

| CHEMISTRY | IUPAC name | alternative name |
|---|---|---|
| [structure: R-C(=O)-CH2-CH2-C(=O)-NH-SO2-naphthalenyl] | 4-(Naphthalene-2-sulfonylamino)-4-oxo-butyryl- | |
| [structure: R-C(=O)-CH2-CH2-C(=O)-NH-SO2-biphenyl] | 4-(Biphenyl-4-sulfonylamino)-4-oxo-butyryl- | |
| [structure: long chain with diacid, glutamate, PEG linker and R group] | (S)-Carboxy-4-{(S)-4-carboxy-4-[2-(2-{2-[2-{2-[(S)-4-carboxy-4-(17-carboxy-heptadecanoylamino)-butyrylamino]-ethoxy}-ethoxy)-acetylamino]-ethoxy}-ethoxy)-acetylamino]-butyrylamino}-butyryl- | |

TABLE 1-continued

| CHEMISTRY | IUPAC name | alternative name |
|---|---|---|
| | (S)-4-Carboxy-4-[2-(2-{2-[2-(2-{2-[(S)-carboxy-4-(17-carboxy-heptadecanoyl)amino]-butyryl}amino)-ethoxy]-ethoxy}-acetylamino]-ethoxy)-ethoxy}-acetylamino]-butyryl | |
| | (S)-4-Carboxy-2-{(S)-4-carboxy-2-[2-(2-{2-[2-(2-{2-[(S)-4-carboxy-4-(17-carboxy-heptadecanoyl)amino]-butyrylamino}-ethoxy)-acetylamino]-ethoxy}-acetylamino)-butyrylamino]-butyryl | |

TABLE 1-continued

| CHEMISTRY | IUPAC name | alternative name |
|---|---|---|
| | (S)-4-Carboxy-2-[2-(2-(2-{2-[2-{(S)-4-carboxy-4-(17-carboxy-heptadecanoylamino)-butyrylamino]-ethoxy}-ethoxy)-acetylamino]-ethoxy)-acetylamino]-butyryl | |
| | (S)-4-Carboxy-4-[(S)-4-carboxy-4-[2-(2-{2-[(S)-4-carboxy-4-(17-carboxy-heptadecanoylamino)-butyrylamino]-ethoxy}-ethoxy)-acetylamino]-butyrylamino]-butyryl | |
| | (S)-4-Carboxy-4-[2-(2-{2-[(S)-4-carboxy-4-(17-carboxy-heptadecanoylamino)-butyrylamino]-ethoxy}-ethoxy)-acetylamino]-butyryl | |

TABLE 1-continued

| CHEMISTRY | IUPAC name | alternative name |
|---|---|---|
| (structure) | (S)-4-Carboxy-2-{(S)-4-carboxy-2-[2-(2-{2-[(S)-4-carboxy-heptadecanoylamino]-butyrylamino}-ethoxy)-ethoxy]-acetylamino}-butyrylamino]-butyryl | |
| (structure) | (S)-4-Carboxy-2-[2-(2-{2-[(S)-4-carboxy-4-(17-carboxy-heptadecanoylamino)-butyrylamino]-ethoxy}-ethoxy)-acetylamino]-butyryl | |

TABLE 1-continued

| CHEMISTRY | IUPAC name | alternative name |
|---|---|---|
| | 2-(2-{2-[2-(2-{2-[(S)-4-Carboxy-4-(17-carboxy-heptadecanoylamino)-butyrylamino]-ethoxy}-ethoxy)-acetylamino]-ethoxy}-ethoxy)-acetyl- | |
| | 2-(2-{2-[(S)-Carboxy-4-(17-carboxy-heptadecanoylamino)-butyrylamino]-ethoxy}-ethoxy)-acetyl | |
| | (S)-4-Carboxy-4-((S)-4-carboxy-4-((S)-carboxy-4-[(S)-4-carboxy-4-(19-carboxy-nonadecanoylamino)-butyrylamino]-butyrylamino}-butyryl | |

TABLE 1-continued
| CHEMISTRY | IUPAC name | alternative name |
|---|---|---|
| 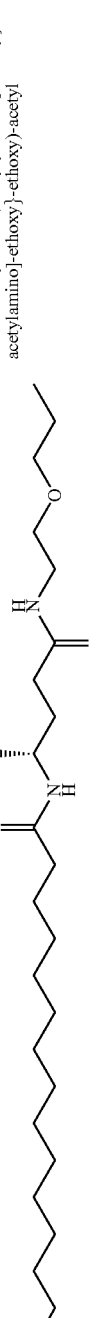 | 2-(2-{2-[2-(2-{2-[(S)-4-Carboxy-4-(16-1H-tetrazol-5-yl-hexadecanoylamino)-butyrylamino]-ethoxy}-ethoxy)-acetylamino]-ethoxy}-ethoxy)-acetyl | |
| 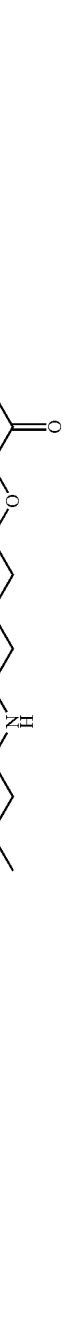 | 2-(2-{2-[2-(2-{2-[(S)-4-Carboxy-4-(16-carboxy-hexadecanoylamino)-butyrylamino]-ethoxy}-ethoxy)-acetylamino]-ethoxy}-ethoxy)-acetyl | |
| 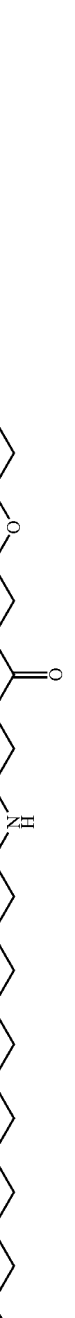 | (S)-4-Carboxy-4-{(S)-4-carboxy-4-(17-carboxy-heptadecanoylamino)-butyrylamino]-butyryl | |

TABLE 1-continued

| CHEMISTRY | IUPAC name | alternative name |
|---|---|---|
| | (S)-4-Carboxy-4-((S)-4-carboxy-4-{2-[2-(2-{2-[2-(2-{(S)-4-carboxy-4-[10-(4-carboxy-phenoxy)-decanoylamino]-butyrylamino}-ethoxy)-ethoxy]-acetylamino}-ethoxy)-ethoxy]-acetylamino}-butyryl | |
| | (S)-4-Carboxy-4-[(S)-4-carboxy-4-(7-carboxy-heptanoylamino)-butyrylamino]-butyryl (2-{2-[(S)-4-carboxy-4-(7-carboxy-heptanoylamino)-butyrylamino]-ethoxy}-ethoxy)-acetylamino}-butyryl ethoxy)-acetylamino]-butyrylamino}-butyryl | |

TABLE 1-continued

| CHEMISTRY | IUPAC name | alternative name |
|---|---|---|
| | (S)-4-Carboxy-4-{(S)-4-carboxy-4-[2-(2-{2-[2-(2-{2-[(S)-4-carboxy-4-(11-carboxy-undecanoylamino)-butyrylamino]-ethoxy}-ethoxy)-acetylamino]-ethoxy}-ethoxy)-acetylamino]-butyrylamino}-butyryl | |
| | (S)-4-Carboxy-4-{(S)-4-carboxy-4-[2-(2-{2-[2-(2-{(S)-4-carboxy-4-(13-carboxy-tridecanoylamino)-butyrylamino]-ethoxy}-ethoxy)-acetylamino]-ethoxy}-ethoxy)-acetylamino]-butyrylamino}-butyryl | |
| | (S)-4-Carboxy-4-{(S)-4-carboxy-4-[2-(2-{2-[2-(2-{(S)-4-carboxy-4-(15-carboxy-pentadecanoyl)amino}-butyrylamino]-ethoxy}-ethoxy)-acetylamino]-ethoxy}-ethoxy)-acetylamino]-butyrylamino}-butyryl | |

TABLE 1-continued

| CHEMISTRY | IUPAC name | alternative name |
|---|---|---|
| | (S)-4-Carboxy-4-{(S)-4-carboxy-4-[2-(2-{2-[2-(2-{2-[(S)-4-carboxy-4-(19-carboxy-nonadecanoylamino)-butyrylamino]-ethoxy}-ethoxy)-acetylamino]-ethoxy}-ethoxy)-acetylamino]-butyrylamino}-butyryl | |
| | 2-(2-[2-{2-[2-(2-{(3S,8S,9S,10R,13R,14S,17R)-10,13-Dimethyl-17-((R)-1,5-dimethyl-hexyl)-2,3,4,7,8,9,10,11,12,13,14,15,16,17-tetradecahydro-1H-cyclopenta[a]phenanthren-3-yloxycarbonyl]-ethoxy}-ethoxy)-ethoxy]-ethoxy}-ethylcarbamoyl)-methyl | |

In a further embodiment, X14 represents Met or Nle, preferably Met.

In a still further embodiment, X3 represents Gln, X16 represents Ser, X17 represents Arg, X18 represents Arg, X19 represents Ala, X20 represents Gln and/or X21 represents Asp or Glu.

In a still further embodiment, X2 represents Ser, D-Ser or Aib, preferably D-Ser or Aib and more preferably D-Ser.

In a still further embodiment, (i) X2 represents D-Ser or Aib and X40 is functionalized Lys, (ii) X2 represents Ser, D-Ser or Aib, X39 is functionalized Lys and X40 is absent, (iii) X2 represents Ser, D-Ser or Aib and X40 is absent, or (iv) X2 represents Ser, D-Ser or Aib and X40 is functionalized Cys.

Lys is preferably functionalized, e.g. with a group —C(O)R5 as described above. Cys is preferably functionalized, e.g. with a group —Y—R7, wherein Y is a thiol linker and R7 is preferably a (poly)alkoxy group, e.g. an (CH2-CH2-O)q-R6 group, wherein q is 1-2000 and R6 is H or C1-4 alkyl.

In a still further embodiment X15 represents Glu, and/or X16 represents Lys or Ser, and/or X19 represents Ala, and/or X20 represents Lys or Gln, and/or X21 represents Leu or Glu.

In a still further embodiment, 1, 2, 3, 4, 5 or 6, particularly 5 or 6 amino acid residues selected from X15, X16, X17, X18, X19, X20 and X21 are amino acid residues which differ from the corresponding amino acid residues in Exendin-4 (SEQ ID NO: 1). This embodiment may particularly be combined with the above indicated specific amino acid residues at positions X15, X16, X17, X18, X19, X20 and/or X21.

A still further embodiment refers to a group of compounds, wherein
   X2=D-Ser;
   X3=Gln;
   X14=Met;
   X15=Asp or Glu;
   X16=Ser;
   X17=Arg;
   X18=Arg or Ala;
   X19=Ala;
   X20=Gln or Arg, particularly Gln;
   X21=Asp or Leu;
   X28=Asn, Ala, Ser, Lys, Aib or Arg;
   X29=Gly or D-Ala;
   X35=Ala; and
   (i) X39=Ser and
   X40=Lys, Orn, Dab or Dap which are functionalized at the amino side chain group, particularly by (S)-4-carboxy-4-hexadecanoylamino-butyryl, (S)-4-carboxy-4-octadecanoylamino-butyryl, octadecanoyl or hexadecanoyl,
   (ii) X39=Lys which is functionalized at its amino side chain group, particularly by (S)-4-carboxy-4-hexadecanoylamino-butyryl, (S)-4-carboxy-4-octadecanoylamino-butyryl, octadecanoyl or hexadecanoyl, and
   X40=absent.

In a still preferred embodiment refers to a group of compounds,
wherein
   X2=D-Ser or Aib;
   X3=Gln;
   X14=Met;
   X15=Asp or Glu;
   X16=Ser, Glu or Lys;
   X17=Arg;
   X18=Arg;
   X19=Ala;
   X20=Gln or Lys;
   X21=Asp;
   X28=Asn, Ser, Lys or Aib;
   X29=Gly, Thr, Ala or D-Ala;
   X35=Ala and
   (i) X39=Ser and
   X40=Lys which is functionalized at the amino side chain group, particularly by (S)-4-carboxy-4-hexadecanoylamino-butyryl, (S)-4-carboxy-4-octadecanoylamino-butyryl, octadecanoyl or hexadecanoyl, or
   (ii) X39=Lys which is functionalized at the amino side chain group, particularly by (S)-4-carboxy-4-hexadecanoylamino-butyryl, (S)-4-carboxy-4-octadecanoylamino-butyryl, octadecanoyl or hexadecanoyl, and
   X40 is absent.

A still further preferred embodiment relates to a group of compounds,
wherein
   X2=D-Ser;
   X3=Gln;
   X14=Nle, Chx-Ala, Cp-Ala or Cb-Ala;
   X15=Asp or Glu;
   X16=Ser;
   X17=Arg;
   X18=Arg or Ala;
   X19=Ala;
   X20=Gln or Lys;
   X21=Asp, Glu or Leu;
   X28=Ala or Ser;
   X29=Gly;
   X35=Ala;
   (i) X39=Ser and
   X40=Lys, Orn, Dab or Dap which are functionalized at the amino side chain group, particularly by (S)-4-Carboxy-4-hexadecanoylamino-butyryl, (S)-4-Carboxy-4-octadecanoylamino-butyryl, octadecanoyl or hexadecanoyl, or
   (ii) X39=Lys which is functionalized at the amino side chain group, particularly by (S)-4-Carboxy-4-hexadecanoylamino-butyryl, (S)-4-Carboxy-4-hexadecanoylamino-butyryl, (S)-4-Carboxy-4-octadecanoylamino-butyryl, octadecanoyl or hexadecanoyl and X40=absent.

A still further preferred embodiment relates to a group of compounds, wherein

X2=Ser or D-Ser;
X3=Gln;
X14=Met;
X15=Asp or Glu;
X16=Ser;
X17=Arg;
X18=Arg;
X19=Ala;
X20=Gln;
X21=Asp;
X28=Asn;
X29=Gly;
X35=Ala; and
(i) X39=Ser and
X40=Lys which is functionalized at the amino side chain group, particularly by (S)-4-carboxy-4-(15-carboxy-pentadecanoylamino)-butyryl, (S)-4-carboxy-4-octadecanoylamino-butyryl, octadecanoyl or hexadecanoyl, or
(ii) X39=Lys which is functionalized at the amino side chain group, particularly by (S)-4-carboxy-4-hexadecanoylamino-butyryl, (S)-4-carboxy-4-octadecanoylamino-butyryl, octadecanoyl or hexadecanoyl, and
X40 is absent.

A still further preferred embodiment relates to a group of compounds wherein

X2=Ser or D-Ser;
X3=Gln;
X14=Met or Nle;
X15=Asp or Glu;
X16=Ser, Glu or Lys;
X17=Arg or Glu;
X18=Arg or Ala;
X19=Ala;
X20=Gln, Arg or Lys;
X21=Asp, Glu or Leu;
X28=Asn;
X29=Gly;
X35=Ala;
X39=Ser and
X40=absent.

A still further preferred embodiment relates to a group of compounds wherein

X2=Aib or D-Ser;
X3=Gln;
X14=Met or Nle;
X15=Asp or Glu;
X16=Ser, Glu or Lys;
X17=Arg, Lys or Gln;
X18=Arg or Ala;
X19=Ala;
X20=Gln or Lys;
X21=Asp;
X28=Asn, Ala, Aib, Lys, Arg or Ser;
X29=Gly, Ala, D-Ala or Thr;
X35=Ala;
X39=Ser and
X40=absent or Lys.

Specific examples of peptidic compounds of formula (I) are the compounds of SEQ ID NO: 7-238 as well as salts and solvates thereof.

In certain embodiments, i.e. when the compound of formula (I) consists of genetically encoded amino acid residues, the invention further provides a nucleic acid (which may be DNA or RNA) encoding said compound, an expression vector comprising such a nucleic acid, and a host cell containing such a nucleic acid or expression vector.

In a further aspect, the present invention provides a composition comprising a compound of the invention in admixture with a carrier. In preferred embodiments, the composition is a pharmaceutically acceptable composition and the carrier is a pharmaceutically acceptable carrier. The compound of the invention may be in the form of a salt, e.g. a pharmaceutically acceptable salt or a solvate, e.g. a hydrate. In still a further aspect, the present invention provides a composition for use in a method of medical treatment, particularly in human medicine.

In certain embodiments, the nucleic acid or the expression vector may be used as therapeutic agents, e.g. in gene therapy.

The compounds of formula (I) are suitable for therapeutic application without an additionally therapeutically effective agent. In other embodiments, however, the compounds are used together with at least one additional therapeutically active agent, which may e.g. be a GLP1 compound and/or an insulinic compound and/or a gastrointestinal peptide.

The compounds of formula (I) are particularly suitable for the treatment or prevention of diseases or disorders caused by, associated with and/or accompanied by disturbances in carbohydrate and/or lipid metabolism, e.g. for the treatment or prevention of hyperglycemia, type 2 diabetes, impaired glucose tolerance, type 1 diabetes, obesity and metabolic syndrome. Further, the compounds of the invention are particularly for the treatment or prevention of degenerative diseases, particularly neurodegenerative diseases.

The compounds described find use, inter alia, in preventing weight gain or promoting weight loss. By "preventing" is meant inhibiting or reducing when compared to the absence of treatment, and is not necessarily meant to imply complete cessation of a disorder.

The compounds of the invention may cause a decrease in food intake and/or increase in energy expenditure, resulting in the observed effect on body weight.

Independently of their effect on body weight, the compounds of the invention may have a beneficial effect on circulating cholesterol levels, being capable of lowering circulating LDL levels and increasing HDL/LDL ratio.

Thus, the compounds of the invention can be used for direct or indirect therapy of any condition caused or characterised by excess body weight, such as the treatment and/or prevention of obesity, morbid obesity, obesity linked inflammation, obesity linked gallbladder disease, obesity induced sleep apnea. They may also be used for treatment and prevention of the metabolic syndrome, diabetes, hypertension, atherogenic dyslipidemia, atherosclerosis, arteriosclerosis, coronary heart disease, or stroke. Their effects in these conditions may be as a result of or associated with their effect on body weight, or may be independent thereof.

Preferred medical uses include delaying or preventing disease progression in type 2 diabetes, treating metabolic syndrome, treating obesity or preventing overweight, for decreasing food intake, increase energy expenditure, reducing body weight, delaying the progression from impaired glucose tolerance (IGT) to type 2 diabetes; delaying the progression from type 2 diabetes to insulin-requiring diabetes; regulating appetite; inducing satiety; preventing weight regain after successful weight loss; treating a disease or state related to overweight or obesity; treating bulimia; treating binge eating; treating atherosclerosis, hypertension, type 2 diabetes, IGT, dyslipidemia, coronary heart disease, hepatic steatosis, treatment of beta-blocker poisoning, use for inhibition of the motility of the gastrointestinal tract, useful in connection with investigations of the gastrointestinal tract using techniques such as X-ray, CT- and NMR-scanning.

Further preferred medical uses include treatment or prevention of hypoglycemia, insulin induced hypoglycemia, reactive hypoglycemia, diabetic hypoglycemia, non-diabetic hypoglycemia, fasting, hypoglycemia, drug-induced hypoglycemia, gastric by-pass induced hypoglycemia, hypoglycemia in pregnancy, alcohol induced hypoglycemia, insulinoma and Von Girkes disease.

Further preferred medical uses include treatment or prevention of degenerative disorders, particularly neurodegenerative disorders such as Alzheimer's disease, Parkinson's disease, Huntington's disease, ataxia, e.g spinocerebellar ataxia, Kennedy disease, myotonic dystrophy, Lewy body dementia, multi-systemic atrophy, amyotrophic lateral sclerosis, primary lateral sclerosis, spinal muscular atrophy, prion-associated diseases, e.g. Creutzfeldt-Jacob disease, multiple sclerosis, telangiectasia, Batten disease, corticobasal degeneration, Creutzfeldt-Jakob disease, subacute combined degeneration of spinal cord, Tabes dorsalis, Tay-Sachs disease, toxic encephalopathy, infantile Refsum disease, Refsum disease, neuroacanthocytosis, Niemann-Pick disease, Lyme disease, Machado-Joseph disease, Sandhoff disease, Shy-Drager syndrome, wobbly hedgehog syndrome, proteopathy, cerebral β-amyloid angiopathy, retinal ganglion cell degeneration in glaucoma, synucleinopathies, tauopathies, frontotemporal lobar degeneration (FTLD), dementia, cadasil syndrome, hereditary cerebral hemorrhage with amyloidosis, Alexander disease, seipinopathies, familial amyloidotic neuropathy, senile systemic amyloidosis, serpinopathies, AL (light chain) amyloidosis (primary systemic amyloidosis), AH (heavy chain) amyloidosis, AA (secondary) amyloidosis, aortic medial amyloidosis, ApoAI amyloidosis, ApoAII amyloidosis, ApoAIV amyloidosis, familial amyloidosis of the Finnish type (FAF), Lysozyme amyloidosis, Fibrinogen amyloidosis, Dialysis amyloidosis, Inclusion body myositis/myopathy, Cataracts, Retinitis pigmentosa with rhodopsin mutations, medullary thyroid carcinoma, cardiac atrial amyloidosis, pituitary prolactinoma, Hereditary lattice corneal dystrophy, Cutaneous lichen amyloidosis, Mallory bodies, corneal lactoferrin amyloidosis, pulmonary alveolar proteinosis, odontogenic (Pindborg) tumor amyloid, cystic fibrosis, sickle cell disease or critical illness myopathy (CIM).

DETAILED DESCRIPTION OF THE INVENTION

Definitions

Figure 1:
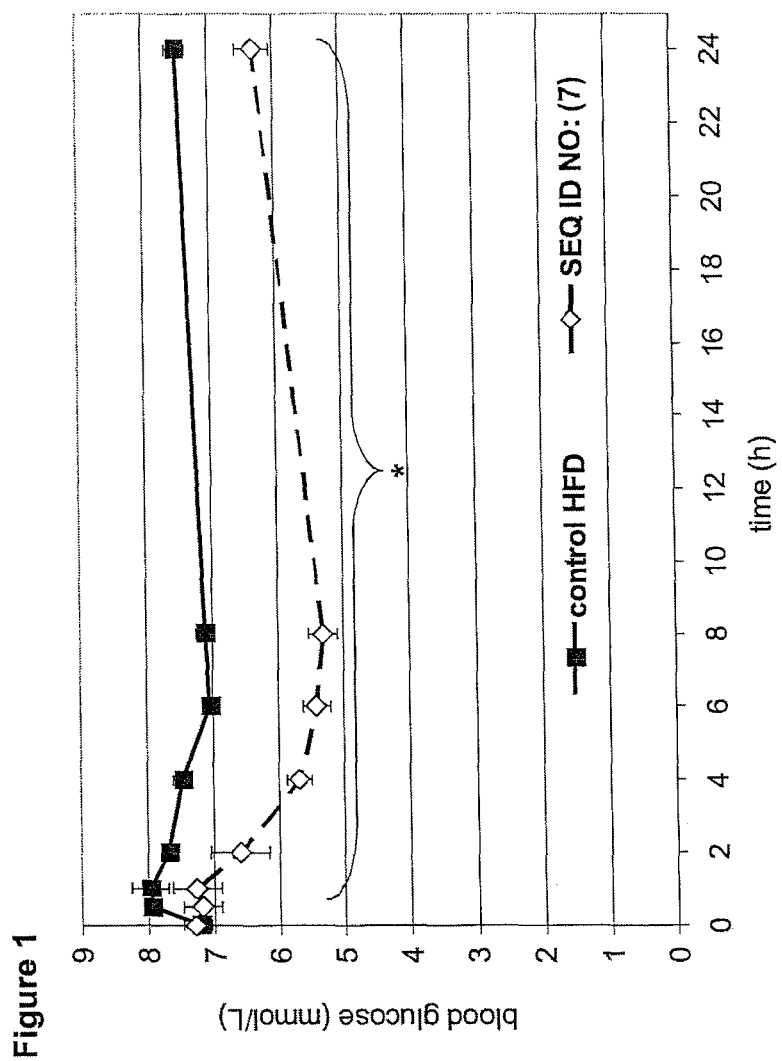
FIG. 1. Effect of s.c. administration of compound SEQ ID NO: (7) on blood glucose in female diet-induced obese C57BL/6NCrl mice (9 months on high-fat diet). Data are mean±SEM. $*p<0.05$.

The amino acid sequences of the present invention contain the conventional one letter and three letter codes for naturally occurring amino acids, as well as generally accepted three letter codes for other amino acids, such as Aib (α-aminoisobutyric acid), Orn (ornithin), Dab (2,4-diamino butyric acid), Dap (2,3-diamino propionic acid), Nle (norleucine), Abt (γ-aminobutyric acid) or Ahx (ε-aminohexanoic acid).

The term "native exendin-4" refers to native exendin-4 having the sequence HGEGTFTSDLSKQMEEEAVR-LFIEWLKNGGPSSGAPPPS-NH2 (SEQ ID NO: (1)).

The invention provides peptidic compounds as defined above.

The peptidic compounds of the present invention comprise a linear backbone of amino carboxylic acids linked by peptide, i.e. carboxamide bonds. Preferably, the amino carboxylic acids are α-amino carboxylic acids and more preferably L-α-amino carboxylic acids, unless indicated otherwise. The peptidic compounds preferably comprise a backbone sequence of 39-41 amino carboxylic acids.

The peptidic compounds may be functionalized (covalently linked) with chemical moieties at their N-terminus, C-terminus and/or at least one side-chain. The N-terminus of the peptidic compound may be unmodified, i.e. an NH2 group or a mono- or bisfunctionalized NH2 group.

At the C-terminus, the peptidic compounds may be unmodified, i.e. have a OH group or be modified, e.g. with an NH2 group or a monofunctionalized or bisfunctionalized NH2 group.

The peptidic compounds of the present invention may have unmodified side-chains or carry at least one modification at one of the side chains.

For the avoidance of doubt, in the definitions provided herein, it is generally intended that the sequence of the peptidic moiety (II) differs from native exendin-4 at least at one of those positions which are stated to allow variation. Amino acids within the peptide moiety (II) can be considered to be numbered consecutively from 0 to 40 in the conventional N-terminal to C-terminal direction. Reference to a "position" within peptidic moiety (II) should be constructed accordingly, as should reference to positions within native exendin-4 and other molecules.

Substitution of one or more of the naturally occurring amino acids at positions 39 and/or 40 with an amino acid having a reactive side chain, e.g. an NH2 or SH group which enables conjugation to a functional group. For example, the residues at positions 39 and/or 40 may be Lys, Orn, Dab, Dap or Cys.

The amino acid side chains may be conjugated with functional, e.g. lipophilic acyl groups. Thus, one or more selected amino acids of the peptides in the present invention may carry a covalent attachment at their side chains. In some cases those attachments may be lipophilic. These lipophilic side chain attachments have the potential to reduce in vivo clearance of the peptides thus increasing their in vivo half-lives.

The lipophilic attachment may consist of a lipophilic moiety which can be a branched or unbranched, aliphatic or unsaturated acyclic moiety and/or a cyclic moiety selected from one or several aliphatic or unsaturated homocycles or heterocycles, aromatic condensed or non-condensed homocycles or heterocycles, ether linkages, unsaturated bonds and substituents, e.g. hydroxy and/or carboxy groups. The lipophilic moiety may be attached to the peptide either directly (alkylation, reductive amination) or by an amide bond or a sulfonamide bond in case of amino acids carrying an amino group at their side chain, an ester bond in case of amino acids carrying a hydroxy group at their side chain or thioether or thioester linkages in case of amino acids carrying a thiol group at their side chain or it may be attached to a modified side-chain of an amino acid thus allowing the introduction of a lipophilic moiety by click-chemistry or Michael-addition.

Nonlimiting examples of lipophilic moieties that can be attached to amino acid side chains include fatty acids, e.g. C12-30 fatty acids such as palmitic acid, myristic acid, stearic acid and oleic acid, and/or cyclic groups as described above or derivatives thereof.

There might be one or several linkers between the amino acid of the peptide and the lipophilic attachment. Nonlimiting examples of those linkers are β-alanine, γ-glutamic acid, γ-aminobutyric acid and/or ε-aminohexanoic acid or dipeptides, such as β-Ala-β-Ala and/or γ-Glu-γ-Glu.

Thus, one nonlimiting example of a side chain attachment is palmitic acid which is covalently linked to the amino group of glutamic acid forming an amide bond. The γ-carboxy group of this substituted glutamic acid can form an amide bond with the side chain amino group of a lysine within the peptide.

In a further aspect, the present invention provides a composition comprising a compound of the invention as described herein, or a salt or solvate thereof, in admixture with a carrier.

The invention also provides the use of a compound of the present invention for use as a medicament, particularly for the treatment of a condition as described below.

The invention also provides a composition wherein the composition is a pharmaceutically acceptable composition, and the carrier is a pharmaceutically acceptable carrier.

Peptide Synthesis

The skilled person is aware of a variety of different methods to prepare peptides that are described in this invention. These methods include but are not limited to synthetic approaches and recombinant gene expression. Thus, one way of preparing these peptides is the synthesis in solution or on a solid support and subsequent isolation and purification. A different way of preparing the peptides is gene expression in a host cell in which a DNA sequence encoding the peptide has been introduced. Alternatively, the gene expression can be achieved without utilizing a cell system. The methods described above may also be combined in any way.

A preferred way to prepare the peptides of the present invention is solid phase synthesis on a suitable resin. Solid phase peptide synthesis is a well established methodology (see for example: Stewart and Young, Solid Phase Peptide Synthesis, Pierce Chemical Co., Rockford, Ill., 1984; E. Atherton and R. C. Sheppard, Solid Phase Peptide Synthesis. A Practical Approach, Oxford-IRL Press, New York, 1989). Solid phase synthesis is initiated by attaching an N-terminally protected amino acid with its carboxy terminus to an inert solid support. This solid support can be any polymer that allows coupling of the initial amino acid such as e.g. a trityl resin, a chlorotrityl resin, a Wang resin or a Rink resin in which the linkage of the carboxy group (or carboxamide for Rink resin) to the resin is sensitive to acid (when Fmoc strategy is used). The polymer support must be stable under the conditions used to deprotect the α-amino group during the peptide synthesis.

After the first amino acid has been coupled to the solid support, the α-amino protecting group of this amino acid is removed. The remaining protected amino acids are then coupled one after the other in the order represented by the peptide sequence using appropriate amide coupling reagents, for example BOP (benzotriazol-1-yl-oxy-tris-(dimethylamino)-phosphonium), HBTU (2-(1H-benzotriazol-1-yl)-1,1,3,3-tetramethyl-uronium), HATU (O-(7-azabenztriazol-1-yl-oxy-tris-(dimethylamino)-phosphonium) or DIC (N,N'-diisopropylcarbodiimide)/HOBt (1-hydroxybenzotriazol), wherein BOP, HBTU and HATU are used with tertiary amine bases. Alternatively, the liberated N-terminus can be functionalized with groups other than amino acids, for example carboxylic acids.

Usually, reactive side-chain groups of the amino acids are protected with suitable blocking groups. These protecting groups are removed after the desired peptides have been assembled. They are commonly removed while the desired product is being cleaved from the resin under the same conditions. Protecting groups and the procedures to introduce protecting groups can be found in Protective Groups in Organic Synthesis, 3d ed., Greene, T. W. and Wuts, P. G. M., Wiley & Sons (New York: 1999).

In some cases it might be desirable to have side-chain protecting groups that can selectively be removed while other side-chain protecting groups remain intact. In this case the liberated functionality can be selectively functionalized. For example, a lysine may be protected with an ivDde protecting group (S. R. Chhabra et al., Tetrahedron Lett. 39, (1998), 1603) which is labile to a very nucleophilic base, for example 4% hydrazine in DMF (dimethyl formamide). Thus, if the N-terminal amino group and all side-chain functionalities are protected with acid labile protecting groups, the ivDde ([1-(4,4-dimethyl-2,6-dioxocyclohex-1-ylidene)-3-methylbutyl) group can be selectively removed using 4% hydrazine in DMF and can then be further modified, e.g. by acylation. The lysine can alternatively be coupled to a protected amino acid and the amino group of this amino acid can then be deprotected resulting in another free amino group which can be acylated or attached to further amino acids.

Finally the peptide is cleaved from the resin. This can be achieved by using King's cocktail (D. S. King, C. G. Fields, G. B. Fields, Int. J. Peptide Protein Res. 36, 1990, 255-266). The raw material can then be purified by chromatography if necessary.

Potency

As used herein, the term "potency" or "in vitro potency" is a measure for the ability of a compound to activate the receptors for GLP-1 or glucagon in a cell-based assay. Numerically, it is expressed as the "EC50 value", which is the effective concentration of a compound that induces a half maximal increase of response (e.g. formation of intracellular cAMP) in a dose-response experiment.

Therapeutic Uses

The compounds of the invention are agonists for the receptors for GLP-1 and/or for glucagon (e.g. "dual agonists"), preferably for GLP-1 and glucagon and may provide an attractive option for targeting the metabolic syndrome by allowing simultaneous treatment of obesity and diabetes.

Metabolic syndrome is a combination of medical disorders that, when occurring together, increase the risk of developing type 2 diabetes, as well as atherosclerotic vascular disease, e.g. heart disease and stroke. Defining medical parameters for the metabolic syndrome include diabetes mellitus, impaired glucose tolerance, raised fasting glucose, insulin resistance, urinary albumin secretion, central obesity, hypertension, elevated triglycerides, elevated LDL cholesterol and reduced HDL cholesterol.

Obesity is a medical condition in which excess body fat has accumulated to the extent that it may have an adverse effect on health and life expectancy and due to its increasing prevalence in adults and children it has become one of the leading preventable causes of death in modern world. It increases the likelihood of various other diseases, including heart disease, type 2 diabetes, obstructive sleep apnoe, certain types of cancer, as well as osteoarthritis, and it is most commonly caused by a combination of excess food intake, reduced energy expenditure, as well as genetic susceptibility.

Diabetes mellitus, often simply called diabetes, is a group of metabolic diseases in which a person has a high blood sugar, either because the body does not produce enough insulin, or because cells do not respond to the insulin that is produced. The most common types of diabetes are: (1) type 1 diabetes, where the body fails to produce insulin; (2) type 2 diabetes, where the body fails to use insulin properly, combined with an increase in insulin deficiency over time, and (3) gestational diabetes, where women develop diabetes due to their pregnancy. All forms of diabetes increase the risk of long-term complications, which typically develop after many years. Most of these long-term complications are based on damage to blood vessels and can be divided into the two categories "macrovascular" disease, arising from atherosclerosis of larger blood vessels and "microvascular" disease, arising from damage of small blood vessels. Examples for macrovascular disease conditions are ischemic heart disease, myocardial infarction, stroke and peripheral vascular disease. Examples for microvascular diseases are diabetic retinopathy, diabetic nephropathy, as well as diabetic neuropathy.

The receptors for GLP-1 and glucagon are both members of the family B of G-protein coupled receptors. They are highly related to each other and share not only a significant level of sequence identity, but have also similar mechanisms of ligand recognition and intracellular signaling pathways.

Similarly, the peptides GLP-1 and glucagon are highly homologous to each other, with similar length and regions of high sequence identity. Both are produced from a common precursor, preproglucagon, which is differentially processed in a tissue-specific manner to yield e.g. GLP-1 in intestinal endocrine cells and glucagon in alpha cells of pancreatic islets.

The incretin hormone GLP-1 is secreted by intestinal endocrine cells in response to food and enhances meal-stimulated insulin secretion. Evidence suggests that GLP-1 secretion is reduced in subjects with impaired glucose tolerance or type 2 diabetes, whereas responsiveness to GLP-1 is still preserved in these patients. Thus, targeting of the GLP-1 receptor with suitable agonists offers an attractive approach for treatment of metabolic disorders, including diabetes. The receptor for GLP-1 is distributed widely, being found mainly in pancreatic islets, brain, heart, kidney and the gastrointestinal tract. In the pancreas, GLP-1 acts in a strictly glucose-dependent manner by increasing secretion of insulin from beta cells. This glucose-dependency shows that activation of GLP-1 receptors is unlikely to cause hypoglycemia.

At the beta cell level, GLP-1 has been shown to promote glucose sensitivity, neogenesis, proliferation, transcription of proinsulin and hypertrophy, as well as antiapoptosis. Other relevant effects of GLP-1 beyond the pancreas include delayed gastric emptying, increased satiety, decreased food intake, reduction of body weight, as well as neuroprotective and cardioprotective effects. In patients with type 2 diabetes, such extrapancreatic effects could be particularly important considering the high rates of comorbidities like obesity and cardiovascular disease.

Glucagon is a 29-amino acid peptide hormone that is produced by pancreatic alpha cells and released into the bloodstream when circulating glucose is low. An important physiological role of glucagon is to stimulate glucose output in the liver, which is a process providing the mayor counterregulatory mechanism for insulin in maintaining glucose homeostasis in vivo.

Glucagon receptors are however also expressed in extrahepatic tissues such as kidney, heart, adipocytes, lymphoblasts, brain, retina, adrenal gland and gastrointestinal tract, suggesting a broader physiological role beyond glucose homeostasis. Accordingly, recent studies have reported that glucagon has therapeutically positive effects on energy management, including stimulation of energy expenditure and thermogenesis, accompanied by reduction of food intake and body weight loss. Altogether, stimulation of glucagon receptors might be useful in the treatment of obesity and the metabolic syndrome.

Oxyntomodulin is a 37-amino acid peptide hormone consisting of glucagon with an eight amino acids encompassing C-terminal extension. Like GLP-1 and glucagon, it is preformed in preproglucagon and cleaved and secreted in a tissue-specific manner by endocrinal cells of the small bowel. Oxyntomodulin is known to stimulate both, the receptors for GLP-1 and glucagon and is therefore the prototype of a dual agonist.

As GLP-1 is known for its anti-diabetic effects, GLP-1 and glucagon are both known for their food intake-suppressing effects and glucagon is also a mediator of additional energy expenditure, it is conceivable that a combination of the activities of the two hormones in one molecule can yield a powerful medication for treatment of the metabolic syndrome and in particular its components diabetes and obesity.

Accordingly, the compounds of the invention may be used for treatment of glucose intolerance, insulin resistance, pre-diabetes, increased fasting glucose, type 2 diabetes, hypertension, dyslipidemia, atherosclerois, arteriosclerosis, coronary heart disease, peripheral artery disease, stroke or any combination of these individual disease components.

In addition, they may be used for control of appetite, feeding and calory intake, increase of energy expenditure, prevention of weight gain, promotion of weight loss, reduction of excess body weight and altogether treatment of obesity, including morbid obesity.

Further disease states and health conditions which could be treated with the compounds of the invention are obesity-linked inflammation, obesity-linked gallbladder disease and obesity-induced sleep apnea.

Although all these conditions could be associated directly or indirectly with obesity, the effects of the compounds of the invention may be mediated in whole or in part via an effect on body weight, or independent thereof.

Further, diseases to be treated are neurodegenerative diseases such as Alzheimer's disease or Parkinson's disease, or other degenerative diseases as described above.

Pharmaceutical Compositions

The term "pharmaceutical composition" indicates a mixture containing ingredients that are compatible when mixed and which may be administered. A pharmaceutical composition may include one or more medicinal drugs. Additionally, the pharmaceutical composition may include carriers, solvents, adjuvants, emollients, expanders, stabilizers and other components, whether these are considered active or inactive ingredients. Guidance for the skilled in preparing pharmaceutical compositions may be found, for example, in Remington: The Science and Practice of Pharmacy, (20th ed.) ed. A. R. Gennaro A. R., 2000, Lippencott Williams & Wilkins.

The exendin-4 peptide analogues of the present invention, or salts thereof, are administered in conjunction with an acceptable pharmaceutical carrier, diluent, or excipient as part of a pharmaceutical composition. A "pharmaceutically acceptable carrier" is a carrier which is physiologically acceptable while retaining the therapeutic properties of the substance with which it is administered. Standard acceptable pharmaceutical carriers and their formulations are known to one skilled in the art and described, for example, in Remington: The Science and Practice of Pharmacy, (20th ed.) ed. A. R. Gennaro A. R., 2000, Lippencott Williams & Wilkins. One exemplary pharmaceutically acceptable carrier is physiological saline solution.

Acceptable pharmaceutical carriers or diluents include those used in formulations suitable for oral, rectal, nasal or parenteral (including subcutaneous, intramuscular, intravenous, intradermal, and transdermal) administration. The compounds of the present invention will typically be administered parenterally.

The term "pharmaceutically acceptable salt" means salts of the compounds of the invention which are safe and effective for use in mammals. Pharmaceutically acceptable salts may include, but are not limited to, acid addition salts and basic salts. Examples of acid addition salts include chloride, sulfate, hydrogen sulfate, (hydrogen) phosphate, acetate, citrate, tosylate or mesylate salts. Examples of basic salts include salts with inorganic cations, e.g. alkaline or alkaline earth metal salts such as sodium, potassium, magnesium or calcium salts and salts with organic cations such as amine salts. Further examples of pharmaceutically acceptable salts are described in Remington: The Science and Practice of Pharmacy, (20th ed.) ed. A. R. Gennaro A. R., 2000, Lippencott Williams & Wilkins or in Handbook of Pharmaceutical Salts, Properties, Selection and Use, e.d. P. H. Stahl, C. G. Wermuth, 2002, jointly published by Verlag Helvetica Chimica Acta, Zurich, Switzerland, and Wiley-VCH, Weinheim, Germany.

The term "solvate" means complexes of the compounds of the invention or salts thereof with solvent molecules, e.g. organic solvent molecules and/or water.

The term "therapeutically effective amount" of a compound refers to a nontoxic but sufficient amount of the compound to provide the desired effect. The amount of a compound of the formula I necessary to achieve the desired biological effect depends on a number of factors, for example the specific compound chosen, the intended use, the mode of administration and the clinical condition of the patient. An appropriate "effective" amount in any individual case may be determined by one of ordinary skill in the art using routine experimentation.

Pharmaceutical compositions of the invention are those suitable for parenteral (for example subcutaneous, intramuscular, intradermal or intravenous), oral, rectal, topical and peroral (for example sublingual) administration, although the most suitable mode of administration depends in each individual case on the nature and severity of the condition to be treated and on the nature of the compound of formula I used in each case.

Suitable pharmaceutical compositions may be in the form of separate units, for example capsules, tablets and powders in vials or ampoules, each of which contains a defined amount of the compound; as powders or granules; as solution or suspension in an aqueous or nonaqueous liquid; or as an oil-in-water or water-in-oil emulsion. It may be provided in single dose injectable form, for example in the form of a pen. The compositions may, as already mentioned, be prepared by any suitable pharmaceutical method which includes a step in which the active ingredient and the carrier (which may consist of one or more additional ingredients) are brought into contact.

Combination Therapy

The compounds of the present invention, dual agonists for the GLP-1 and glucagon receptors, can be widely combined with other pharmacologically active compounds, such as all drugs mentioned in the Rote Liste 2012, e.g. with all antidiabetics mentioned in the Rote Liste 2012, chapter 12, all weight-reducing agents or appetite suppressants mentioned in the Rote Liste 2012, chapter 1, all lipid-lowering agents mentioned in the Rote Liste 2012, chapter 58, all antihypertensives and nephroprotectives, mentioned in the Rote Liste 2012, or all diuretics mentioned in the Rote Liste 2012, chapter 36.

The active ingredient combinations can be used especially for a synergistic improvement in action. They can be applied either by separate administration of the active ingredients to the patient or in the form of combination products in which a plurality of active ingredients are present in one pharmaceutical preparation. When the active ingredients are administered by separate administration of the active ingredients, this can be done simultaneously or successively.

Most of the active ingredients mentioned hereinafter are disclosed in the USP Dictionary of USAN and International Drug Names, US Pharmacopeia, Rockville 2011.

Other active substances which are suitable for such combinations include in particular those which for example potentiate the therapeutic effect of one or more active substances with respect to one of the indications mentioned and/or which allow the dosage of one or more active substances to be reduced.

Therapeutic agents which are suitable for combinations include, for example, antidiabetic agents such as:

Insulin and Insulin derivatives, for example: Glargin/Lantus®, Glulisin/Apidra®, Detemir/Levemir®, Lispro/Humalog®/Liprolog®, Degludec/DegludecPlus, Aspart, basal insulin and analogues (e.g. LY-2605541, LY2963016), PEGylated insulin Lispro, Humulin®, Linjeta, SuliXen®, NN1045, Insulin plus Symlin, fast-acting and short-acting insulins (e.g. Linjeta, PH20, NN1218, HinsBet), (APC-003) hydrogel, oral, inhalable, transdermal and sublingual insulins (e.g. Exubera®, Nasulin®, Afrezza, Tregopil, TPM 02, Capsulin, Oral-lyn®, Cobalamin® oral insulin, ORMD-0801, NN1953, VIAtab). Additionally included are also those insulin derivatives which are bonded to albumin or another protein by a bifunctional linker.

GLP-1, GLP-1 analogues and GLP-1 receptor agonists, for example: Lixisenatide/AVE0010/ZP10/Lyxumia, Exenatide/Exendin-4/Byetta/Bydureon/ITCA 650, Liraglutide/Victoza, Semaglutide, Taspoglutide, Albiglutide, Dulaglutide, rExendin-4, CJC-1134-PC, PB-1023, TTP-054, HM-11260C, CM-3, GLP-1 Eligen, ORMD-0901, NN-9924, Nodexen, Viador-GLP-1, CVX-096, ZYOG-1, ZYD-1, MAR-701, ZP-2929, ZP-3022, CAM-2036, DA-15864, ARI-2651, ARI-2255, Exenatide-XTEN and Glucagon-Xten.

DPP-4 inhibitors, for example: Alogliptin/Nesina, Linagliptin/BI-1356/Ondero/Trajenta/Tradjenta/Trayenta/Tradzenta, Saxagliptin/Onglyza, Sitagliptin/Januvia/Xelevia/Tesave/Janumet/Velmetia, Vildagliptin, Anagliptin, Gemigliptin, Tenegliptin, Melogliptin, Trelagliptin, DA-1229, MK-3102, KM-223.

SGLT2 inhibitors, for example: Canaglifozin, Dapaglifloxin, Remoglifoxin, Sergliflozin, Empagliflozin, Ipraglifloxin, Tofoglifloxin, luseoglifloxin, LX-4211, PF-04971729, RO-4998452, EGT-0001442, DSP-3235.

Biguanides (e.g. Metformin, Buformin, Phenformin), Thiazolidinediones (e.g. Pioglitazone, Rivoglitazone, Rosiglitazone, Troglitazone), dual PPAR agonists (e.g. Aleglitazar, Muraglitazar, Tesaglitazar), Sulfonylureas (e.g. Tolbutamide, Glibenclamide, Glimepiride/Amaryl, Glipizide), Meglitinides (e.g. Nateglinide, Repaglinide, Mitiglinide), Alpha-glucosidase inhibitors (e.g. Acarbose, Miglitol, Voglibose), Amylin and Amylin analogues (e.g. Pramlintide, Symlin).

GPR119 agonists (e.g. GSK-263A, PSN-821, MBX-2982, APD-597), GPR40 agonists (e.g. TAK-875, TUG-424, P-1736, JTT-851, GW9508).

Other suitable combination partners are: Cycloset, inhibitors of 11-beta-HSD (e.g. LY2523199, BMS770767, RG-4929, BMS816336, AZD-8329, HSD-016, BI-135585), activators of glucokinase (e.g. TTP-399, AMG-151, TAK- 329), inhibitors of DGAT (e.g. LCQ-908), inhibitors of protein tyrosinephosphatase 1 (e.g. Trodusquemine), inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrokinase, alpha2-antagonists, CCR-2 antagonists.

One or more lipid lowering agents are also suitable as combination partners, such as for example: HMG-CoA-reductase inhibitors (e.g. Simvastatin, Atorvastatin), fibrates (e.g. Bezafibrate, Fenofibrate), nicotinic acid and the derivatives thereof (e.g. Niacin), PPAR-(alpha, gamma or alpha/gamma) agonists or modulators (e.g. Aleglitazar), PPAR-delta agonists, ACAT inhibitors (e.g. Avasimibe), cholesterol absorption inhibitors (e.g. Ezetimibe), Bile acid-binding substances (e.g. Cholestyramine), ileal bile acid transport inhibitors, MTP inhibitors, or modulators of PCSK9.

HDL-raising compounds such as: CETP inhibitors (e.g. Torcetrapib, Anacetrapid, Dalcetrapid, Evacetrapid, JTT-302, DRL-17822, TA-8995) or ABC1 regulators.

Other suitable combination partners are one or more active substances for the treatment of obesity, such as for example: Sibutramine, Tesofensine, Orlistat, antagonists of the cannabinoid-1 receptor, MCH-1 receptor antagonists, MC4 receptor agonists, NPY5 or NPY2 antagonists (e.g. Velneperit), beta-3-agonists, leptin or leptin mimetics, agonists of the 5HT2c receptor (e.g. Lorcaserin), or the combinations of bupropione/naltrexone, bupropione/zonisamide, bupropione/phentermine or pramlintide/metreleptin.

Other suitable combination partners are:

Further gastrointestinal peptides such as Peptide YY 3-36 (PYY3-36) or analogues thereof, pancreatic polypeptide (PP) or analogues thereof.

Glucagon receptor agonists or antagonists, GIP receptor agonists or antagonists, ghrelin antagonists or inverse agonists, Xenin and analogues thereof.

Moreover, combinations with drugs for influencing high blood pressure, chronic heart failure or atherosclerosis, such as e.g.: Angiotensin II receptor antagonists (e.g. telmisartan, candesartan, valsartan, losartan, eprosartan, irbesartan, olmesartan, tasosartan, azilsartan), ACE inhibitors, ECE inhibitors, diuretics, beta-blockers, calcium antagonists, centrally acting hypertensives, antagonists of the alpha-2-adrenergic receptor, inhibitors of neutral endopeptidase, thrombocyte aggregation inhibitors and others or combinations thereof are suitable.

In another aspect, this invention relates to the use of a compound according to the invention or a physiologically acceptable salt thereof combined with at least one of the active substances described above as a combination partner, for preparing a medicament which is suitable for the treatment or prevention of diseases or conditions which can be affected by binding to the receptors for GLP-1 and glucagon and by modulating their activity. This is preferably a disease in the context of the metabolic syndrome, particularly one of the diseases or conditions listed above, most particularly diabetes or obesity or complications thereof.

The use of the compounds according to the invention, or a physiologically acceptable salt thereof, in combination with one or more active substances may take place simultaneously, separately or sequentially.

The use of the compound according to the invention, or a physiologically acceptable salt thereof, in combination with another active substance may take place simultaneously or at staggered times, but particularly within a short space of time. If they are administered simultaneously, the two active substances are given to the patient together; if they are used at staggered times, the two active substances are given to the patient within a period of less than or equal to 12 hours, but particularly less than or equal to 6 hours.

Consequently, in another aspect, this invention relates to a medicament which comprises a compound according to the invention or a physiologically acceptable salt of such a compound and at least one of the active substances described above as combination partners, optionally together with one or more inert carriers and/or diluents.

The compound according to the invention, or physiologically acceptable salt or solvate thereof, and the additional active substance to be combined therewith may both be present together in one formulation, for example a tablet or capsule, or separately in two identical or different formulations, for example as so-called kit-of-parts.

Methods

General Synthesis of Peptidic Compounds

Materials:

Different Rink-Amide resins (4-(2',4'-Dimethoxyphenyl-Fmoc-aminomethyl)-phenoxyacetamido-norleucylaminomethyl resin) were used for the synthesis of peptide amides with loadings in the range of 0.3-0.4 mmol/g. Suppliers were Merck Biosciences and Agilent Technologies. From the same suppliers 2-chloro-trityl-chloride polystyrene resins with loadings up to 1.4 mmol/g were purchased and used for the synthesis of peptide acids.

Fmoc protected natural amino acids were purchased from Protein Technologies Inc., Senn Chemicals, Merck Biosciences, Novabiochem or Iris Biotech. The following standard amino acids were used throughout the syntheses: Fmoc-L-Ala-OH, Fmoc-L-Asn(Trt)-OH, Fmoc-L-Asp(OtBu)-OH, Fmoc-L-Cys(Trt)-OH, Fmoc-L-Gln(Trt)-OH, Fmoc-L-Glu(OtBu)-OH, Fmoc-Gly-OH, Fmoc-L-His(Trt)-OH, Fmoc-L-Ile-OH, Fmoc-L-Leu-OH, Fmoc-L-Lys(Boc)-OH, Fmoc-L-Met-OH, Fmoc-L-Phe-OH, Fmoc-L-Pro-OH, Fmoc-L-Ser(tBu)-OH, Fmoc-L-Thr(tBu)-OH, Fmoc-L-Trp(Boc)-OH, Fmoc-L-Tyr(tBu)-OH, Fmoc-L-Val-OH.

In addition, the following special amino acids were purchased from the same suppliers as above: Fmoc-L-Lys(ivDde)-OH, Fmoc-Aib-OH, Fmoc-D-Ser(tBu)-OH, Fmoc-D-Ala-OH, Boc-L-His(Boc)-OH and Boc-L-His(Trt)-OH.

The solid phase peptide syntheses were performed on a Prelude Peptide Synthesizer (Protein Technologies Inc) using standard Fmoc chemistry and HBTU/DIPEA activation.

DMF was used as the solvent. Deprotection: 20% piperidine/ DMF for 2×2.5 min. Washes: 7×DMF. Coupling 2:5:10 200 mM AA/500 mM HBTU/2M DIPEA in DMF 2× for 20 min. Washes: 5×DMF.

In cases where a Lys-side-chain was modified, Fmoc-L-Lys(ivDde)-OH was used in the corresponding position. After completion of the synthesis, the ivDde group was removed according to a literature procedure (S. R. Chhabra et al., Tetrahedron Lett. 39, (1998), 1603). The following acylations were carried out by treating the resin with the N-hydroxy succinimide esters of the desired acid or using coupling reagents like HBTU/DIPEA or HOBt/DIC.

All the peptides that had been synthesized were cleaved from the resin with King's cleavage cocktail consisting of 82.5% TFA, 5% phenol, 5% water, 5% thioanisole, 2.5% EDT. The crude peptides were then precipitated in diethyl or diisopropyl ether, centrifuged, and lyophilized. Peptides were analyzed by analytical HPLC and checked by ESI mass spectrometry. Crude peptides were purified by a conventional preparative HPLC purification procedure.

Analytical HPLC was performed on an Agilent 1100 Series HPLC system with a Waters XBridge BEH130 3.5 μm C18 column (2.1×150 mm) at 40° C. with a gradient elution at a flow rate of 0.5 mL/min and monitored at 215 and 280 nm. The gradients were set up as 10% B to 90% B over 15 min and then 90% B for 1 min or as 15% B to 50% B over 12.5 min and then 50% B to 90% B over 3 min. Buffer A=0.1% formic acid in water and B=0.1% formic acid in acetonitrile.

General Preparative HPLC Purification Procedure:

The crude peptides were purified either on an Äkta Purifier System or on a Jasco semiprep HPLC System. Preparative RP-C18-HPLC columns of different sizes and with different flow rates were used depending on the amount of crude peptide to be purified. Acetonitrile+0.1% TFA (B) and water+ 0.1% TFA (A) were employed as eluents. Product-containing fractions were collected and lyophilized to obtain the purified product.

Solubility and Stability-Testing of Exendin-4 Analogues

Prior to the testing of solubility and stability of a peptide batch, its content was determined. Therefore, two parameters were investigated, its purity (HPLC-UV) and the amount of salt load of the batch (ion chromatography). Since synthesized peptides contain primarily trifluoroacetate anions, only anion chromatography was performed. The content was then calculated based on the assumption that peptide-related impurities are detected at the same UV-absorption rate as the target peptide, as well as that cations are not present in the sample.

For solubility testing, the target concentration was 1.0 mg/mL pure compound. Therefore, solutions from solid samples were prepared in different buffer systems with a concentration of 1.0 mg/mL compound based on the previously determined content. HPLC-UV was performed after 2 h of gentle agitation from the supernatant, which was obtained by 20 min of centrifugation at 4000 rpm. The solubility was then determined by comparison with the UV peak areas obtained with a stock solution of the peptide at a concentration of 2 mg/mL in pure water or a variable amount of acetonitrile (optical control that all of the compound is solved). This analysis also served as t0 for the stability testing.

For stability testing, an aliquot of the supernatant obtained for solubility was stored for 7 days at 25° C. After that time course, the sample was centrifuged for 20 min at 4000 rpm and the supernatant was analysed with HPLC-UV.

For determination of the amount of the remaining peptide, the peak areas of the target compound at t0 and t7 were compared, resulting in "% remaining peptide", following the equation % remaining peptide=[(peak area peptide $t7$)×100]/ peak area peptide $t0$.

The amount of soluble degradation products was calculated from the comparison of the sum of the peak areas from all observed impurities reduced by the sum of peak areas observed at t0 (i.e. to determine the amount of newly formed peptide-related species). This value was given in percentual relation to the initial amount of peptide at t0, following the equation:

% soluble degradation products={[(peak area sum of impurities $t7$)−(peak area sum of impurities $t0$)]× 100}/peak area peptide $t0$ The potential difference from the sum of "% remaining peptide" and "% soluble degradation products" to 100% reflects the amount of peptide which did not remain soluble upon stress conditions following the equation % precipitate=100−([% remaining peptide]+[% soluble degradation products])

This precipitate includes non-soluble degradation products, polymers and/or fibrils, which have been removed from analysis by centrifugation.

Anion Chromatography

Instrument: Dionex ICS-2000, pre/column: Ion Pac AG-18 2×50 mm (Dionex)/AS18 2×250 mm (Dionex), eluent: aqueous sodium hydroxide, flow: 0.38 mL/min, gradient: 0-6 min: 22 mM KOH, 6-12 min: 22-28 mM KOH, 12-15 min: 28-50 mM KOH, 15-20 min: 22 mM, suppressor: ASRS 300 2 mm, detection: conductivity.

HPLC-UV

Instrument: Agilent 1100, column: X-Bridge C18 3.5 μm 2.1×150 mm (Waters), eluent: A: H20+500 ppm TFA/B: Methanol, flow: 0.55 ml/min, gradient: 0-5 min: 10-60% B; 5-15 min: 60-99% B; detection: 214 nm.

In Vitro Cellular Assays for GLP-1 Receptor and Glucagon Receptor Efficacy

Agonism of compounds for the two receptors was determined by functional assays measuring cAMP response of HEK-293 cell lines stably expressing human GLP-1 or glucagon receptor.

cAMP content of cells was determined using a kit from Cisbio Corp. (cat. no. 62AM4PEC) based on HTRF (Homogenous Time Resolved Fluorescence). For preparation, cells were split into T175 culture flasks and grown overnight to near confluency in medium (DMEM/10% FBS). Medium was then removed and cells washed with PBS lacking calcium and magnesium, followed by proteinase treatment with accutase (Sigma-Aldrich cat. no. A6964). Detached cells were washed and resuspended in assay buffer (1×HBSS; 20 mM HEPES, 0.1% BSA, 2 mM IBMX) and cellular density determined. They were then diluted to 400000 cells/ml and 25 µl-aliquots dispensed into the wells of 96-well plates. For measurement, 25 µl of test compound in assay buffer was added to the wells, followed by incubation for 30 minutes at room temperature. After addition of HTRF reagents diluted in lysis buffer (kit components), the plates were incubated for 1 hr, followed by measurement of the fluorescence ratio at 665/620 nm. In vitro potency of agonists was quantified by determining the concentrations that caused 50% activation of maximal response (EC50).

Single Subcutaneous Treatment of Exendin-4 Analogue on Blood Glucose in Female Diet-Induced Obese C57BL/6NCrl Mice (9 Months on High-Fat Diet)

Female C57BL/6NCrl mice were housed in groups (n=8) and had ad-libitum access to high-fat diet and water. Initial blood samples were taken just before administration (s.c.) of vehicle (phosphate buffer solution) or the exendin-4 analogue (e.g. SEQ ID NO: (7)) (100 µg/kg in phosphate buffer) in fed DIO mice. The volume of administration was 5 mL/kg. The animals had access to high-fat diet and water during the experiment, food consumption was determined at all time points for blood sampling. Blood glucose levels were measured at t=0.5 h, t=1 h, t=2 h, t=4 h, t=6 h, t=8 h, and t=24 h. Blood sampling was performed by tail incision without anaesthesia.

Statistical analyses were performed with Everstat 6.0 by repeated measures two-way ANOVA and Dunnetts post-hoc analyses. Differences were considered statistically significant at the p<0.05 level.

Gastric Emptying and Intestinal Passage in Mice

Female NMRI-mice of a body weight between 20 and 30 g were used. Mice were adapted to housing conditions for at least one week.

Mice were overnight fasted, while water remained available all the time. On the study day, mice were weighed, single-caged and allowed access to 500 mg of feed for 30 min, while water was removed. At the end of the 30 min feeding period, remaining feed was removed and weighed. 60 min later, a coloured, non-caloric bolus was instilled via gavage into the stomach. The test product or its vehicle in the control group was administered subcutaneously, to reach Cmax when coloured bolus was administered. After another 30 min, the animals were sacrificed and the stomach and the small intestine prepared. The filled stomach was weighed, emptied, carefully cleaned and dried and reweighed. The calculated stomach content indicated the degree of gastric emptying. The small intestine was straightened without force and measured in length. Then the distance from the gastric beginning of the gut to the tip of the farthest travelled intestinal content bolus was measured. The intestinal passage was given as relation in percent of the latter distance and the total length of the small intestine.

Statistical analyses were performed with Everstat 6.0 by Student's T-Test. Differences were considered statistically significant at the p<0.05 level.

Automated Assessment of Feed Intake in Mice

Female NMRI-mice of a body weight between 20 and 30 g were used. Mice were adapted to housing conditions for at least one week and for at least one day single-caged in the assessment equipment, when basal data were recorded simultaneously. On the study day, test product was administered subcutaneously close to the lights-off phase (12 h lights off) and assessment of feed consumption was directly started afterwards. Assessment included continued monitoring (every 30 min) over 22 hours. Repetition of this procedure over several days was possible. Restriction of assessment to 22 hours was for practical reason to allow for reweighing of animals, refilling of feed and water and drug administration between procedures. Results could be assessed as cumulated data over 22 hours or differentiated to 30 min intervals.

Statistical analyses were performed with Everstat 6.0 by two-way ANOVA on repeated measures and Dunnetts post-hoc analyses. Differences were considered statistically significant at the p<0.05 level.

EXAMPLES

The invention is further illustrated by the following examples.

Example 1

Synthesis of SEQ ID NO: (4)
H-His-Gly-Glu-Gly-Thr-Phe-Thr-Ser-Asp-Leu-Ser-Lys-

Gln-Met-Asp-Ser-Arg-Arg-Ala-Gln-Asp-Phe-Ile-Glu-

Trp-Leu-Lys-Asn-Gly-Gly-Pro-Ser-Ser-Gly-Ala-Pro-

Pro-Pro-Ser-NH2

The solid phase synthesis was carried out on Rink-resin with a loading of 0.38 mmol/g, 75-150 µm from the company Agilent Technologies. The Fmoc-synthesis strategy was applied with HBTU/DIPEA-activation. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (XBridge, BEH130, Prep C18, 5 µM) using an acetonitrile/water gradient (both buffers with 0.1% TFA).

Finally, the molecular mass of the purified peptide was confirmed by LC-MS. M.W. (calculated)=4188.5 g/mol; M.W. (found)=4188.6 g/mol.

Example 2

Synthesis of SEQ ID NO: (5)
H-His-Ser-Gln-Gly-Thr-Phe-Thr-Ser-Asp-Leu-Ser-Lys-
Gln-Met-Asp-Glu-Arg-Arg-Ala-Gln-Asp-Phe-Ile-Glu-
Trp-Leu-Lys-Asn-Gly-Gly-Pro-Ser-Ser-Gly-Ala-Pro-
Pro-Pro-Ser-NH2

The solid phase synthesis was carried out on Novabiochem Rink-Amide resin (4-(2',4'-Dimethoxyphenyl-Fmoc-aminomethyl)-phenoxyacetamido-norleucylaminomethyl resin), 100-200 mesh, loading of 0.34 mmol/g. The Fmoc-synthesis strategy was applied with HBTU/DIPEA-activation. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS. M.W. (calculated)=4259.6 g/mol; M.W. (found)=4259.0 g/mol.

Example 3

Synthesis of SEQ ID NO: (6)
H-His-Ser-Gln-Gly-Thr-Phe-Thr-Ser-Asp-Leu-Ser-Lys-
Gln-Met-Asp-Ser-Arg-Arg-Ala-Gln-Asp-Phe-Ile-Glu-
Trp-Leu-Lys-Asn-Gly-Gly-Pro-Ser-Ser-Gly-Ala-Pro-
Pro-Pro-Lys(N-ε-(γ-Glu(N-α-hexadecanoyl)))-NH2.

The synthesis and purification was carried out as described in example 2. In position 39 Fmoc-Lys(ivDde)-OH and in position 1 Boc-His(Boc)-OH were used in the solid phase synthesis protocol. The ivDde-group was cleaved from the peptide on resin according to literature (S. R. Chhabra et al., Tetrahedron Lett. 39, (1998), 1603). Hereafter Palm(γOSu)(αOtBu)Glu was coupled to the liberated amino-group. The molecular mass of the purified peptide was confirmed by LC-MS. M.W. (calculated)=4626.2 g/mol; M.W. (found)=4626.2 g/mol.

Example 4

Synthesis of SEQ ID NO: (7)
H-His-D-Ser-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Asn-Gly-Gly-Pro-Ser-Ser-Gly-Ala-
Pro-Pro-Pro-Ser-Lys(N-ε-(γ-Glu(N-α-hexadecanoyl)))-NH2.

The synthesis and purification was carried out as described in example 2. In position 40 Fmoc-Lys(ivDde)-OH and in position 1 Boc-His(Boc)-OH were used in the solid phase synthesis protocol. The ivDde-group was cleaved from the peptide on resin according to literature (S. R. Chhabra et al., Tetrahedron Lett. 39, (1998), 1603). Hereafter Palm(γOSu)(αOtBu)Glu was coupled to the liberated amino-group. The molecular mass of the purified peptide was confirmed by LC-MS. M.W. (calculated)=4713.3 g/mol; M.W. (found)=4712.7 g/mol.

Example 5

Synthesis of SEQ ID NO: (8)
H-His-Ser-Gln-Gly-Thr-Phe-Thr-Ser-Asp-Leu-Ser-Lys-
Gln-Met-Asp-Ser-Arg-Arg-Ala-Gln-Asp-Phe-Ile-Glu-
Trp-Leu-Lys-Asn-Gly-Gly-Pro-Ser-Ser-Gly-Ala-Pro-
Pro-Pro-Ser-NH—CH2—CH2—SH.

The resin used for synthesis was purchased from Iris Biotech (1-amino-ethane-2-thiol (cysteamine)-Mmt Resin; 0.4 mmol/g; 200-400 mesh). Peptide synthesis with this resin, cleavage and purification was carried out as described in example 1. The molecular mass of the purified peptide was confirmed by LC-MS. M.W. (calculated)=4277.8 g/mol; M.W. (found)=4277.5 g/mol.

Example 6

Synthesis of SEQ ID NO: (9)
H-His-Ser-Gln-Gly-Thr-Phe-Thr-Ser-Asp-Leu-Ser-Lys-
Gln-Met-Asp-Ser-Arg-Arg-Ala-Gln-Asp-Phe-Ile-Glu-
Trp-Leu-Lys-Asn-Gly-Gly-Pro-Ser-Ser-Gly-Ala-Pro-
Pro-Pro-Ser-NH2.

The synthesis and purification was carried out as described in example 1. The molecular mass of the purified peptide was confirmed by LC-MS. M.W. (calculated)=4217.6 g/mol; M.W. (found)=4217.1 g/mol.

Example 7

Synthesis of SEQ ID NO: (10)
H-His-Ser-Glu-Gly-Thr-Phe-Thr-Ser-Asp-Leu-Ser-Lys-
Gln-Met-Asp-Ser-Arg-Arg-Ala-Gln-Asp-Phe-Ile-Glu-
Trp-Leu-Lys-Asn-Gly-Gly-Pro-Ser-Ser-Gly-Ala-Pro-
Pro-Pro-Ser-NH2.

The synthesis and purification was carried out as described in example 1. The molecular mass of the purified peptide was confirmed by LC-MS. M.W. (calculated)=4218.6 g/mol; M.W. (found)=4218.1 g/mol.

Example 8

```
Synthesis of SEQ ID NO: (11)
H-His-Gly-Gln-Gly-Thr-Phe-Thr-Ser-Asp-Leu-Ser-Lys- Gln-Met-Asp-Ser-Arg-Arg-Ala-Gln-Asp-Phe-Ile-Glu- Trp-Leu-Lys-Asn-Gly-Gly-Pro-Ser-Ser-Gly-Ala-Pro- Pro-Pro-Ser-NH2.
```

The synthesis and purification was carried out as described in example 1. The molecular mass of the purified peptide was confirmed by LC-MS. M.W. (calculated)=4187.6 g/mol; M.W. (found)=4187.2 g/mol.

Example 9

```
Synthesis of SEQ ID NO: (12)
H-His-Ser-Gln-Gly-Thr-Phe-Thr-Ser-Asp-Leu-Ser-Lys- Gln-Met-Asp-Ser-Arg-Ala-Val-Arg-Leu-Phe-Ile-Glu- Trp-Leu-Lys-Asn-Gly-Gly-Pro-Ser-Ser-Gly-Ala-Pro- Pro-Pro-Ser-NH2.
```

The synthesis and purification was carried out as described in example 1. The molecular mass of the purified peptide was confirmed by LC-MS. M.W. (calculated)=4186.7 g/mol; M.W. (found)=4186.6 g/mol.

Example 10

```
Synthesis of SEQ ID NO: (13)
H-His-Ser-Gln-Gly-Thr-Phe-Thr-Ser-Asp-Leu-Ser-Lys- Gln-Met-Asp-Ser-Arg-Arg-Val-Arg-Leu-Phe-Ile-Glu- Trp-Leu-Lys-Asn-Gly-Gly-Pro-Ser-Ser-Gly-Ala-Pro- Pro-Pro-Ser-NH2.
```

The synthesis and purification was carried out as described in example 1. The molecular mass of the purified peptide was confirmed by LC-MS. M.W. (calculated)=4271.8 g/mol; M.W. (found)=4272.0 g/mol.

Example 11

```
Synthesis of SEQ ID NO: (14)
H-His-Aib-Gln-Gly-Thr-Phe-Thr-Ser-Asp-Leu-Ser-Lys- Gln-Met-Asp-Ser-Arg-Arg-Ala-Gln-Asp-Phe-Ile-Glu- Trp-Leu-Lys-Asn-Gly-Gly-Pro-Ser-Ser-Gly-Ala-Pro- Pro-Pro-Ser-NH2.
```

The synthesis and purification was carried out as described in example 1. The molecular mass of the purified peptide was confirmed by LC-MS. M.W. (calculated)=4215.6 g/mol; M.W. (found)=4215.5 g/mol.

Example 12

```
Synthesis of SEQ ID NO: (15)
H-His-Ser-Gln-Gly-Thr-Phe-Thr-Ser-Asp-Leu-Ser-Lys- Gln-Met-Glu-Glu-Arg-Arg-Ala-Gln-Asp-Phe-Ile-Glu- Trp-Leu-Lys-Asn-Gly-Gly-Pro-Ser-Ser-Gly-Ala-Pro- Pro-Pro-Ser-NH2.
```

The synthesis and purification was carried out as described in example 2. The molecular mass of the purified peptide was confirmed by LC-MS. M.W. (calculated)=4273.7 g/mol; M.W. (found)=4273.5 g/mol.

Example 13

```
Synthesis of SEQ ID NO: (16)
H-His-Ser-Gln-Gly-Thr-Phe-Thr-Ser-Asp-Leu-Ser-Lys- Gln-Met-Glu-Glu-Arg-Arg-Ala-Lys-Asp-Phe-Ile-Glu- Trp-Leu-Lys-Asn-Gly-Gly-Pro-Ser-Ser-Gly-Ala-Pro- Pro-Pro-Ser-NH2.
```

The synthesis and purification was carried out as described in example 2. The molecular mass of the purified peptide was confirmed by LC-MS. M.W. (calculated)=4273.7 g/mol; M.W. (found)=4273.6 g/mol.

Example 14

```
Synthesis of SEQ ID NO: (17)
H-His-Ser-Gln-Gly-Thr-Phe-Thr-Ser-Asp-Leu-Ser-Lys- Gln-Met-Glu-Glu-Glu-Arg-Ala-Lys-Asp-Phe-Ile-Glu- Trp-Leu-Lys-Asn-Gly-Gly-Pro-Ser-Ser-Gly-Ala-Pro- Pro-Pro-Ser-NH2.
```

The synthesis and purification was carried out as described in example 2. The molecular mass of the purified peptide was confirmed by LC-MS. M.W. (calculated)=4246.6 g/mol; M.W. (found)=4246.4 g/mol.

Example 15

Synthesis of SEQ ID NO: (18)
H-His-Ser-Gln-Gly-Thr-Phe-Thr-Ser-Asp-Leu-Ser-Lys-
Gln-Met-Glu-Glu-Glu-Ala-Ala-Lys-Leu-Phe-Ile-Glu-
Trp-Leu-Lys-Asn-Gly-Gly-Pro-Ser-Ser-Gly-Ala-Pro-
Pro-Pro-Ser-NH2.

The synthesis and purification was carried out as described in example 2. The molecular mass of the purified peptide was confirmed by LC-MS. M.W. (calculated)=4159.6 g/mol; M.W. (found)=4159.1 g/mol.

Example 16

Synthesis of SEQ ID NO: (19)
H-His-Ser-Gln-Gly-Thr-Phe-Thr-Ser-Asp-Leu-Ser-Lys-
Gln-Met-Asp-Lys-Arg-Arg-Ala-Gln-Asp-Phe-Ile-Glu-
Trp-Leu-Lys-Asn-Gly-Gly-Pro-Ser-Ser-Gly-Ala-Pro-
Pro-Pro-Ser-NH2.

The synthesis and purification was carried out as described in example 2. The molecular mass of the purified peptide was confirmed by LC-MS. M.W. (calculated)=4258.7 g/mol; M.W. (found)=4258.5 g/mol.

Example 17

Synthesis of SEQ ID NO: (20)
H-His-Ser-Gln-Gly-Thr-Phe-Thr-Ser-Asp-Leu-Ser-Lys-
Gln-Met-Asp-Ser-Arg-Arg-Ala-Gln-Asp-Phe-Ile-Glu-
Trp-Leu-Lys-Asn-Gly-Gly-Pro-Ser-Ser-Gly-Ala-Pro-
Pro-Pro-Lys(N-ε-(γ-Glu(N-α-(ω-carboxypenta-
decanoyl))))-NH2.

The synthesis and purification was carried out as described in example 3. The molecular mass of the purified peptide was confirmed by LC-MS. M.W. (calculated)=4626.2 g/mol; M.W. (found)=4626.2 g/mol.

Example 18

Synthesis of SEQ ID NO: (21)
H-His-Ser-Gln-Gly-Thr-Phe-Thr-Ser-Asp-Leu-Ser-Lys-
Gln-Met-Asp-Ser-Arg-Arg-Ala-Gln-Asp-Phe-Ile-Glu-
Trp-Leu-Lys-Asn-Gly-Gly-Pro-Ser-Ser-Gly-Ala-Pro-
Pro-Pro-Lys(N-ε-(hexadecanoyl))-NH2.

The synthesis and purification was carried out as described in example 3. The molecular mass of the purified peptide was confirmed by LC-MS. M.W. (calculated)=4497.1 g/mol; M.W. (found)=4497.1 g/mol.

Example 19

Synthesis of SEQ ID NO: (22)
H-His-Ser-Gln-Gly-Thr-Phe-Thr-Ser-Asp-Leu-Ser-Lys-
Gln-Met-Asp-Ser-Arg-Ala-Ala-Gln-Leu-Phe-Ile-Glu-
Trp-Leu-Lys-Asn-Gly-Gly-Pro-Ser-Ser-Gly-Ala-Pro-
Pro-Pro-Ser-NH2.

The synthesis and purification was carried out as described in example 2. The molecular mass of the purified peptide was confirmed by LC-MS. M.W. (calculated)=4130.6 g/mol; M.W. (found)=4130.0 g/mol.

Example 20

Synthesis of SEQ ID NO: (23)
H-D-His-Ser-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Asn-Gly-Gly-Pro-Ser-Ser-Gly-Ala-
Pro-Pro-Pro-Ser-NH2.

The synthesis and purification was carried out as described in example 1. In position 1 Fmoc-D-His(Trt)-OH was used in the solid phase synthesis protocol. The molecular mass of the purified peptide was confirmed by LC-MS. M.W. (calculated)= 4217.6 g/mol; M.W. (found)=4217.5 g/mol.

Example 21

Synthesis of SEQ ID NO: (24)
His-Ser-Gln-Gly-Thr-Phe-Thr-Ser-Asp-Leu-Ser-Lys-
Gln-Met-Asp-Ser-Arg-Arg-Ala-Gln-Asp-Phe-Ile-Glu-
Trp-Leu-Lys-Asn-Gly-Gly-Pro-Ser-Ser-Gly-Ala-Pro-
Pro-Pro-Ser-NH2.

The synthesis and purification was carried out as described in example 1. In position 1 Des-amino His(Trt)-OH was used in the solid phase synthesis protocol. The molecular mass of the purified peptide was confirmed by LC-MS. M.W. (calculated)=4202.6 g/mol; M.W. (found)=4202.5 g/mol.

Example 22

Synthesis of SEQ ID NO: (25)
H-His-Ser-MeGln-Gly-Thr-Phe-Thr-Ser-Asp-Leu-Ser-
Lys-Gln-Met-Asp-Ser-Arg-Arg-Ala-Gln-Asp-Phe-Ile- -continued
```
Glu-Trp-Leu-Lys-Asn-Gly-Gly-Pro-Ser-Ser-Gly-Ala-
Pro-Pro-Pro-Ser-NH2.
```

The synthesis and purification was carried out as described in example 1. In position 3 N-methylated Gln was used in the solid phase synthesis, the protocol therefore was described in literature (E. Biron, J. Chatterjee, H. Kessler, J. Peptide Sci. 12, 2006, 213-219). The molecular mass of the purified peptide was confirmed by LC-MS. M.W. (calculated)=4231.6 g/mol; M.W. (found)=4231.5 g/mol.

Example 23

```
Synthesis of SEQ ID NO: (26)
H-His-D-Ser-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Asn-Gly-Gly-Pro-Ser-Ser-Gly-Ala-
Pro-Pro-Pro-Ser-Lys(N-ε-(hexadecanoyl))-NH2.
```

The synthesis and purification was carried out as described in example 4. The molecular mass of the purified peptide was confirmed by LC-MS. M.W. (calculated)=4584.2 g/mol; M.W. (found)=4583.5 g/mol.

Example 24

```
Synthesis of SEQ ID NO: (27)
H-His-D-Ser-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Asn-Gly-Gly-Pro-Ser-Ser-Gly-Ala-
Pro-Pro-Pro-Ser-Lys(N-ε-(γ-Glu(N-α-(ω-carboxy-
pentadecanoyl))))-NH2.
```

The synthesis and purification was carried out as described in example 4. The molecular mass of the purified peptide was confirmed by LC-MS. M.W. (calculated)=4743.3 g/mol; M.W. (found)=4742.6 g/mol.

Example 25

```
Synthesis of SEQ ID NO: (28)
H-His-Ser(Me)-Gln-Gly-Thr-Phe-Thr-Ser-Asp-Leu-
Ser-Lys-Gln-Met-Asp-Ser-Arg-Arg-Ala-Gln-Asp-Phe-
Ile-Glu-Trp-Leu-Lys-Asn-Gly-Gly-Pro-Ser-Ser-Gly-
Ala-Pro-Pro-Pro-Ser-NH2.
```

The synthesis and purification was carried out as described in example 1. In position 2 Fmoc-Ser(Me)-OH was used in the solid phase synthesis protocol. The molecular mass of the purified peptide was confirmed by LC-MS. M.W. (calculated)= 4231.7 g/mol; M.W. (found)=4231.4 g/mol.

Example 26

```
Synthesis of SEQ ID NO: (29)
H-His-D-Ser-Gln-Gly-Thr-Phe-Thr-Ser-Asp-Leu-Ser-
Lys-Gln-Met-Asp-Ser-Arg-Arg-Ala-His-Asp-Phe-Ile-
Glu-Trp-Leu-Lys-Asn-Gly-Gly-Pro-Ser-Ser-Gly-Ala-
Pro-Pro-Pro-Ser-NH2.
```

The synthesis and purification was carried out as described in example 2. The molecular mass of the purified peptide was confirmed by LC-MS. M.W. (calculated)=4226.6 g/mol; M.W. (found)=4226.0 g/mol.

Example 27

```
Synthesis of SEQ ID NO: (30)
H-His-D-Ser-Gln-Gly-Thr-Phe-Thr-Ser-Asp-Leu-Ser-
Lys-Gln-Met-Asp-Ser-Arg-Arg-Ala-Lys-Asp-Phe-Ile-
Glu-Trp-Leu-Lys-Asn-Gly-Gly-Pro-Ser-Ser-Gly-Ala-
Pro-Pro-Pro-Ser-NH2.
```

The synthesis and purification was carried out as described in example 2. The molecular mass of the purified peptide was confirmed by LC-MS. M.W. (calculated)=4217.6 g/mol; M.W. (found)=4217.0 g/mol.

Example 28

```
Synthesis of SEQ ID NO: (31)
H-His-D-Ser-Gln-Gly-Thr-Phe-Thr-Ser-Asp-Leu-Ser-
Lys-Gln-Met-Asp-Ser-Arg-Arg-Ala-Arg-Asp-Phe-Ile-
Glu-Trp-Leu-Lys-Asn-Gly-Gly-Pro-Ser-Ser-Gly-Ala-
Pro-Pro-Pro-Ser-NH2.
```

The synthesis and purification was carried out as described in example 2. The molecular mass of the purified peptide was confirmed by LC-MS. M.W. (calculated)=4245.7 g/mol; M.W. (found)=4245.2 g/mol.

Example 29

```
Synthesis of SEQ ID NO: (32)
H-His-D-Ser-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Arg-Gly-Gly-Pro-Ser-Ser-Gly-Ala-
Pro-Pro-Pro-Ser-NH2.
```

The synthesis and purification was carried out as described in example 2. The molecular mass of the purified peptide was confirmed by LC-MS. M.W. (calculated)=4259.7 g/mol; M.W. (found)=4259.0 g/mol.

Example 30

```
Synthesis of SEQ ID NO: (33)
H-His-D-Ser-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Lys-Gly-Gly-Pro-Ser-Ser-Gly-Glu-
Pro-Pro-Pro-Ser-NH2.
```

The synthesis and purification was carried out as described in example 2. The molecular mass of the purified peptide was confirmed by LC-MS. M.W. (calculated)=4289.7 g/mol; M.W. (found)=4289.0 g/mol.

Example 31

```
Synthesis of SEQ ID NO: (34)
H-His-D-Ser-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Lys-Gly-Gly-Pro-Ser-Ser-Gly-Glu-
Pro-Pro-Pro-Ser-NH2.
```

The synthesis and purification was carried out as described in example 2. The molecular mass of the purified peptide was confirmed by LC-MS. M.W. (calculated)=4231.7 g/mol; M.W. (found)=4231.0 g/mol.

Example 32

```
Synthesis of SEQ ID NO: (35)
H-His-D-Ser-Gln-Gly-Thr-Phe-Thr-Ser-Asp-Leu-Ser-
Lys-Gln-Met-Asp-Ser-Arg-Arg-Ala-Gln-Leu-Phe-Ile-
Glu-Trp-Leu-Lys-Asn-Gly-Gly-Pro-Ser-Ser-Gly-Ala-
Pro-Pro-Pro-Ser-NH2.
```

The synthesis and purification was carried out as described in example 2. The molecular mass of the purified peptide was confirmed by LC-MS. M.W. (calculated)=4215.7 g/mol; M.W. (found)=4215.2 g/mol.

Example 33

```
Synthesis of SEQ ID NO: (36)
H-His-Ser-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Asn-Gly-Gly-Pro-Ser-Ser-Gly-Ala-
Pro-Pro-Pro-Ser-NH—CH2—CH2—S—tBu.
```

This peptide could be isolated via preparative HPLC from the crude product obtained in example 5. The molecular mass of the purified peptide was confirmed by LC-MS. M.W. (calculated)=4333.9 g/mol; M.W. (found)=4333.6 g/mol.

Example 34

```
Synthesis of SEQ ID NO: (37)
H-His-D-Ser-Gln-Gly-Thr-Phe-Thr-Ser-Asp-Leu-Ser-
Lys-Gln-Met-Asp-Ser-Arg-Arg-Ala-Gln-Glu-Phe-Ile-
Glu-Trp-Leu-Lys-Asn-Gly-Gly-Pro-Ser-Ser-Gly-Ala-
Pro-Pro-Pro-Ser-NH2.
```

The synthesis and purification was carried out as described in example 2. The molecular mass of the purified peptide was confirmed by LC-MS. M.W. (calculated)=4231.6 g/mol; M.W. (found)=4231.0 g/mol.

Example 35

```
Synthesis of SEQ ID NO: (38)
H-His-D-Ser-Gln-Gly-Thr-Phe-Thr-Ser-Asp-Leu-Ser-
Lys-Gln-Aib-Asp-Ser-Arg-Arg-Ala-Gln-Asp-Phe-Ile-
Glu-Trp-Leu-Lys-Asn-Gly-Gly-Pro-Ser-Ser-Gly-Ala-
Pro-Pro-Pro-Ser-NH2.
```

The synthesis and purification was carried out as described in example 2. The molecular mass of the purified peptide was confirmed by LC-MS. M.W. (calculated)=4171.5 g/mol; M.W. (found)=4171.0 g/mol.

Example 36

```
Synthesis of SEQ ID NO: (39)
H-His-Ala-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Asn-Gly-Gly-Pro-Ser-Ser-Gly-Ala-
Pro-Pro-Pro-Ser-NH2.
```

The synthesis and purification was carried out as described in example 2. The molecular mass of the purified peptide was confirmed by LC-MS. M.W. (calculated)=4201.6 g/mol; M.W. (found)=4201.0 g/mol.

Example 37

```
Synthesis of SEQ ID NO: (40)
H-His-D-Ala-Gln-Gly-Thr-Phe-Thr-Ser-Asp-Leu-Ser-
Lys-Gln-Met-Asp-Ser-Arg-Arg-Ala-Gln-Asp-Phe-Ile-
```

Glu-Trp-Leu-Lys-Asn-Gly-Gly-Pro-Ser-Ser-Gly-Ala-

Pro-Pro-Pro-Ser-NH2.

The synthesis and purification was carried out as described in example 2. The molecular mass of the purified peptide was confirmed by LC-MS. M.W. (calculated)=4201.6 g/mol; M.W. (found)=4201.0 g/mol.

Example 38

Synthesis of SEQ ID NO: (41)
H-His-D-Ser-Gln-Gly-Thr-Phe-Thr-Ser-Asp-Leu-Ser-

Lys-Gln-Met-Asp-Ser-Arg-Arg-Ala-Gln-Asp-Phe-Ile-

Glu-Trp-Leu-Lys-Ala-Gly-Gly-Pro-Ser-Ser-Gly-Ala-

Pro-Pro-Pro-Ser-NH2.

The synthesis and purification was carried out as described in example 2. The molecular mass of the purified peptide was confirmed by LC-MS. M.W. (calculated)=4174.6 g/mol; M.W. (found)=4174.1 g/mol.

Example 39

Synthesis of SEQ ID NO: (42)
H-His-D-Ser-Gln-Gly-Thr-Phe-Thr-Ser-Asp-Leu-Ser-

Lys-Gln-Met-Asp-Ser-Arg-Arg-Ala-Gln-Asp-Phe-Ile-

Glu-Trp-Leu-Lys-Aib-Gly-Gly-Pro-Ser-Ser-Gly-Ala-

Pro-Pro-Pro-Ser-NH2.

The synthesis and purification was carried out as described in example 2. The molecular mass of the purified peptide was confirmed by LC-MS. M.W. (calculated)=4188.6 g/mol; M.W. (found)=4188.4 g/mol.

Example 40

Synthesis of SEQ ID NO: (43)
H-His-D-Ser-Gln-Gly-Thr-Phe-Thr-Ser-Asp-Leu-Ser-

Lys-Gln-Phe-Asp-Ser-Arg-Arg-Ala-Gln-Asp-Phe-Ile-

Glu-Trp-Leu-Lys-Asn-Gly-Gly-Pro-Ser-Ser-Gly-Ala-

Pro-Pro-Pro-Ser-NH2.

The synthesis and purification was carried out as described in example 2. The molecular mass of the purified peptide was confirmed by LC-MS. M.W. (calculated)=4233.6 g/mol; M.W. (found)=4233.1 g/mol.

Example 41

Synthesis of SEQ ID NO: (44)
H-His-Ser-Gln-Gly-Thr-Phe-Thr-Ser-Asp-Leu-Ser-

Lys-Gln-Met-Glu-Glu-Glu-Ala-Val-Arg-Leu-Phe-Ile-

Glu-Trp-Leu-Lys-Asn-Gly-Gly-Pro-Ser-Ser-Gly-Ala-

Pro-Pro-Pro-Ser-NH2.

The synthesis and purification was carried out as described in example 2. The molecular mass of the purified peptide was confirmed by LC-MS. M.W. (calculated)=4215.7 g/mol; M.W. (found)=4215.2 g/mol.

Example 42

Synthesis of SEQ ID NO: (45)
H-His-Gly-Gln-Gly-Thr-Phe-Thr-Ser-Asp-Leu-Ser-

Lys-Gln-Met-Glu-Glu-Glu-Ala-Val-Arg-Leu-Phe-Ile-

Glu-Trp-Leu-Lys-Asn-Gly-Gly-Pro-Ser-Ser-Gly-Ala-

Pro-Pro-Pro-Ser-NH2.

The synthesis and purification was carried out as described in example 2. The molecular mass of the purified peptide was confirmed by LC-MS. M.W. (calculated)=4185.6 g/mol; M.W. (found)=4185.2 g/mol.

Example 43

Synthesis of SEQ ID NO: (46)
H-His-Ser-Gln-Gly-Thr-Phe-Thr-Ser-Asp-Leu-Ser-

Lys-Gln-Met-Asp-Glu-Glu-Ala-Val-Arg-Leu-Phe-Ile-

Glu-Trp-Leu-Lys-Asn-Gly-Gly-Pro-Ser-Ser-Gly-Ala-

Pro-Pro-Pro-Ser-NH2.

The synthesis and purification was carried out as described in example 2. The molecular mass of the purified peptide was confirmed by LC-MS. M.W. (calculated)=4201.6 g/mol; M.W. (found)=4201.0 g/mol.

Example 44

Synthesis of SEQ ID NO: (47)
H-His-Ser-Gln-Gly-Thr-Phe-Thr-Ser-Asp-Leu-Ser-

Lys-Gln-Met-Glu-Ser-Glu-Ala-Val-Arg-Leu-Phe-Ile-

Glu-Trp-Leu-Lys-Asn-Gly-Gly-Pro-Ser-Ser-Gly-Ala-

Pro-Pro-Pro-Ser-NH2.

The synthesis and purification was carried out as described in example 2. The molecular mass of the purified peptide was confirmed by LC-MS. M.W. (calculated)=4173.6 g/mol; M.W. (found)=4173.0 g/mol.

Example 45

```
Synthesis of SEQ ID NO: (48)
H-His-Ser-Gln-Gly-Thr-Phe-Thr-Ser-Asp-Leu-Ser-
Lys-Gln-Met-Glu-Glu-Arg-Ala-Val-Arg-Leu-Phe-Ile-
Glu-Trp-Leu-Lys-Asn-Gly-Gly-Pro-Ser-Ser-Gly-Ala-
Pro-Pro-Pro-Ser-NH2.
```

The synthesis and purification was carried out as described in example 2. The molecular mass of the purified peptide was confirmed by LC-MS. M.W. (calculated)=4242.7 g/mol; M.W. (found)=4242.1 g/mol.

Example 46

```
Synthesis of SEQ ID NO: (49)
H-His-Ser-Gln-Gly-Thr-Phe-Thr-Ser-Asp-Leu-Ser-
Lys-Gln-Met-Glu-Glu-Glu-Arg-Val-Arg-Leu-Phe-Ile-
Glu-Trp-Leu-Lys-Asn-Gly-Gly-Pro-Ser-Ser-Gly-Ala-
Pro-Pro-Pro-Ser-NH2.
```

The synthesis and purification was carried out as described in example 2. The molecular mass of the purified peptide was confirmed by LC-MS. M.W. (calculated)=4300.8 g/mol; M.W. (found)=4300.1 g/mol.

Example 47

```
Synthesis of SEQ ID NO: (50)
H-His-Ser-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Asn-Gly-Gly-Pro-Ser-Ser-Gly-Ala-
Pro-Pro-Pro-Ser-NH—(CH2)5—OH.
```

The resin used for synthesis was purchased from Iris Biotech (5-Amino-1-pentanol 2-chlorotrityl Resin; 0.6 mmol/g; 200-400 mesh). Peptide synthesis with this resin, cleavage and purification was carried out as described in example 1. The molecular mass of the purified peptide was confirmed by LC-MS. M.W. (calculated)=4303.8 g/mol; M.W. (found)=4303.5 g/mol.

Example 48

```
Synthesis of SEQ ID NO: (51)
H-His-D-Ser-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Asn-Gly-Gly-Pro-Ser-Ser-Gly-Ala-
Pro-Pro-Pro-Lys(N-ε-(γ-Glu(N-α-
hexadecanoyl)))-NH2.
```

The synthesis and purification was carried out as described in example 3. The molecular mass of the purified peptide was confirmed by LC-MS. M.W. (calculated)=4626.2 g/mol; M.W. (found)=4625.8 g/mol.

Example 49

```
Synthesis of SEQ ID NO: (52)
H-His-Aib-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Asn-Gly-Gly-Pro-Ser-Ser-Gly-Ala-
Pro-Pro-Pro-Lys(N-ε-(γ-Glu(N-α-
hexadecanoyl)))-NH2.
```

The synthesis and purification was carried out as described in example 3. The molecular mass of the purified peptide was confirmed by LC-MS. M.W. (calculated)=4624.3 g/mol; M.W. (found)=4623.5 g/mol.

Example 50

```
Synthesis of SEQ ID NO: (53)
H-His-Ser-Gln-Gly-Thr-Phe-Thr-Ser-Asp-Leu-Ser-
Lys-Gln-Met-Glu-Glu-Glu-Ala-Ala-Arg-Leu-Phe-Ile-
Glu-Trp-Leu-Lys-Asn-Gly-Gly-Pro-Ser-Ser-Gly-Ala-
Pro-Pro-Pro-Ser-NH2.
```

The synthesis and purification was carried out as described in example 2. The molecular mass of the purified peptide was confirmed by LC-MS. M.W. (calculated)=4187.6 g/mol; M.W. (found)=4187.0 g/mol.

Example 51

```
Synthesis of SEQ ID NO: (54)
H-His-Ser-Gln-Gly-Thr-Phe-Thr-Ser-Asp-Leu-Ser-
Lys-Gln-Met-Glu-Glu-Glu-Ala-Val-Gln-Leu-Phe-Ile-
Glu-Trp-Leu-Lys-Asn-Gly-Gly-Pro-Ser-Ser-Gly-Ala-
Pro-Pro-Pro-Ser-NH2.
```

The synthesis and purification was carried out as described in example 2. The molecular mass of the purified peptide was confirmed by LC-MS. M.W. (calculated)=4187.6 g/mol; M.W. (found)=4187.0 g/mol.

Example 52

Synthesis of SEQ ID NO: (55)
H-His-Ser-Gln-Gly-Thr-Phe-Thr-Ser-Asp-Leu-Ser-
Lys-Gln-Met-Glu-Glu-Glu-Ala-Val-Arg-Asp-Phe-Ile-
Glu-Trp-Leu-Lys-Asn-Gly-Gly-Pro-Ser-Ser-Gly-Ala-
Pro-Pro-Pro-Ser-NH2.

The synthesis and purification was carried out as described in example 2. The molecular mass of the purified peptide was confirmed by LC-MS. M.W. (calculated)=4217.6 g/mol; M.W. (found)=4217.0 g/mol.

Example 53

Synthesis of SEQ ID NO: (56)
H-His-Ser-Gln-Gly-Thr-Phe-Thr-Ser-Asp-Leu-Ser-
Lys-Gln-Met-Glu-Glu-Glu-Ala-Ala-Gln-Leu-Phe-Ile-
Glu-Trp-Leu-Lys-Asn-Gly-Gly-Pro-Ser-Ser-Gly-Ala-
Pro-Pro-Pro-Ser-NH2.

The synthesis and purification was carried out as described in example 2. The molecular mass of the purified peptide was confirmed by LC-MS. M.W. (calculated)=4159.6 g/mol; M.W. (found)=4159.2 g/mol.

Example 54

Synthesis of SEQ ID NO: (57)
H-His-Ser-Gln-Gly-Thr-Phe-Thr-Ser-Asp-Leu-Ser-
Lys-Gln-Met-Glu-Glu-Glu-Ala-Ala-Arg-Asp-Phe-Ile-
Glu-Trp-Leu-Lys-Asn-Gly-Gly-Pro-Ser-Ser-Gly-Ala-
Pro-Pro-Pro-Ser-NH2.

The synthesis and purification was carried out as described in example 2. The molecular mass of the purified peptide was confirmed by LC-MS. M.W. (calculated)=4189.5 g/mol; M.W. (found)=4189.0 g/mol.

Example 55

Synthesis of SEQ ID NO: (58)
H-His-Ser-Gln-Gly-Thr-Phe-Thr-Ser-Asp-Leu-Ser-
Lys-Gln-Met-Glu-Glu-Arg-Ala-Ala-Arg-Leu-Phe-Ile-
Glu-Trp-Leu-Lys-Asn-Gly-Gly-Pro-Ser-Ser-Gly-Ala-
Pro-Pro-Pro-Ser-NH2.

The synthesis and purification was carried out as described in example 2. The molecular mass of the purified peptide was confirmed by LC-MS. M.W. (calculated)=4214.7 g/mol; M.W. (found)=4214.1 g/mol.

Example 56

Synthesis of SEQ ID NO: (59)
H-His-Aib-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Asn-Gly-Gly-Pro-Ser-Ser-Gly-Ala-
Pro-Pro-Pro-Ser-Lys(N-ε-(γ-Glu(N-α-
hexadecanoyl)))-NH2.

The synthesis and purification was carried out as described in example 2. In position 40 Fmoc-Lys(ivDde)-OH and in position 1 Boc-His(Boc)-OH were used in the solid phase synthesis protocol. The ivDde-group was cleaved from the peptide on resin according to literature (S. R. Chhabra et al., Tetrahedron Lett. 39, (1998), 1603). Hereafter Palm(γOSu)(αOtBu)Glu was coupled to the liberated amino-group. The molecular mass of the purified peptide was confirmed by LC-MS. M.W. (calculated)=4711.4 g/mol; M.W. (found)= 4710.6 g/mol.

Example 57

Synthesis of SEQ ID NO: (60)
H-His-D-Ser-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Ala-Gly-Gly-Pro-Ser-Ser-Gly-Ala-
Pro-Pro-Pro-Ser-Lys(N-ε-(γ-Glu(N-α-
hexadecanoyl)))-NH2.

The synthesis and purification was carried out as described in example 4. The molecular mass of the purified peptide was confirmed by LC-MS. M.W. (calculated)=4670.3 g/mol; M.W. (found)=4669.6 g/mol.

Example 58

Synthesis of SEQ ID NO: (61)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Asn-Gly-Gly-Pro-Ser-Ser-Gly-Ala- -continued
```
Pro-Pro-Pro-Ser-Lys(N-ε-(γ-Glu(N-α- hexadecanoyl)))-NH2.
```

The synthesis and purification was carried out as described in example 4. The molecular mass of the purified peptide was confirmed by LC-MS. M.W. (calculated)=4727.4 g/mol; M.W. (found)=4726.6 g/mol.

Example 59

```
Synthesis of SEQ ID NO: (62)
H-His-Aib-Gln-Gly-Thr-Phe-Thr-Ser-Asp-Leu-Ser-

Lys-Gln-Met-Glu-Ser-Arg-Arg-Ala-Gln-Asp-Phe-Ile-

Glu-Trp-Leu-Lys-Asn-Gly-Gly-Pro-Ser-Ser-Gly-Ala-

Pro-Pro-Pro-Ser-Lys(N-ε-(γ-Glu(N-α- hexadecanoyl)))-NH2.
```

The synthesis and purification was carried out as described in example 4. The molecular mass of the purified peptide was confirmed by LC-MS. M.W. (calculated)=4725.4 g/mol; M.W. (found)=4724.7 g/mol.

Example 60

```
Synthesis of SEQ ID NO: (63)
H-His-D-Ser-Gln-Gly-Thr-Phe-Thr-Ser-Asp-Leu-Ser- Lys-Gln-Met-Glu-Ser-Arg-Arg-Ala-Gln-Asp-Phe-Ile- Glu-Trp-Leu-Lys-Ala-Gly-Gly-Pro-Ser-Ser-Gly-Ala- Pro-Pro-Pro-Ser-Lys(N-ε-(γ-Glu(N-α- hexadecanoyl)))-NH2.
```

The synthesis and purification was carried out as described in example 4. The molecular mass of the purified peptide was confirmed by LC-MS. M.W. (calculated)=4684.3 g/mol; M.W. (found)=4683.7 g/mol.

Example 61

```
Synthesis of SEQ ID NO: (64)
H-His-D-Ser-Gln-Gly-Thr-Phe-Thr-Ser-Asp-Leu-Ser- Lys-Gln-Met-Glu-Ser-Arg-Arg-Ala-Gln-Asp-Phe-Ile- Glu-Trp-Leu-Lys-Asn-Ala-Gly-Pro-Ser-Ser-Gly-Ala- Pro-Pro-Pro-Ser-Lys(N-ε-(γ-Glu(N-α- hexadecanoyl)))-NH2.
```

The synthesis and purification was carried out as described in example 4. The molecular mass of the purified peptide was confirmed by LC-MS. M.W. (calculated)=4741.4 g/mol; M.W. (found)=4740.7 g/mol.

Example 62

```
Synthesis of SEQ ID NO: (65)
H-His-D-Ser-Gln-Gly-Thr-Phe-Thr-Ser-Asp-Leu-Ser- Lys-Gln-Met-Asp-Ser-Arg-Arg-Ala-Gln-Asp-Phe-Ile- Glu-Trp-Leu-Lys-Ser-Gly-Gly-Pro-Ser-Ser-Gly-Ala- Pro-Pro-Pro-Ser-Lys(N-ε-(γ-Glu(N-α- hexadecanoyl)))-NH2.
```

The synthesis and purification was carried out as described in example 4. The molecular mass of the purified peptide was confirmed by LC-MS. M.W. (calculated)=4686.3 g/mol; M.W. (found)=4685.7 g/mol.

Example 63

```
Synthesis of SEQ ID NO: (66)
H-His-D-Ser-Gln-Gly-Thr-Phe-Thr-Ser-Asp-Leu-Ser- Lys-Gln-Met-Asp-Ser-Arg-Arg-Ala-Gln-Asp-Phe-Ile- Glu-Trp-Leu-Lys-Lys-Gly-Gly-Pro-Ser-Ser-Gly-Ala- Pro-Pro-Pro-Ser-Lys(N-ε-(γ-Glu(N-α- hexadecanoyl)))-NH2.
```

The synthesis and purification was carried out as described in example 4. The molecular mass of the purified peptide was confirmed by LC-MS. M.W. (calculated)=4727.4 g/mol; M.W. (found)=4726.8 g/mol.

Example 64

```
Synthesis of SEQ ID NO: (67)
H-His-D-Ser-Gln-Gly-Thr-Phe-Thr-Ser-Asp-Leu-Ser- Lys-Gln-Met-Asp-Ser-Arg-Arg-Ala-Gln-Asp-Phe-Ile- Glu-Trp-Leu-Lys-Asn-Ala-Gly-Pro-Ser-Ser-Gly-Ala- Pro-Pro-Pro-Ser-Lys(N-ε-(γ-Glu(N-α- hexadecanoyl)))-NH2.
```

The synthesis and purification was carried out as described in example 4. The molecular mass of the purified peptide was confirmed by LC-MS. M.W. (calculated)=4727.4 g/mol; M.W. (found)=4726.8 g/mol.

Example 65

Synthesis of SEQ ID NO: (68)
H-His-D-Ser-Gln-Gly-Thr-Phe-Thr-Ser-Asp-Leu-Ser-Lys-Gln-Met-Asp-Ser-Arg-Arg-Ala-Gln-Asp-Phe-Ile-Glu-Trp-Leu-Lys-Asn-D-Ala-Gly-Pro-Ser-Ser-Gly-Ala-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4727.4 g/mol; M.W. (found)=4726.7 g/mol.

Example 66

Synthesis of SEQ ID NO: (69)
H-His-D-Ser-Gln-Gly-Thr-Phe-Thr-Ser-Asp-Leu-Ser-Lys-Gln-Met-Asp-Lys-Arg-Arg-Ala-Gln-Asp-Phe-Ile-Glu-Trp-Leu-Lys-Asn-Gly-Gly-Pro-Ser-Ser-Gly-Ala-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4754.4 g/mol, M.W. (found)=4753.8 g/mol.

Example 67

Synthesis of SEQ ID NO: (70)
H-His-D-Ser-Gln-Gly-Thr-Phe-Thr-Ser-Asp-Leu-Ser-Lys-Gln-Met-Asp-Glu-Arg-Arg-Ala-Lys-Asp-Phe-Ile-Glu-Trp-Leu-Lys-Asn-Gly-Gly-Pro-Ser-Ser-Gly-Ala-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4755.4 g/mol, M.W. (found)=4754.8 g/mol.

Example 68

Synthesis of SEQ ID NO: (71)
H-His-D-Ser-Gln-Gly-Thr-Phe-Thr-Ser-Asp-Leu-Ser-Lys-Gln-Met-Asp-Ser-Arg-Arg-Ala-Gln-Asp-Phe-Ile-Glu-Trp-Leu-Lys-Asn-Thr-Gly-Pro-Ser-Ser-Gly-Ala-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4757.4 g/mol; M.W. (found)=4757.0 g/mol.

Example 69

Synthesis of SEQ ID NO: (72)
H-His-D-Ser-Gln-Gly-Thr-Phe-Thr-Ser-Asp-Leu-Ser-Lys-Gln-Met-Asp-Ser-Arg-Arg-Ala-Gln-Asp-Phe-Ile-Glu-Trp-Leu-Lys-Aib-Gly-Gly-Pro-Ser-Ser-Gly-Ala-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4684.3 g/mol; M.W. (found)=4683.8 g/mol.

Example 70

Synthesis of SEQ ID NO: (73)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Aib-Gly-Gly-Pro-Ser-Ser-Gly-Ala-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4698.4 g/mol; M.W. (found)=4697.9 g/mol.

Example 71

Synthesis of SEQ ID NO: (74)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Asn-Thr-Gly-Pro-Ser-Ser-Gly-Ala-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4771.4 g/mol; M.W. (found)=4771.0 g/mol.

Example 72

Synthesis of SEQ ID NO: (75)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Arg-Gly-Gly-Pro-Ser-Ser-Gly-Ala-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4769.4 g/mol, M.W. (found)=4769.0 g/mol.

Example 73

Synthesis of SEQ ID NO: (76)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Arg-D-Ala-Gly-Pro-Ser-Ser-Gly-Ala-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4783.5 g/mol; M.W. (found)=4782.9 g/mol.

Example 74

Synthesis of SEQ ID NO: (77)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Lys-Gly-Gly-Pro-Ser-Ser-Gly-Ala-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4741.4 g/mol; M.W. (found)=4740.9 g/mol.

Example 75

Synthesis of SEQ ID NO: (78)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4700.3 g/mol; M.W. (found)=4699.8 g/mol.

Example 76

Synthesis of SEQ ID NO: (79)
H-His-D-Ser-Gln-Gly-Thr-Phe-Thr-Ser-Asp-Leu-Ser-Lys-Gln-Met-Glu-Ser-Arg-Ala-Ala-Gln-Leu-Phe-Ile-Glu-Trp-Leu-Lys-Ala-Gly-Gly-Pro-Ser-Ser-Gly-Ala-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4597.3 g/mol; M.W. (found)=4596.8 g/mol.

Example 77

Synthesis of SEQ ID NO: (80)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Aib-Gly-Gly-Pro-Ser-Ser-Gly-Ala-Pro-Pro-Pro-Lys(N-ε-(γ-Glu(N-α-hexadecanoyl)))-NH2.

The synthesis and purification was carried out as described in example 3. The molecular mass of the purified peptide was confirmed by LC-MS. M.W. (calculated)=4611.3 g/mol; M.W. (found)=4610.5 g/mol.

Example 78

Synthesis of SEQ ID NO: (81)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Aib-Gly-Gly-Pro-Ser-Ser-Gly-Ala-Pro-Pro-Pro-Lys(N-ε-(hexadecanoyl))-NH2.

The synthesis and purification was carried out as described in example 3. The molecular mass of the purified peptide was confirmed by LC-MS. M.W. (calculated)=4482.2 g/mol; M.W. (found)=4481.5 g/mol.

Example 79

Synthesis of SEQ ID NO: (82)
H-Gly-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4757.4 g/mol; M.W. (found)=4756.6 g/mol.

Example 80

Synthesis of SEQ ID NO: (83)
H-Ac-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4742.3 g/mol; M.W. (found)=4741.4 g/mol.

Example 81

Synthesis of SEQ ID NO: (84)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-Lys(N-ε-(γ-Glu(N-α-octadecanoyl)))-NH2.

The synthesis and purification was carried out as described in example 4. The molecular mass of the purified peptide was confirmed by LC-MS. M.W. (calculated)=4728.4 g/mol; M.W. (found)=4727.6 g/mol.

Example 82

Synthesis of SEQ ID NO: (85)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-Lys(N-ε-(octadecanoyl))-NH2.

The synthesis and purification was carried out as described in example 4. The molecular mass of the purified peptide was confirmed by LC-MS. M.W. (calculated)=4599.3 g/mol; M.W. (found)=4598.5 g/mol.

Example 83

Synthesis of SEQ ID NO: (86)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-Lys(N-ε-(γ-Glu(N-α-tocopheryl-succinyl)))-NH2.

The synthesis and purification was carried out as described in example 4. The molecular mass of the purified peptide was confirmed by LC-MS. M.W. (calculated)=4974.7 g/mol; M.W. (found)=4974.0 g/mol.

Example 84

Synthesis of SEQ ID NO: (87)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Ala-Gly-Gly-Pro-Ser-Ser-Gly-Ala-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4666.3 g/mol; M.W. (found)=4665.5 g/mol.

Example 85

Synthesis of SEQ ID NO: (88)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-Orn(N-δ-(γ-Glu(N-α-hexadecanoyl)))-NH2.

The synthesis and purification was carried out as described in example 4. The molecular mass of the purified peptide was confirmed by LC-MS. M.W. (calculated)=4686.3 g/mol; M.W. (found)=4685.7 g/mol.

Example 86

Synthesis of SEQ ID NO: (89)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-Dab(N-γ-(γ-Glu(N-α-hexadecanoyl)))-NH2.

The synthesis and purification was carried out as described in example 4. The molecular mass of the purified peptide was confirmed by LC-MS. M.W. (calculated)=4672.3 g/mol; M.W. (found)=4671.5 g/mol.

Example 87

Synthesis of SEQ ID NO: (90)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-Dap(N-β-(γ-Glu(N-α-hexadecanoyl)))-NH2.

The synthesis and purification was carried out as described in example 4. The molecular mass of the purified peptide was confirmed by LC-MS. M.W. (calculated)=4658.2 g/mol; M.W. (found)=4657.4 g/mol.

Example 88

Synthesis of SEQ ID NO: (91)
H-His-D-Ser-Gln-Gly-Thr-Phe-Thr-Ser-Asp-Leu-Ser-Lys-Gln-Met-Glu-Ser-Arg-Arg-Ala-Arg-Leu-Phe-Ile-Glu-Trp-Leu-Lys-Ser-Gly-Gly-Pro-Ser-Ser-Gly-Ala-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4726.4 g/mol; M.W. (found)=4725.7 g/mol.

Example 89

Synthesis of SEQ ID NO: (92)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Glu-Gly-Gly-Pro-Ser-Ser-Gly-Arg-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4827.5 g/mol; M.W. (found)=4826.8 g/mol.

Example 90

Synthesis of SEQ ID NO: (93)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-Lys(γ-Glu(N-α-aleuritolyl))-NH2.

The synthesis and purification was carried out as described in example 4. The molecular mass of the purified peptide was confirmed by LC-MS. M.W. (calculated)=4748.3 g/mol; M.W. (found)=4747.6 g/mol.

Example 91

Synthesis of SEQ ID NO: (94)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-Lys(N-α-aleuritolyl)-NH2.

The synthesis and purification was carried out as described in example 4. The molecular mass of the purified peptide was confirmed by LC-MS. M.W. (calculated)=4619.2 g/mol; M.W. (found)=4618.6 g/mol.

Example 92

Synthesis of SEQ ID NO: (95)
H-His-D-Ser-Gln-Gly-Thr-Phe-Thr-Ser-Asp-Leu-Ser-Lys-Gln-Chx-Ala-Glu-Ser-Arg-Arg-Ala-Gln-Asp-Phe-Ile-Glu-Trp-Leu-Lys-Ala-Gly-Gly-Pro-Ser-Ser-Gly-Ala-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4706.3 g/mol; M.W. (found)=4705.6 g/mol.

Example 93

Synthesis of SEQ ID NO: (96)
H-His-D-Ser-Gln-Gly-Thr-Phe-Thr-Ser-Asp-Leu-Ser-Lys-Gln-Cp-Ala-Glu-Ser-Arg-Arg-Ala-Gln-Asp-Phe-Ile-Glu-Trp-Leu-Lys-Ala-Gly-Gly-Pro-Ser-Ser-Gly-Ala-Pro-Pro-Pro-Ser-Lys(N-ε-(γ-Glu(N-α-hexadecanoyl)))-NH2.

The synthesis and purification was carried out as described in example 4. The molecular mass of the purified peptide was confirmed by LC-MS. M.W. (calculated)=4664.3 g/mol; M.W. (found)=4663.6 g/mol.

Example 94

Synthesis of SEQ ID NO: (97)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-Lys(N-ε-(γ-Glu(N-α-(γ-Glu(N-α-hexadecanoyl))))-NH2.

The synthesis and purification was carried out as described in example 4. The molecular mass of the purified peptide was confirmed by LC-MS. M.W. (calculated)=4829.4 g/mol; M.W. (found)=4828.9 g/mol.

Example 95

Synthesis of SEQ ID NO: (98)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-Lys(N-ε-(β-Ala(N-α-(β-Ala(N-α-hexadecanoyl)))))-NH2.

The synthesis and purification was carried out as described in example 4. The molecular mass of the purified peptide was confirmed by LC-MS. M.W. (calculated)=4713.4 g/mol; M.W. (found)=4712.8 g/mol.

Example 96

Synthesis of SEQ ID NO: (99)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-Lys(N-ε-(γ-aminobutyroyl(N-γ-hexadecanoyl)))-NH2.

The synthesis and purification was carried out as described in example 4. The molecular mass of the purified peptide was confirmed by LC-MS. M.W. (calculated)=4655.8 g/mol, M.W. (found)=4656.3 g/mol.

Example 97

Synthesis of SEQ ID NO: (100)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Lys(N-ε-(β-Ala(N-α-(β-Ala(N-α-hexadecanoyl)))))-NH2.

The synthesis and purification was carried out as described in example 4. The molecular mass of the purified peptide was confirmed by LC-MS. M.W. (calculated)=4626.3 g/mol; M.W. (found)=4625.8 g/mol.

Example 98

Synthesis of SEQ ID NO: (101)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Lys(N-ε-(β-Ala(N-α-hexadecanoyl)))-NH2.

The synthesis and purification was carried out as described in example 4. The molecular mass of the purified peptide was confirmed by LC-MS. M.W. (calculated)=4555.2 g/mol; M.W. (found)=4555.1 g/mol.

Example 99

Synthesis of SEQ ID NO: (102)
H-His-D-Ser-Gln-Gly-Thr-Phe-Thr-Ser-Asp-Leu-Ser-Lys-Gln-Met-Glu-Ser-Arg-Arg-Ala-Aib-Asp-Phe-Ile-Glu-Trp-Leu-Lys-Ser-Gly-Gly-Pro-Ser-Ser-Gly-Ala-

```
Pro-Pro-Pro-Ser-Lys(N-ε-(γ-Glu(N-α- hexadecanoyl)))-NH2.
```

The synthesis and purification was carried out as described in example 4. The molecular mass of the purified peptide was confirmed by LC-MS. M.W. (calculated)=4657.3 g/mol; M.W. (found)=4657.8 g/mol.

Example 100

```
Synthesis of SEQ ID NO: (103)
H-His-D-Ser-Gln-Gly-Thr-Phe-Thr-Ser-Asp-Leu-Ser- Lys-Gln-Met-Glu-Ser-Arg-Ala-Ala-Gln-Asp-Phe-Ile- Glu-Trp-Leu-Lys-Ser-Gly-Gly-Pro-Ser-Ser-Gly-Ala- Pro-Pro-Pro-Ser-Lys(N-ε-(γ-Glu(N-α- hexadecanoyl)))-NH2.
```

The synthesis and purification was carried out as described in example 4. The molecular mass of the purified peptide was confirmed by LC-MS. M.W. (calculated)=4615.2 g/mol; M.W. (found)=4614.5 g/mol.

Example 101

```
Synthesis of SEQ ID NO: (104)
H-His-D-Ser-Gln-Gly-Thr-Phe-Thr-Ser-Asp-Leu-Ser- Lys-Gln-Met-Glu-Ser-Arg-Arg-Ala-Gln-Asp-Phe-Ile- Glu-Trp-Leu-Lys-Glu-Gly-Gly-Pro-Ser-Ser-Gly-Lys- Pro-Pro-Pro-Ser-Lys(N-ε-(γ-Glu(N-α- hexadecanoyl)))-NH2.
```

The synthesis and purification was carried out as described in example 4. The molecular mass of the purified peptide was confirmed by LC-MS. M.W. (calculated)=4799.4 g/mol; M.W. (found)=4799.0 g/mol.

Example 102

```
Synthesis of SEQ ID NO: (105)
H-His-D-Ser-Gln-Gly-Thr-Phe-Thr-Ser-Asp-Leu-Ser- Lys-Gln-Met-Glu-Ser-Arg-Arg-Ala-Gln-Asp-Phe-Ile- Glu-Trp-Leu-Lys-Ser-Gly-Gly-Pro-Ser-Ser-Gly-Ala- Pro-Pro-Pro-Ser-Lys(N-ε-acetyl)-NH2.
```

The synthesis and purification was carried out as described in example 4. The molecular mass of the purified peptide was confirmed by LC-MS. M.W. (calculated)=4374.8 g/mol; M.W. (found)=4374.3 g/mol.

Example 103

```
Synthesis of SEQ ID NO: (106)
H-His-D-Ser-Gln-Gly-Thr-Phe-Thr-Ser-Asp-Leu-Ser- Lys-Gln-Met-Glu-Ser-Arg-Arg-Ala-Gln-Asp-Phe-Ile- Glu-Trp-Leu-Lys-Ser-Gly-Gly-Pro-Ser-Ser-Gly-Ala- Pro-Pro-Pro-Ser-Lys(N-ε-(γ-Glu(N-α- propionyl)))-NH2.
```

The synthesis and purification was carried out as described in example 4. The molecular mass of the purified peptide was confirmed by LC-MS. M.W. (calculated)=4532.0 g/mol; M.W. (found)=4531.4 g/mol.

Example 104

```
Synthesis of SEQ ID NO: (107)
H-His-D-Ser-Gln-Gly-Thr-Phe-Thr-Ser-Asp-Leu-Ser- Lys-Gln-Met-Glu-Ser-Arg-Arg-Ala-Gln-Asp-Phe-Ile- Glu-Trp-Leu-Lys-Ser-Gly-Gly-Pro-Ser-Ser-Gly-Ala- Pro-Pro-Pro-Ser-Lys(N-ε-(6-[(4,4-diphenylcyclohexyloxy)-hydroxy-phosphoryloxy]-hexanoyl)-

NH2.
```

The synthesis and purification was carried out as described in example 4. The molecular mass of the purified peptide was confirmed by LC-MS. M.W. (calculated)=4761.3 g/mol; M.W. (found)=4760.6 g/mol.

Likewise, the following compounds were synthesized:

Example 105

```
Synthesis of SEQ ID NO: (108)
H-His-D-Ser-Gln-Gly-Thr-Phe-Thr-Ser-Asp-Leu-Ser- Lys-Gln-Met-Glu-Glu-Glu-Ala-Ala-Gln-Asp-Phe-Ile- Glu-Trp-Leu-Lys-Ala-Gly-Gly-Pro-Ser-Ser-Gly-Ala- Pro-Pro-Pro-Ser-Lys(N-ε-(γ-Glu(N-α- hexadecanoyl)))-NH2.
```

Example 106

```
Synthesis of SEQ ID NO: (109)
H-His-D-Ser-Gln-Gly-Thr-Phe-Thr-Ser-Asp-Leu-Ser-
Lys-Gln-Met-Glu-Ser-Glu-Ala-Ala-Gln-Asp-Phe-Ile-
Glu-Trp-Leu-Lys-Ala-Gly-Gly-Pro-Ser-Ser-Gly-Ala-
Pro-Pro-Pro-Ser-Lys(N-ε-(γ-Glu(N-α-
hexadecanoyl)))-NH2.
```

The molecular mass of the purified peptide was confirmed by LC-MS. M.W. (calculated)=4572.1 g/mol; M.W. (found)=4571.2 g/mol.

Example 107

```
Synthesis of SEQ ID NO: (110)
H-His-D-Ser-Gln-Gly-Thr-Phe-Thr-Ser-Asp-Leu-Ser-
Lys-Gln-Met-Glu-Glu-Glu-Ala-Ala-Lys-Asp-Phe-Ile-
Glu-Trp-Leu-Lys-Ala-Gly-Gly-Pro-Ser-Ser-Gly-Ala-
Pro-Pro-Pro-Ser-Lys(N-ε-(γ-Glu(N-α-
hexadecanoyl)))-NH2.
```

The molecular mass of the purified peptide was confirmed by LC-MS. M.W. (calculated)=4614.2 g/mol; M.W. (found)=4614.0 g/mol.

Example 108

```
Synthesis of SEQ ID NO: (111)
H-His-D-Ser-Gln-Gly-Thr-Phe-Thr-Ser-Asp-Leu-Ser-
Lys-Gln-Met-Glu-Ser-Aib-Ala-Ala-Gln-Asp-Phe-Ile-
Glu-Trp-Leu-Lys-Ala-Gly-Gly-Pro-Ser-Ser-Gly-Ala-
Pro-Pro-Pro-Ser-Lys(N-ε-(γ-Glu(N-α-
hexadecanoyl)))-NH2.
```

The molecular mass of the purified peptide was confirmed by LC-MS. M.W. (calculated)=4528.1 g/mol; M.W. (found)=4527.6 g/mol.

Example 109

```
Synthesis of SEQ ID NO: (112)
H-His-D-Ser-Gln-Gly-Thr-Phe-Thr-Ser-Asp-Leu-Ser-
Lys-Gln-Met-Glu-Ser-Aib-Ala-Ala-Gln-Leu-Phe-Ile-
Glu-Trp-Leu-Lys-Ala-Gly-Gly-Pro-Ser-Ser-Gly-Ala-
Pro-Pro-Pro-Ser-Lys(N-ε-(γ-Glu(N-α-
hexadecanoyl)))-NH2.
```

The molecular mass of the purified peptide was confirmed by LC-MS. M.W. (calculated)=4526.2 g/mol; M.W. (found)=4525.6 g/mol.

Example 110

```
Synthesis of SEQ ID NO: (113)
H-His-D-Ser-Gln-Gly-Thr-Phe-Thr-Ser-Asp-Leu-Ser-
Lys-Gln-Met-Glu-Glu-Glu-Ala-Ala-Lys-Leu-Phe-Ile-
Glu-Trp-Leu-Lys-Ala-Gly-Gly-Pro-Ser-Ser-Gly-Ala-
Pro-Pro-Pro-Ser-Lys(N-ε-(γ-Glu(N-α-
hexadecanoyl)))-NH2.
```

The molecular mass of the purified peptide was confirmed by LC-MS. M.W. (calculated)=4612.3 g/mol; M.W. (found)=4611.6 g/mol.

Example 111

```
Synthesis of SEQ ID NO: (114)
H-His-D-Ser-Gln-Gly-Thr-Phe-Thr-Ser-Asp-Leu-Ser-
Lys-Gln-Met-Glu-Ser-Glu-Ala-Ala-Gln-Leu-Phe-Ile-
Glu-Trp-Leu-Lys-Ala-Gly-Gly-Pro-Ser-Ser-Gly-Ala-
Pro-Pro-Pro-Ser-Lys(N-ε-(γ-Glu(N-α-
hexadecanoyl)))-NH2.
```

The molecular mass of the purified peptide was confirmed by LC-MS. M.W. (calculated)=4570.2 g/mol; M.W. (found)=4569.5 g/mol.

Example 112

```
Synthesis of SEQ ID NO: (115)
H-His-D-Ser-Gln-Gly-Thr-Phe-Thr-Ser-Asp-Leu-Ser-
Lys-Gln-Met-Glu-Glu-Glu-Ala-Ala-Aib-Asp-Phe-Ile-
Glu-Trp-Leu-Lys-Ala-Gly-Gly-Pro-Ser-Ser-Gly-Ala-
Pro-Pro-Pro-Ser-Lys(N-ε-(γ-Glu(N-α-
hexadecanoyl)))-NH2.
```

The molecular mass of the purified peptide was confirmed by LC-MS. M.W. (calculated)=4571.2 g/mol; M.W. (found)=4569.5 g/mol.

In an analogous way, the following peptides can be synthesized:

Example 113

SEQ ID NO: (116)
H-His-Ser-N-Me-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-Lys(N-ε-(γ-Glu(N-α-hexadecanoyl)))-NH2.

Example 114

SEQ ID NO: (117)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Lys(N-ε-(γ-Glu(N-α-octadecanoyl)))-NH2.

Example 115

SEQ ID NO: (118)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Lys(N-ε-(γ-Glu(N-α-tocopheryl-succinyl)))-NH2.

Example 116

SEQ ID NO: (119)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Lys(N-ε-(γ-Glu(N-α-aleuritolyl)))-NH2.

Example 117

SEQ ID NO: (120)
H-His-D-Ser-Gln-Gly-Thr-Phe-Thr-Ser-Asp-Leu-Ser-Lys-Gln-Cb-Ala-Glu-Ser-Arg-Arg-Ala-Gln-Asp-Phe-Ile-Glu-Trp-Leu-Lys-Ala-Gly-Gly-Pro-Ser-Ser-Gly-Ala-Pro-Pro-Pro-Ser-Lys(N-ε-(γ-Glu(N-α-hexadecanoyl)))-NH2.

Example 118

SEQ ID NO: (121)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Lys(N-ε-(γ-Glu(N-α-(γ-Glu(N-α-hexadecanoyl))))-NH2.

Example 119

SEQ ID NO: (122)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ala-Gly-Gly-Pro-Ser-Ser-Gly-Ala-Pro-Pro-Pro-Ser-NH2.

Example 120

SEQ ID NO: (123)
H-His-D-Ser-Gln-Gly-Thr-Phe-Thr-Ser-Asp-Leu-Ser-Lys-Gln-Met-Glu-Ser-Arg-Arg-Ala-Aib-Asp-Phe-Ile-Glu-Trp-Leu-Lys-Ala-Gly-Gly-Pro-Ser-Ser-Gly-Ala-Pro-Pro-Pro-Ser-NH2.

Example 121

SEQ ID NO: (124)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Lys(N-ε-(γ-aminobutyroyl(N-γ-hexadecanoyl))-NH2.

Example 122

SEQ ID NO: (125)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-

-continued

Glu-Trp-Leu-Lys-Ser-Gly-Gly-Pro-Ser-Ser-Gly-Ala-

Pro-Pro-Pro-Ser-Lys(N-ε-(γ-aminobutyroyl(N-

γ-hexadecanoyl))-NH2.

Example 123

SEQ ID NO: (126)
H-His-D-Ser-Gln-Gly-Thr-Phe-Thr-Ser-Asp-Leu-Ser-

Lys-Gln-Met-Glu-Ser-Arg-Arg-Ala-Gln-Asp-Phe-Ile-

Glu-Trp-Leu-Lys-Ser-Gly-Gly-Pro-Ser-Ser-Gly-Ala-

Pro-Pro-Pro-Lys(N-ε-(γ-Glu(N-α- cholyl)))-NH2.

Example 124

SEQ ID NO: (127)
H-His-D-Ser-Gln-Gly-Thr-Phe-Thr-Ser-Asp-Leu-Ser-

Lys-Gln-Met-Glu-Ser-Arg-Arg-Ala-Gln-Asp-Phe-Ile-

Glu-Trp-Leu-Lys-Ser-Gly-Gly-Pro-Ser-Ser-Gly-Ala-

Pro-Pro-Pro-Lys(N-ε-(γ-Glu(N-α- lithocholyl)))-NH2.

Example 125

SEQ ID NO: (128)
H-His-D-Ser-Gln-Gly-Thr-Phe-Thr-Ser-Asp-Leu-Ser-

Lys-Gln-Met-Glu-Ser-Arg-Arg-Ala-Gln-Asp-Phe-Ile-

Glu-Trp-Leu-Lys-Ser-Gly-Gly-Pro-Ser-Ser-Gly-Ala-

Pro-Pro-Pro-Lys(N-ε-(γ-Glu(N-α- linoleoyl)))-NH2.

Example 126

SEQ ID NO: (129)
H-His-D-Ser-Gln-Gly-Thr-Phe-Thr-Ser-Asp-Leu-Ser-

Lys-Gln-Met-Glu-Ser-Arg-Arg-Ala-Gln-Asp-Phe-Ile-

Glu-Trp-Leu-Lys-Ser-Gly-Gly-Pro-Ser-Ser-Gly-Ala-

Pro-Pro-Pro-Lys(N-ε-(γ-Glu(N-α-(4- dodecyclobenzoyl))))-NH2.

Example 127

SEQ ID NO: (130)
H-His-D-Ser-Gln-Gly-Thr-Phe-Thr-Ser-Asp-Leu-Ser-

Lys-Gln-Met-Glu-Ser-Arg-Arg-Ala-Gln-Asp-Phe-Ile-

Glu-Trp-Leu-Lys-Ser-Gly-Gly-Pro-Ser-Ser-Gly-Ala-

Pro-Pro-Pro-Lys(N-ε-(γ-Glu(N-α- heneicosanoyl)))-NH2.

Example 128

SEQ ID NO: (131)
H-His-D-Ser-Gln-Gly-Thr-Phe-Thr-Ser-Asp-Leu-Ser-

Lys-Gln-Met-Glu-Ser-Arg-Arg-Ala-Gln-Asp-Phe-Ile-

Glu-Trp-Leu-Lys-Ser-Gly-Gly-Pro-Ser-Ser-Gly-Ala-

Pro-Pro-Pro-Lys(N-ε-(γ-Glu(N-α- behenoyl)))-NH2.

Example 129

SEQ ID NO: (132)
H-His-D-Ser-Gln-Gly-Thr-Phe-Thr-Ser-Asp-Leu-Ser-

Lys-Gln-Met-Glu-Ser-Arg-Arg-Ala-Gln-Asp-Phe-Ile-

Glu-Trp-Leu-Lys-Ser-Gly-Gly-Pro-Ser-Ser-Gly-Ala-

Pro-Pro-Pro-Lys(N-ε-(γ-Glu(N-α-(cis-1- nonadecanoyl))))-NH2.

Example 130

SEQ ID NO: (133)
H-His-D-Ser-Gln-Gly-Thr-Phe-Thr-Ser-Asp-Leu-Ser-

Lys-Gln-Met-Glu-Ser-Arg-Arg-Ala-Gln-Asp-Phe-Ile-

Glu-Trp-Leu-Lys-Ser-Gly-Gly-Pro-Ser-Ser-Gly-Ala-

Pro-Pro-Pro-Lys(N-ε-(γ-Glu(N-α-(4-n- decycloxybenzoyl))))-NH2.

Example 131

SEQ ID NO: (134)
H-His-D-Ser-Gln-Gly-Thr-Phe-Thr-Ser-Asp-Leu-Ser-

Lys-Gln-Met-Glu-Ser-Arg-Arg-Ala-Gln-Asp-Phe-Ile-

Glu-Trp-Leu-Lys-Ser-Gly-Gly-Pro-Ser-Ser-Gly-Ala-

Pro-Pro-Pro-Lys(N-ε-(γ-Glu(N-α-(4'- octyloxy-biphenyl-4-carbonyl))))-NH2.

Example 132

```
                                    SEQ ID NO: (135)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Ser-Gly-Gly-Pro-Ser-Ser-Gly-Ala-
Pro-Pro-Pro-Lys(N-ε-(γ-Glu(N-α-(12-
phenyl-dodecanoyl))))-NH2.
```

Example 133

```
                                    SEQ ID NO: (136)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Ser-Gly-Gly-Pro-Ser-Ser-Gly-Ala-
Pro-Pro-Pro-Ser-Lys(N-ε-(γ-Glu(N-α-
cholyl)))-NH2.
```

Example 134

```
                                    SEQ ID NO: (137)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Ser-Gly-Gly-Pro-Ser-Ser-Gly-Ala-
Pro-Pro-Pro-Ser-Lys(N-ε-(γ-Glu(N-α-
lithocholyl)))-NH2.
```

Example 135

```
                                    SEQ ID NO: (138)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Ser-Gly-Gly-Pro-Ser-Ser-Gly-Ala-
Pro-Pro-Pro-Ser-Lys(N-ε-(γ-Glu(N-α-
linoleoyl)))-NH2.
```

Example 136

```
                                    SEQ ID NO: (139)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Ser-Gly-Gly-Pro-Ser-Ser-Gly-Ala-
Pro-Pro-Pro-Ser-Lys(N-ε-(γ-Glu(N-α-(4-
dodecyclobenzoyl))))-NH2.
```

Example 137

```
                                    SEQ ID NO: (140)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Ser-Gly-Gly-Pro-Ser-Ser-Gly-Ala-
Pro-Pro-Pro-Ser-Lys(N-ε-(γ-Glu(N-α-
heneicosanoyl)))-NH2.
```

Example 138

```
                                    SEQ ID NO: (141)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Ser-Gly-Gly-Pro-Ser-Ser-Gly-Ala-
Pro-Pro-Pro-Ser-Lys(N-ε-(γ-Glu(N-α-
behenoyl)))-NH2.
```

Example 139

```
                                    SEQ ID NO: (142)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Ser-Gly-Gly-Pro-Ser-Ser-Gly-Ala-
Pro-Pro-Pro-Ser-Lys(N-ε-(γ-Glu(N-α-
(cis-1-nonadecanoyl))))-NH2.
```

Example 140

```
                                    SEQ ID NO: (143)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Ser-Gly-Gly-Pro-Ser-Ser-Gly-Ala-
Pro-Pro-Pro-Ser-Lys(N-ε-(γ-Glu(N-α-
(4-n-decycloxybenzoyl))))-NH2.
```

Example 141

```
                                    SEQ ID NO: (144)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Ser-Gly-Gly-Pro-Ser-Ser-Gly-Ala-
Pro-Pro-Pro-Ser-Lys(N-ε-(γ-Glu(N-α-
(4'-octyloxy-biphenyl-4-carbonyl))))-NH2.
```

Example 142

SEQ ID NO: (145)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Ser-Gly-Gly-Pro-Ser-Ser-Gly-Ala-
Pro-Pro-Pro-Ser-Lys(N-ε-(γ-Glu(N-α-
(12-phenyl-dodecanoyl))))-NH2.

Example 143

SEQ ID NO: (146)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Ser-Gly-Gly-Pro-Ser-Ser-Gly-Ala-
Pro-Pro-Pro-Ser-Lys(N-ε-(β-Ala(N-α-
hexadecanoyl)))-NH2.

Example 144

SEQ ID NO: (147)
H-His-Ser-Gln-Gly-Thr-Phe-Thr-Ser-Asp-Leu-Ser-
Lys-Gln-Met-Asp-Ser-Lys-Lys-Ala-Gln-Glu-Phe-Ile-
Glu-Trp-Leu-Lys-Asn-Gly-Gly-Pro-Ser-Ser-Gly-Ala-
Pro-Pro-Pro-Ser-NH2.

Example 145

SEQ ID NO: (148)
H-Gly-His-Ser-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Asn-Gly-Gly-Pro-Ser-Ser-Gly-Ala-
Pro-Pro-Pro-Ser-NH2.

Example 146

SEQ ID NO: (149)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Ser-Gly-Gly-Pro-Ser-Ser-Gly-Ala-
Pro-Pro-Pro-Ser-Lys(N-ε-(PEG40kDa))-NH2.

PEG40 kDa refers to a polyethylene glycol with a molecular mass of about 40 kDa.

Example 147

SEQ ID NO: (150)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Ser-Gly-Gly-Pro-Ser-Ser-Gly-Ala-
Pro-Pro-Pro-Ser-Cys(PEG40kDa)-NH2.

PEG40 kDa refers to a polyethylene glycol with a molecular mass of about 40 kDa.

Example 148

SEQ ID NO: (151)
H-His-D-Ser-Gln-Gly-Thr-Phe-Thr-Ser-Asp-Leu-Ser-
Lys-Gln-Met-Glu-Ser-Arg-Arg-Ala-Gln-Glu-Phe-Ile-
Glu-Trp-Leu-Lys-Ser-Gly-Gly-Pro-Ser-Ser-Gly-Ala-
Pro-Pro-Pro-Ser-Lys(N-ε-(γ-Glu(N-α-
hexadecanoyl)))-NH2.

Example 149

SEQ ID NO: (152)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Ser-Gly-Gly-Pro-Ser-Ser-Gly-Ala-
Pro-Pro-Pro-Ser-Lys(N-ε-(hexadecanoyl))-NH2

Example 150

SEQ ID NO: (153)
H-His-Aib-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Asn-Gly-Gly-Pro-Ser-Ser-Gly-Ala-
Pro-Pro-Pro-Ser-Lys-NH2

Example 151

SEQ ID NO: (154)
H-His-D-Ser-Gln-Gly-Thr-Phe-Thr-Ser-Asp-Leu-Ser-
Lys-Gln-Met-Asp-Ser-Arg-Arg-Ala-Gln-Asp-Phe-Ile-

-continued

Glu-Trp-Leu-Lys-Ala-Gly-Gly-Pro-Ser-Ser-Gly-Ala-

Pro-Pro-Pro-Ser-Lys-NH2

Example 152

SEQ ID NO: (155)
H-His-D-Ser-Gln-Gly-Thr-Phe-Thr-Ser-Asp-Leu-Ser-

Lys-Gln-Met-Glu-Ser-Arg-Arg-Ala-Gln-Asp-Phe-Ile-

Glu-Trp-Leu-Lys-Asn-Gly-Gly-Pro-Ser-Ser-Gly-Ala-

Pro-Pro-Pro-Ser-Lys-NH2

Example 153

SEQ ID NO: (156)
H-His-Aib-Gln-Gly-Thr-Phe-Thr-Ser-Asp-Leu-Ser-

Lys-Gln-Met-Glu-Ser-Arg-Arg-Ala-Gln-Asp-Phe-Ile-

Glu-Trp-Leu-Lys-Asn-Gly-Gly-Pro-Ser-Ser-Gly-Ala-

Pro-Pro-Pro-Ser-Lys-NH2

Example 154

SEQ ID NO: (157)
H-His-D-Ser-Gln-Gly-Thr-Phe-Thr-Ser-Asp-Leu-Ser-

Lys-Gln-Met-Glu-Ser-Arg-Arg-Ala-Gln-Asp-Phe-Ile-

Glu-Trp-Leu-Lys-Ala-Gly-Gly-Pro-Ser-Ser-Gly-Ala-

Pro-Pro-Pro-Ser-Lys-NH2

Example 155

SEQ ID NO: (158)
H-His-D-Ser-Gln-Gly-Thr-Phe-Thr-Ser-Asp-Leu-Ser-

Lys-Gln-Met-Glu-Ser-Arg-Arg-Ala-Gln-Asp-Phe-Ile-

Glu-Trp-Leu-Lys-Asn-Ala-Gly-Pro-Ser-Ser-Gly-Ala-

Pro-Pro-Pro-Ser-Lys-NH2

Example 156

SEQ ID NO: (159)
H-His-D-Ser-Gln-Gly-Thr-Phe-Thr-Ser-Asp-Leu-Ser-

Lys-Gln-Met-Asp-Ser-Arg-Arg-Ala-Gln-Asp-Phe-Ile-

Glu-Trp-Leu-Lys-Ser-Gly-Gly-Pro-Ser-Ser-Gly-Ala-

Pro-Pro-Pro-Ser-Lys-NH2

Example 157

SEQ ID NO: (160)
H-His-D-Ser-Gln-Gly-Thr-Phe-Thr-Ser-Asp-Leu-Ser-

Lys-Gln-Met-Asp-Ser-Arg-Arg-Ala-Gln-Asp-Phe-Ile-

Glu-Trp-Leu-Lys-Lys-Gly-Gly-Pro-Ser-Ser-Gly-Ala-

Pro-Pro-Pro-Ser-Lys-NH2

Example 158

SEQ ID NO: (161)
H-His-D-Ser-Gln-Gly-Thr-Phe-Thr-Ser-Asp-Leu-Ser-

Lys-Gln-Met-Asp-Ser-Arg-Arg-Ala-Gln-Asp-Phe-Ile-

Glu-Trp-Leu-Lys-Asn-Ala-Gly-Pro-Ser-Ser-Gly-Ala-

Pro-Pro-Pro-Ser-Lys-NH2

Example 159

SEQ ID NO: (162)
H-His-D-Ser-Gln-Gly-Thr-Phe-Thr-Ser-Asp-Leu-Ser-

Lys-Gln-Met-Asp-Ser-Arg-Arg-Ala-Gln-Asp-Phe-Ile-

Glu-Trp-Leu-Lys-Asn-D-Ala-Gly-Pro-Ser-Ser-Gly-Ala-

Pro-Pro-Pro-Ser-Lys-NH2

Example 160

SEQ ID NO: (163)
H-His-D-Ser-Gln-Gly-Thr-Phe-Thr-Ser-Asp-Leu-Ser-

Lys-Gln-Met-Asp-Lys-Arg-Arg-Ala-Gln-Asp-Phe-Ile-

Glu-Trp-Leu-Lys-Asn-Gly-Gly-Pro-Ser-Ser-Gly-Ala-

Pro-Pro-Pro-Ser-Lys-NH2

Example 161

SEQ ID NO: (164)
H-His-D-Ser-Gln-Gly-Thr-Phe-Thr-Ser-Asp-Leu-Ser-

Lys-Gln-Met-Asp-Glu-Arg-Arg-Ala-Lys-Asp-Phe-Ile-

Glu-Trp-Leu-Lys-Asn-Gly-Gly-Pro-Ser-Ser-Gly-Ala-

Pro-Pro-Pro-Ser-Lys-NH2

Example 162

```
                                         SEQ ID NO: (165)
H-His-D-Ser-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Asn-Thr-Gly-Pro-Ser-Ser-Gly-Ala-
Pro-Pro-Pro-Ser-Lys-NH2
```

Example 163

```
                                         SEQ ID NO: (166)
H-His-D-Ser-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Aib-Gly-Gly-Pro-Ser-Ser-Gly-Ala-
Pro-Pro-Pro-Ser-Lys-NH2
```

Example 164

```
                                         SEQ ID NO: (167)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Aib-Gly-Gly-Pro-Ser-Ser-Gly-Ala-
Pro-Pro-Pro-Ser-Lys-NH2
```

Example 165

```
                                         SEQ ID NO: (168)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Asn-Thr-Gly-Pro-Ser-Ser-Gly-Ala-
Pro-Pro-Pro-Ser-Lys-NH2
```

Example 166

```
                                         SEQ ID NO: (169)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Arg-Gly-Gly-Pro-Ser-Ser-Gly-Ala-
Pro-Pro-Pro-Ser-Lys-NH2
```

Example 167

```
                                         SEQ ID NO: (170)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Arg-D-Ala-Gly-Pro-Ser-Ser-Gly-Ala-
Pro-Pro-Pro-Ser-Lys-NH2
```

Example 168

```
                                         SEQ ID NO: (171)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Lys-Gly-Gly-Pro-Ser-Ser-Gly-Ala-
Pro-Pro-Pro-Ser-Lys-NH2
```

Example 169

```
                                         SEQ ID NO: (172)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Ser-Gly-Gly-Pro-Ser-Ser-Gly-Ala-
Pro-Pro-Pro-Ser-Lys-NH2
```

Example 170

```
                                         SEQ ID NO: (173)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Asn-Gly-Gly-Pro-Ser-Ser-Gly-Ala-
Pro-Pro-Pro-Ser-NH2
```

Example 171

```
                                         SEQ ID NO: (174)
H-His-Aib-Gln-Gly-Thr-Phe-Thr-Ser-Asp-Leu-Ser-Lys-
Gln-Met-Glu-Ser-Arg-Arg-Ala-Gln-Asp-Phe-Ile-Glu-
Trp-Leu-Lys-Asn-Gly-Gly-Pro-Ser-Ser-Gly-Ala-Pro-
Pro-Pro-Ser-NH2
```

Example 172

```
                                         SEQ ID NO: (175)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Ala-Gly-Gly-Pro-Ser-Ser-Gly-Ala-
Pro-Pro-Pro-Ser-NH2
```

Example 173

SEQ ID NO: (176)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Asn-Ala-Gly-Pro-Ser-Ser-Gly-Ala-
Pro-Pro-Pro-Ser-NH2

Example 174

SEQ ID NO: (177)
H-His-D-Ser-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Ser-Gly-Gly-Pro-Ser-Ser-Gly-Ala-
Pro-Pro-Pro-Ser-NH2

Example 175

SEQ ID NO: (178)
H-His-D-Ser-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Asn-Ala-Gly-Pro-Ser-Ser-Gly-Ala-
Pro-Pro-Pro-Ser-NH2

Example 176

SEQ ID NO: (179)
H-His-D-Ser-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Asn-D-Ala-Gly-Pro-Ser-Ser-Gly-Ala-
Pro-Pro-Pro-Ser-NH2

Example 177

SEQ ID NO: (180)
H-His-D-Ser-Gln-Gly-Thr-Phe-Thr-Ser-Asp-Leu-Ser-
Lys-Gln-Met-Asp-Lys-Arg-Arg-Ala-Gln-Asp-Phe-Ile-
Glu-Trp-Leu-Lys-Asn-Gly-Gly-Pro-Ser-Ser-Gly-Ala-
Pro-Pro-Pro-Ser-NH2

Example 178

SEQ ID NO: (181)
H-His-D-Ser-Gln-Gly-Thr-Phe-Thr-Ser-Asp-Leu-Ser-
Lys-Gln-Met-Asp-Glu-Arg-Arg-Ala-Lys-Asp-Phe-Ile-
Glu-Trp-Leu-Lys-Asn-Gly-Gly-Pro-Ser-Ser-Gly-Ala-
Pro-Pro-Pro-Ser-NH2

Example 179

SEQ ID NO: (182)
H-His-D-Ser-Gln-Gly-Thr-Phe-Thr-Ser-Asp-Leu-Ser-
Lys-Gln-Met-Asp-Ser-Arg-Arg-Ala-Gln-Asp-Phe-Ile-
Glu-Trp-Leu-Lys-Asn-Thr-Gly-Pro-Ser-Ser-Gly-Ala-
Pro-Pro-Pro-Ser-NH2

Example 180

SEQ ID NO: (183)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Aib-Gly-Gly-Pro-Ser-Ser-Gly-Ala-
Pro-Pro-Pro-Ser-NH2

Example 181

SEQ ID NO: (184)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Asn-Thr-Gly-Pro-Ser-Ser-Gly-Ala-
Pro-Pro-Pro-Ser-NH2

Example 182

SEQ ID NO: (185)
H-His-D-Ser-Gln-Gly-Thr-Phe-Thr-Ser-Asp-Leu-Ser-
Lys-Gln-Met-Glu-Ser-Arg-Arg-Ala-Gln-Asp-Phe-Ile-
Glu-Trp-Leu-Lys-Arg-Gly-Gly-Pro-Ser-Ser-Gly-Ala-
Pro-Pro-Pro-Ser-NH2

Example 183

SEQ ID NO: (186)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Arg-D-Ala-Gly-Pro-Ser-Ser-Gly-Ala-Pro-Pro-Pro-Ser-NH2

Example 184

SEQ ID NO: (187)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Lys-Gly-Gly-Pro-Ser-Ser-Gly-Ala-Pro-Pro-Pro-Ser-NH2

Example 185

SEQ ID NO: (188)
H-His-D-Ser-Gln-Gly-Thr-Phe-Thr-Ser-Asp-Leu-Ser-Lys-Gln-Met-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-NH2

Example 186

SEQ ID NO: (189)
H-His-Aib-Gln-Gly-Thr-Phe-Thr-Ser-Asp-Leu-Ser-Lys-Gln-Nle-Asp-Ser-Arg-Arg-Ala-Gln-Asp-Phe-Ile-Glu-Trp-Leu-Lys-Asn-Gly-Gly-Pro-Ser-Ser-Gly-Ala-Pro-Pro-Pro-Ser-Lys-NH2

Example 187

SEQ ID NO: (190)
H-His-D-Ser-Gln-Gly-Thr-Phe-Thr-Ser-Asp-Leu-Ser-Lys-Gln-Nle-Asp-Ser-Arg-Arg-Ala-Gln-Asp-Phe-Ile-Glu-Trp-Leu-Lys-Ala-Gly-Gly-Pro-Ser-Ser-Gly-Ala-Pro-Pro-Pro-Ser-Lys-NH2

Example 188

SEQ ID NO: (191)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Asn-Gly-Gly-Pro-Ser-Ser-Gly-Ala-Pro-Pro-Pro-Ser-Lys-NH2

Example 189

SEQ ID NO: (192)
H-His-Aib-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Asn-Gly-Gly-Pro-Ser-Ser-Gly-Ala-Pro-Pro-Pro-Ser-Lys-NH2

Example 190

SEQ ID NO: (193)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Ala-Gly-Gly-Pro-Ser-Ser-Gly-Ala-Pro-Pro-Pro-Ser-Lys-NH2

Example 191

SEQ ID NO: (194)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Asn-Ala-Gly-Pro-Ser-Ser-Gly-Ala-Pro-Pro-Pro-Ser-Lys-NH2

Example 192

SEQ ID NO: (195)
H-His-D-Ser-Gln-Gly-Thr-Phe-Thr-Ser-Asp-Leu-Ser-Lys-Gln-Nle-Asp-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-Lys-NH2

Example 193

SEQ ID NO: (196)
H-His-D-Ser-Gln-Gly-Thr-Phe-Thr-Ser-Asp-Leu-Ser-Lys-Gln-Nle-Asp-Ser-Arg-Arg-Ala-Gln-Asp-Phe-Ile-Glu-Trp-Leu-Lys-Lys-Gly-Gly-Pro-Ser-Ser-Gly-Ala-Pro-Pro-Pro-Ser-Lys-NH2

Example 194

SEQ ID NO: (197)
H-His-D-Ser-Gln-Gly-Thr-Phe-Thr-Ser-Asp-Leu-Ser-Lys-Gln-Nle-Asp-Ser-Arg-Arg-Ala-Gln-Asp-Phe-Ile-Glu-Trp-Leu-Lys-Asn-Ala-Gly-Pro-Ser-Ser-Gly-Ala-Pro-Pro-Pro-Ser-Lys-NH2

Example 195

SEQ ID NO: (198)
H-His-D-Ser-Gln-Gly-Thr-Phe-Thr-Ser-Asp-Leu-Ser-Lys-Gln-Nle-Asp-Ser-Arg-Arg-Ala-Gln-Asp-Phe-Ile-Glu-Trp-Leu-Lys-Asn-D-Ala-Gly-Pro-Ser-Ser-Gly-Ala-Pro-Pro-Pro-Ser-Lys-NH2

Example 196

SEQ ID NO: (199)
H-His-D-Ser-Gln-Gly-Thr-Phe-Thr-Ser-Asp-Leu-Ser-Lys-Gln-Nle-Asp-Lys-Arg-Arg-Ala-Gln-Asp-Phe-Ile-Glu-Trp-Leu-Lys-Asn-Gly-Gly-Pro-Ser-Ser-Gly-Ala-Pro-Pro-Pro-Ser-Lys-NH2

Example 197

SEQ ID NO: (200)
H-His-D-Ser-Gln-Gly-Thr-Phe-Thr-Ser-Asp-Leu-Ser-Lys-Gln-Nle-Asp-Glu-Arg-Arg-Ala-Lys-Asp-Phe-Ile-Glu-Trp-Leu-Lys-Asn-Gly-Gly-Pro-Ser-Ser-Gly-Ala-Pro-Pro-Pro-Ser-Lys-NH2

Example 198

SEQ ID NO: (201)
H-His-D-Ser-Gln-Gly-Thr-Phe-Thr-Ser-Asp-Leu-Ser-Lys-Gln-Nle-Asp-Ser-Arg-Arg-Ala-Gln-Asp-Phe-Ile-Glu-Trp-Leu-Lys-Asn-Thr-Gly-Pro-Ser-Ser-Gly-Ala-Pro-Pro-Pro-Ser-Lys-NH2

Example 199

SEQ ID NO: (202)
H-His-D-Ser-Gln-Gly-Thr-Phe-Thr-Ser-Asp-Leu-Ser-Lys-Gln-Nle-Asp-Ser-Arg-Arg-Ala-Gln-Asp-Phe-Ile-Glu-Trp-Leu-Lys-Aib-Gly-Gly-Pro-Ser-Ser-Gly-Ala-Pro-Pro-Pro-Ser-Lys-NH2

Example 200

SEQ ID NO: (203)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Aib-Gly-Gly-Pro-Ser-Ser-Gly-Ala-Pro-Pro-Pro-Ser-Lys-NH2

Example 201

SEQ ID NO: (204)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Asn-Thr-Gly-Pro-Ser-Ser-Gly-Ala-Pro-Pro-Pro-Ser-Lys-NH2

Example 202

SEQ ID NO: (205)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Arg-Gly-Gly-Pro-Ser-Ser-Gly-Ala-Pro-Pro-Pro-Ser-Lys-NH2

Example 203

SEQ ID NO: (206)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Arg-D-Ala-Gly-Pro-Ser-Ser-Gly-Ala-Pro-Pro-Pro-Ser-Lys-NH2

Example 204

SEQ ID NO: (207)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Lys-Gly-Gly-Pro-Ser-Ser-Gly-Ala-Pro-Pro-Pro-Ser-Lys-NH2

Example 205

SEQ ID NO: (208)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-Lys-NH2

Example 206

SEQ ID NO: (209)
H-His-Aib-Gln-Gly-Thr-Phe-Thr-Ser-Asp-Leu-Ser-Lys-Gln-Nle-Asp-Ser-Arg-Arg-Ala-Gln-Asp-Phe-Ile-Glu-Trp-Leu-Lys-Asn-Gly-Gly-Pro-Ser-Ser-Gly-Ala-Pro-Pro-Pro-Ser-NH2

Example 207

SEQ ID NO: (210)
H-His-D-Ser-Gln-Gly-Thr-Phe-Thr-Ser-Asp-Leu-Ser-Lys-Gln-Nle-Asp-Ser-Arg-Arg-Ala-Gln-Asp-Phe-Ile-Glu-Trp-Leu-Lys-Ala-Gly-Gly-Pro-Ser-Ser-Gly-Ala-Pro-Pro-Pro-Ser-NH2

Example 208

SEQ ID NO: (211)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Asn-Gly-Gly-Pro-Ser-Ser-Gly-Ala-Pro-Pro-Pro-Ser-NH2

Example 209

SEQ ID NO: (212)
H-His-Aib-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Asn-Gly-Gly-Pro-Ser-Ser-Gly-Ala-Pro-Pro-Pro-Ser-NH2

Example 210

SEQ ID NO: (213)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Ala-Gly-Gly-Pro-Ser-Ser-Gly-Ala-Pro-Pro-Pro-Ser-NH2

Example 211

SEQ ID NO: (214)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Asn-Ala-Gly-Pro-Ser-Ser-Gly-Ala-Pro-Pro-Pro-Ser-NH2

Example 212

SEQ ID NO: (215)
H-His-D-Ser-Gln-Gly-Thr-Phe-Thr-Ser-Asp-Leu-Ser-Lys-Gln-Nle-Asp-Ser-Arg-Arg-Ala-Gln-Asp-Phe-Ile-Glu-Trp-Leu-Lys-Ser-Gly-Gly-Pro-Ser-Ser-Gly-Ala-Pro-Pro-Pro-Ser-NH2

Example 213

SEQ ID NO: (216)
H-His-D-Ser-Gln-Gly-Thr-Phe-Thr-Ser-Asp-Leu-Ser-Lys-Gln-Nle-Asp-Ser-Arg-Arg-Ala-Gln-Asp-Phe-Ile-Glu-Trp-Leu-Lys-Lys-Gly-Gly-Pro-Ser-Ser-Gly-Ala-Pro-Pro-Pro-Ser-NH2

Example 214

SEQ ID NO: (217)
H-His-D-Ser-Gln-Gly-Thr-Phe-Thr-Ser-Asp-Leu-Ser-Lys-Gln-Nle-Asp-Ser-Arg-Arg-Ala-Gln-Asp-Phe-Ile-Glu-Trp-Leu-Lys-Asn-Ala-Gly-Pro-Ser-Ser-Gly-Ala-Pro-Pro-Pro-Ser-NH2

Example 215

SEQ ID NO: (218)
H-His-D-Ser-Gln-Gly-Thr-Phe-Thr-Ser-Asp-Leu-Ser-Lys-Gln-Nle-Asp-Ser-Arg-Arg-Ala-Gln-Asp-Phe-Ile-Glu-Trp-Leu-Lys-Asn-D-Ala-Gly-Pro-Ser-Ser-Gly-Ala-Pro-Pro-Pro-Ser-NH2

Example 216

SEQ ID NO: (219)
H-His-D-Ser-Gln-Gly-Thr-Phe-Thr-Ser-Asp-Leu-Ser-Lys-Gln-Nle-Asp-Lys-Arg-Arg-Ala-Gln-Asp-Phe-Ile-Glu-Trp-Leu-Lys-Asn-Gly-Gly-Pro-Ser-Ser-Gly-Ala-Pro-Pro-Pro-Ser-NH2

Example 217

SEQ ID NO: (220)
H-His-D-Ser-Gln-Gly-Thr-Phe-Thr-Ser-Asp-Leu-Ser-Lys-Gln-Nle-Asp-Glu-Arg-Arg-Ala-Lys-Asp-Phe-Ile-Glu-Trp-Leu-Lys-Asn-Gly-Gly-Pro-Ser-Ser-Gly-Ala-Pro-Pro-Pro-Ser-NH2

Example 218

SEQ ID NO: (221)
H-His-D-Ser-Gln-Gly-Thr-Phe-Thr-Ser-Asp-Leu-Ser-Lys-Gln-Nle-Asp-Ser-Arg-Arg-Ala-Gln-Asp-Phe-Ile-Glu-Trp-Leu-Lys-Asn-Thr-Gly-Pro-Ser-Ser-Gly-Ala-Pro-Pro-Pro-Ser-NH2

Example 219

SEQ ID NO: (222)
H-His-D-Ser-Gln-Gly-Thr-Phe-Thr-Ser-Asp-Leu-Ser-Lys-Gln-Nle-Asp-Ser-Arg-Arg-Ala-Gln-Asp-Phe-Ile-Glu-Trp-Leu-Lys-Aib-Gly-Gly-Pro-Ser-Ser-Gly-Ala-Pro-Pro-Pro-Ser-NH2

Example 220

SEQ ID NO: (223)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Aib-Gly-Gly-Pro-Ser-Ser-Gly-Ala-Pro-Pro-Pro-Ser-NH2

Example 221

SEQ ID NO: (224)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Asn-Thr-Gly-Pro-Ser-Ser-Gly-Ala-Pro-Pro-Pro-Ser-NH2

Example 222

SEQ ID NO: (225)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Arg-Gly-Gly-Pro-Ser-Ser-Gly-Ala-Pro-Pro-Pro-Ser-NH2

Example 223

SEQ ID NO: (226)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Arg-D-Ala-Gly-Pro-Ser-Ser-Gly-Ala-Pro-Pro-Pro-Ser-NH2

Example 224

SEQ ID NO: (227)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-Glu-Trp-Leu-Lys-Lys-Gly-Gly-Pro-Ser-Ser-Gly-Ala-Pro-Pro-Pro-Ser-NH2

Example 225

SEQ ID NO: (228)
H-His-D-Ser-Gln-Gly-Thr-Phe-Thr-Ser-Asp-Leu-Ser-Lys-Gln-Nle-Glu-Ser-Arg-Arg-Ala-Gln-Asp-Phe-Ile-

-continued

Glu-Trp-Leu-Lys-Ser-Gly-Gly-Pro-Ser-Ser-Gly-Ala-

Pro-Pro-Pro-Ser-NH2

Example 226

SEQ ID NO: (229)
H-His-D-Ser-Gln-Gly-Thr-Phe-Thr-Ser-Asp-Leu-Ser-

Lys-Gln-Met-Glu-Ser-Gln-Ala-Ala-Gln-Asp-Phe-Ile-

Glu-Trp-Leu-Lys-Ala-Gly-Gly-Pro-Ser-Ser-Gly-Ala-

Pro-Pro-Pro-Ser-NH2

Example 227

SEQ ID NO: (230)
H-His-D-Ser-Gln-Gly-Thr-Phe-Thr-Ser-Asp-Leu-Ser-

Lys-Gln-Nle-Glu-Ser-Gln-Ala-Ala-Gln-Asp-Phe-Ile-

Glu-Trp-Leu-Lys-Ala-Gly-Gly-Pro-Ser-Ser-Gly-Ala-

Pro-Pro-Pro-Ser-NH2

Example 228

SEQ ID NO: (231)
H-His-Aib-Gln-Gly-Thr-Phe-Thr-Ser-Asp-Leu-Ser-

Lys-Gln-Met-Glu-Ser-Gln-Ala-Ala-Gln-Asp-Phe-Ile-

Glu-Trp-Leu-Lys-Ala-Gly-Gly-Pro-Ser-Ser-Gly-Ala-

Pro-Pro-Pro-Ser-NH2

Example 229

SEQ ID NO: (232)
H-His-Aib-Gln-Gly-Thr-Phe-Thr-Ser-Asp-Leu-Ser-

Lys-Gln-Nle-Glu-Ser-Gln-Ala-Ala-Gln-Asp-Phe-Ile-

Glu-Trp-Leu-Lys-Ala-Gly-Gly-Pro-Ser-Ser-Gly-Ala-

Pro-Pro-Pro-Ser-NH2

Example 230

SEQ ID NO: (233)
H-His-D-Ser-Gln-Gly-Thr-Phe-Thr-Ser-Asp-Leu-Ser-

Lys-Gln-Met-Glu-Ser-Arg-Ala-Ala-Gln-Asp-Phe-Ile-

Glu-Trp-Leu-Lys-Ala-Gly-Gly-Pro-Ser-Ser-Gly-Ala-

Pro-Pro-Pro-Ser-NH2

Example 231

SEQ ID NO: (234)
H-His-D-Ser-Gln-Gly-Thr-Phe-Thr-Ser-Asp-Leu-Ser-

Lys-Gln-Nle-Glu-Ser-Arg-Ala-Ala-Gln-Asp-Phe-Ile-

Glu-Trp-Leu-Lys-Ala-Gly-Gly-Pro-Ser-Ser-Gly-Ala-

Pro-Pro-Pro-Ser-NH2

Example 232

SEQ ID NO: (235)
H-His-D-Ser-Gln-Gly-Thr-Phe-Thr-Ser-Asp-Leu-Ser-

Lys-Gln-Met-Glu-Ser-Lys-Ala-Ala-Gln-Asp-Phe-Ile-

Glu-Trp-Leu-Lys-Ala-Gly-Gly-Pro-Ser-Ser-Gly-Ala-

Pro-Pro-Pro-Ser-NH2

Example 233

SEQ ID NO: (236)
H-His-D-Ser-Gln-Gly-Thr-Phe-Thr-Ser-Asp-Leu-Ser-

Lys-Gln-Nle-Glu-Ser-Lys-Ala-Ala-Gln-Asp-Phe-Ile-

Glu-Trp-Leu-Lys-Ala-Gly-Gly-Pro-Ser-Ser-Gly-Ala-

Pro-Pro-Pro-Ser-NH2

Example 234

SEQ ID NO: (237)
H-His-Aib-Gln-Gly-Thr-Phe-Thr-Ser-Asp-Leu-Ser-

Lys-Gln-Met-Glu-Ser-Lys-Ala-Ala-Gln-Asp-Phe-Ile-

Glu-Trp-Leu-Lys-Ala-Gly-Gly-Pro-Ser-Ser-Gly-Ala-

Pro-Pro-Pro-Ser-NH2

Example 235

SEQ ID NO: (238)
H-His-Aib-Gln-Gly-Thr-Phe-Thr-Ser-Asp-Leu-Ser-

Lys-Gln-Nle-Glu-Ser-Lys-Ala-Ala-Gln-Asp-Phe-Ile-

Glu-Trp-Leu-Lys-Ala-Gly-Gly-Pro-Ser-Ser-Gly-Ala-

Pro-Pro-Pro-Ser-NH2

Example 236

Chemical Stability and Solubility

| SEQ ID NO | stability | | solubility [mg/ml] | |
| --- | --- | --- | --- | --- |
| | pH 4.5 | pH 7.4 | pH 4.5 | pH 7.4 |
| (7) | 99.4 | 86.7 | >1 | >1 |
| (60) | 99.0 | 97.8 | >1 | >1 |
| (63) | 99.9 | 87.7 | >1 | >1 |
| (70) | 99.1 | 90.9 | >1 | >1 |
| (75) | 98.3 | 84.9 | >1 | >1 |
| (76) | 98.9 | 88.6 | 0.952 | >1 |
| (77) | 97.6 | 89.9 | >1 | >1 |
| (78) | 99.9 | 88.6 | >1 | >1 |
| (79) | 98.8 | 99.0 | >1 | 0.666 |

Chemical stability of peptidic compounds was tested as described in Methods.

Example 237

In Vitro Data on GLP-1 and Glucagon Receptor

Potencies of peptidic compounds at the GLP-1 and glucagon receptors were determined by exposing cells expressing human glucagon receptor (hGlucagon R) and human GLP-1 receptor (hGLP-1 R) to the listed compounds at increasing concentrations and measuring the formed cAMP as described in Methods.

The results are shown in Table 1:

TABLE 1

EC50 values of exendin-4 peptide analogues at GLP-1 and Glucagon receptors (indicated in pM)

| SEQ ID NO | EC50 hGLP-1R | EC50 hGlucagonR |
| --- | --- | --- |
| (4) | 17.4 | 565000.0 |
| (9) | 22.2 | 26.4 |
| (10) | 31.3 | 16700.0 |
| (11) | 25.4 | 2320.0 |
| (12) | 1.2 | 794.0 |
| (13) | 3.2 | 410.0 |
| (14) | 5.8 | 419.0 |
| (5) | 16.6 | 67.0 |
| (15) | 35.2 | 538.0 |
| (16) | 7.6 | 2130.0 |
| (17) | 24.1 | 3360.0 |
| (18) | 1.1 | 2570.0 |
| (19) | 17.0 | 52.0 |
| (6) | 3.1 | 1.9 |
| (20) | 7.7 | 1.8 |
| (21) | 78.2 | 547.0 |
| (22) | 0.8 | 127.0 |
| (23) | 723.0 | 374.0 |
| (24) | 264.0 | 168.0 |
| (25) | 170.0 | 171.0 |
| (7) | 5.2 | 6.2 |
| (26) | 9.7 | 3.3 |
| (27) | 202.0 | 2280.0 |
| (28) | 128.0 | 6480.0 |
| (29) | 28.0 | 149.0 |
| (30) | 50.5 | 1050.0 |
| (31) | 10.9 | 132.0 |
| (32) | 75.7 | 262.0 |
| (33) | 138.0 | 347.0 |
| (34) | 102.0 | 590.0 |
| (35) | 89.4 | 43.0 |
| (8) | 20.3 | 35.1 |

TABLE 1-continued

EC50 values of exendin-4 peptide analogues at GLP-1 and Glucagon receptors (indicated in pM)

| SEQ ID NO | EC50 hGLP-1R | EC50 hGlucagonR |
| --- | --- | --- |
| (36) | 18.9 | 45.8 |
| (37) | 75.9 | 58.2 |
| (50) | 14.0 | 22.5 |
| (38) | 980.0 | 2810.0 |
| (39) | 4.6 | 683.0 |
| (40) | 8.1 | 1180.0 |
| (41) | 89.6 | 186.0 |
| (42) | 152.0 | 195.0 |
| (43) | 300.0 | 148.0 |
| (44) | 0.7 | 1120.0 |
| (45) | 0.8 | 103000.0 |
| (46) | 0.4 | 3520.0 |
| (47) | 0.8 | 1020.0 |
| (48) | 0.9 | 327.0 |
| (49) | 5.3 | 6880.0 |
| (51) | 5.8 | 6.3 |
| (52) | 4.1 | 24.1 |
| (53) | 0.2 | 317.0 |
| (54) | 0.6 | 2920.0 |
| (55) | 0.4 | 1020.0 |
| (56) | 1.8 | 2420.0 |
| (57) | 1.1 | 1080.0 |
| (58) | 0.9 | 413.0 |
| (59) | 2.9 | 40.9 |
| (60) | 3.5 | 4.8 |
| (61) | 4.2 | 30.4 |
| (62) | 6.3 | 130.0 |
| (63) | 9.9 | 58.0 |
| (64) | 21.9 | 67.0 |
| (65) | 15.0 | 5.7 |
| (66) | 13.0 | 16.2 |
| (67) | 21.5 | 7.7 |
| (68) | 12.3 | 7.8 |
| (69) | 7.6 | 5.9 |
| (70) | 5.0 | 17.2 |
| (71) | 5.6 | 1.9 |
| (72) | 5.2 | 2.9 |
| (73) | 4.4 | 21.2 |
| (74) | 39.6 | 35.5 |
| (75) | 4.6 | 64.1 |
| (76) | 4.8 | 74.1 |
| (77) | 3.0 | 37.2 |
| (78) | 4.2 | 18.1 |
| (79) | 3.7 | 195.0 |
| (80) | 10.8 | 38.1 |
| (81) | 19.7 | 29.3 |
| (82) | 2590.0 | 5520.0 |
| (83) | 369.0 | 375.0 |
| (84) | 3.9 | 13.8 |
| (85) | 6.4 | 9.0 |
| (86) | 28.1 | 21.8 |
| (87) | 5.7 | 19.1 |
| (88) | 5.1 | 18.2 |
| (89) | 5.9 | 19.8 |
| (90) | 4.9 | 33.6 |
| (91) | 6.7 | 121.0 |
| (92) | 6.0 | 38.0 |
| (93) | 188.0 | 1870.0 |
| (95) | 6.7 | 6.4 |
| (96) | 7.4 | 59.2 |
| (97) | 4.7 | 36.3 |
| (98) | 5.1 | 14.6 |
| (100) | 9.6 | 16.6 |
| (102) | 26.0 | 221.0 |
| (103) | 3.7 | 45.9 |
| (104) | 7.3 | 28.7 |
| (105) | 142.0 | 614.0 |
| (106) | 315.0 | 1320.0 |
| (107) | 9.0 | 5155.0 |
| (108) | 2.1 | 541.0 |
| (109) | 3.3 | 277.0 |
| (110) | 2.9 | 323.0 |

TABLE 1-continued

EC50 values of exendin-4 peptide analogues at GLP-1 and Glucagon receptors (indicated in pM)

| SEQ ID NO | EC50 hGLP-1R | EC50 hGlucagonR |
|---|---|---|
| (111) | 4.1 | 206.0 |
| (112) | 9.7 | 876.0 |
| (113) | 2.0 | 311.0 |
| (114) | 3.1 | 295.0 |
| (115) | 0.7 | 175.0 |
| (124) | 13.9 | 21.3 |
| (125) | 10.8 | 17.1 |

Example 238

Effect of Single Subcutaneous Administration of SEQ ID NO: 7 on Blood Glucose in Female Diet-Induced Obese (DIO) C57BL/6NCrl Mice (9 Months on High-Fat Diet)

Treatment with SEQ ID NO: 7 significantly decreased blood glucose over 24 h in obese DIO mice compared to vehicle-treated control animals (FIG. 1).

Example 239

Figure 2:
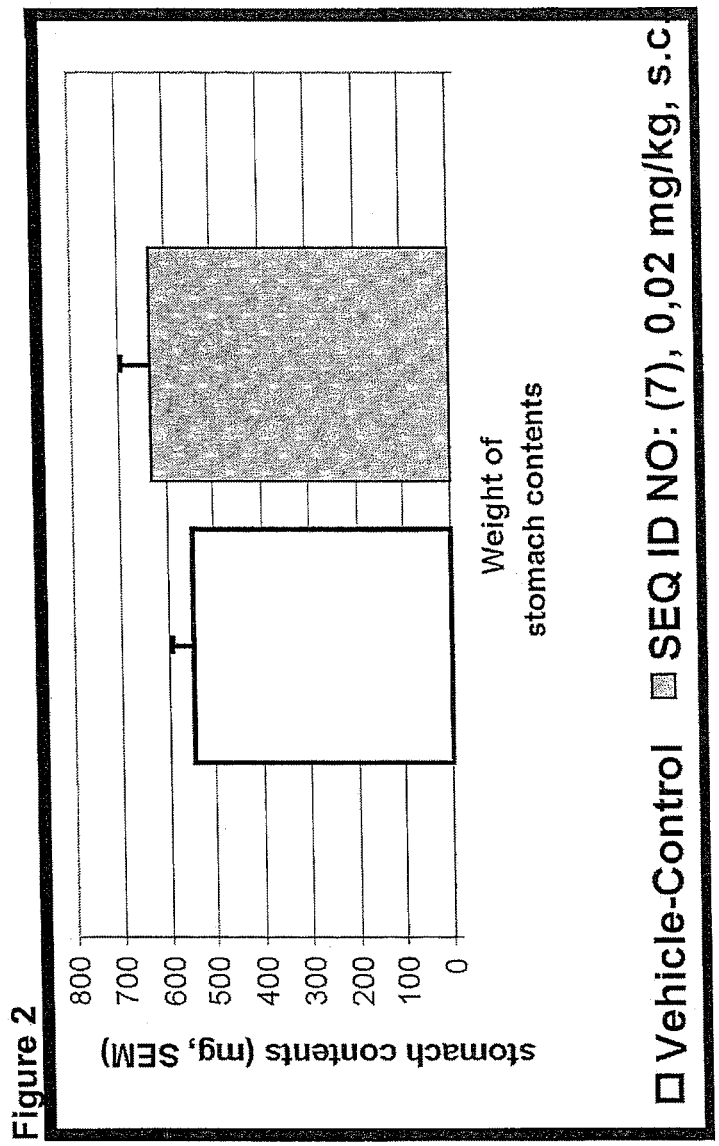
FIG. 2. Effect of s.c. administration of compound SEQ ID NO: (7) on gastric emptying in female NMRI-mice. Data are mean±SEM.
Figure 3:
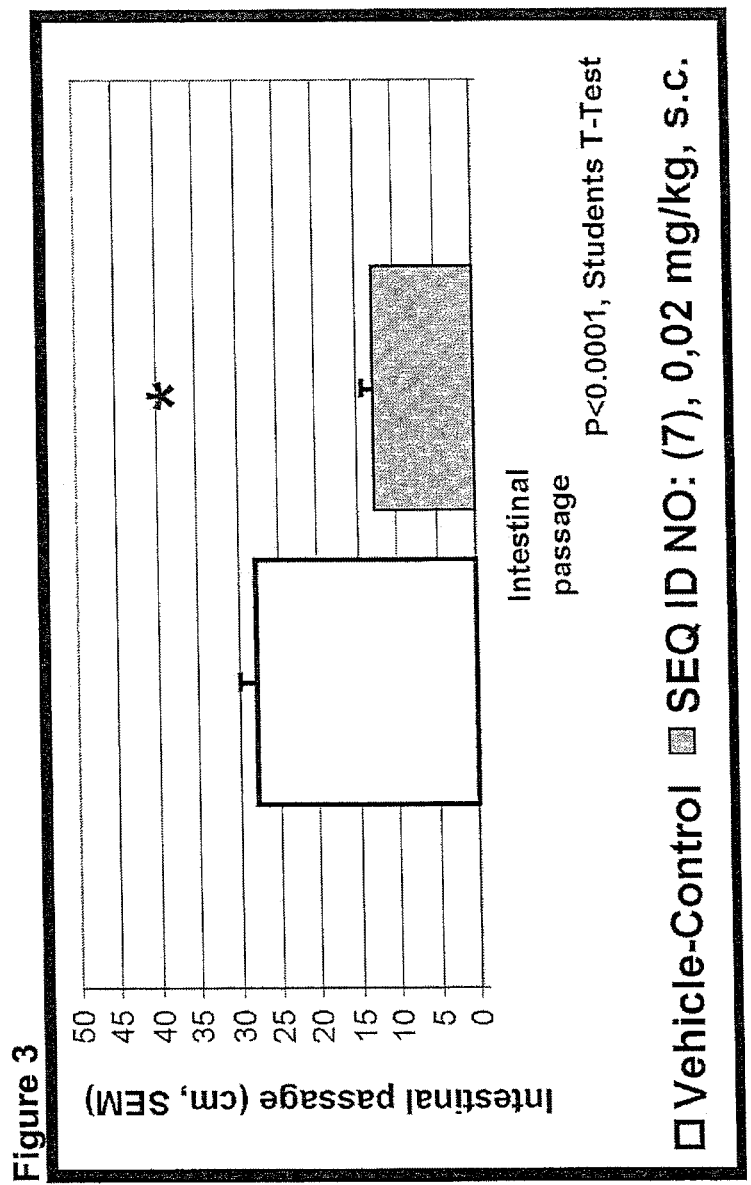
FIG. 3. Effect of s.c. administration of compound SEQ ID NO: (7) on intestinal motility in female NMRI-mice. Data are mean±SEM. $*p<0.0001$.

Effect of SEQ ID NO: 7 on Gastric Emptying and Intestinal Passage in Female NMRI-Mice Female NMRI-mice, weighing on average 25 g, received 0.02 mg/kg of the test compound SEQ ID NO: (7) or phosphate buffered saline (vehicle control) subcutaneously, 30 min prior to the administration of the coloured bolus. 30 min later, the assessment of stomach contents (FIG. 2) and intestinal passage (FIG. 3) was done.

At the tested dose, SEQ ID NO: (7) reduced intestinal passage by 54% (p<0.0001, Student's T-Test).

Example 240

Effect of SEQ ID NO: 7 on 22-Hours Food Intake in Female NMRI-Mice

Fed female NMRI-mice, weighing on average 27 g, were administered 0.01 or 0.1 mg/kg of SEQ ID NO: (7) or phosphate buffered saline (vehicle control) subcutaneously, directly prior to start of feeding monitoring. Lights-off phase (dark phase) started 4 hours later.

Figure 4:
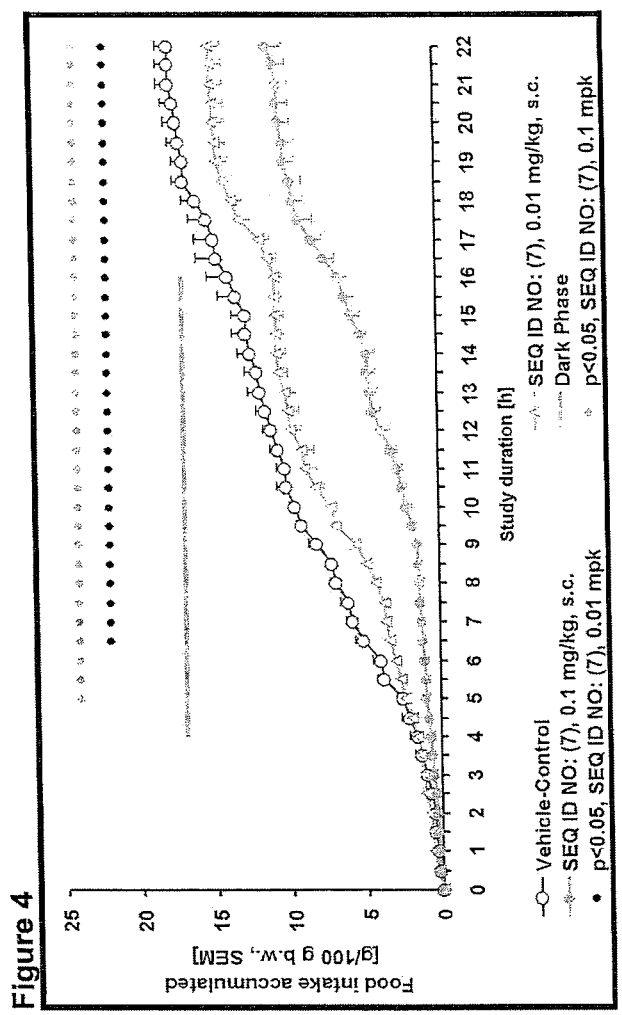
FIG. 4. Effect of s.c. administration of compound SEQ ID NO: (7) on 22-hours feed intake in female NMRI-mice. Data are mean±SEM. $*p<0.05$.

At the tested doses, SEQ ID NO: (7) demonstrated a dose-dependent reduction of feed intake, reaching 17% (p=0.0027) and 37% (p<0.0001, 2-W-ANOVA-RM, post hoc Dunnett's Test) at the end of the study, respectively (FIG. 4).

The invention claimed is:

1. A peptidic compound having formula (I):

R1-Z—R2      (I)

wherein Z is a peptide moiety having formula (II)

X0$_m$-X1-X2-X3-Gly-Thr-Phe-Thr-Ser-Asp-Leu-Ser-Lys-Gln-X14-X15-X16-X17-X18-X19-X20-X21-Phe-Ile-Glu-Trp-Leu-Lys-X28-X29-Gly-Pro-Ser-Ser-Gly-X35-Pro-Pro-Pro-X39-X40$_n$      (II)

X0 is absent or is Gly,

X1 is an amino acid residue selected from His, D-His, and Des-amino-His,

X2 is an amino acid residue selected from Gly, Ser, functionalized-Ser, D-Ser or functionalized D-Ser, Aib, Ala, or D-Ala, wherein functionalized Ser or functionalized D-Ser is functionalized in that the H of the OH side chain group is substituted by $C_{1-4}$ alkyl, X3 is an amino acid residue selected from Gln, His, and α-amino-functionalized Gln, wherein α-amino-functionalized Gln is functionalized in that an H of the α-NH$_2$ group is substituted by $C_{1-4}$ alkyl, X14 is an amino acid residue selected from Met, Phe, Aib, Nle, or functionalized Ala, wherein Ala is functionalized in that one hydrogen of the CH$_3$ side-chain group is substituted by $C_{3-8}$ cycloalkyl, X15 is an amino acid residue selected from Glu or Asp, X16 is an amino acid residue selected from Ser, Glu, or Lys, X17 is an amino acid residue selected from Arg, Glu, Gln, Aib, or Lys, X18 is an amino acid residue selected from Arg, Ala, or Lys, X19 is an amino acid residue selected from Ala or Val, X20 is an amino acid residue selected from Gln, Arg, Lys, His, or Aib, X21 is an amino acid residue selected from Asp, Leu, or Glu, X28 is an amino acid residue selected from Asn, Arg, Lys, Aib, Ser, Glu, or Ala, X29 is an amino acid residue selected from Gly, Ala, D-Ala, or Thr, X35 is an amino acid residue selected from Ala, Glu, Arg, or Lys, X39 is an amino acid residue selected from Ser, or an amino acid residue having a side chain with an —NH$_2$ group, wherein the —NH$_2$ side chain group is optionally modified or functionalized or an amino acid residue having a side chain with an —SH group, wherein the —SH side chain group is optionally modified or functionalized, and X40 is absent or is an amino acid residue selected from an amino acid residue having a side chain with an —NH$_2$ group, wherein the —NH$_2$ side chain group is optionally modified or functionalized or an amino acid residue having a side chain with an —SH group, wherein the —SH side chain group is optionally modified or functionalized, R1 is the N-terminal group of the peptidic compound and is selected from NH$_2$ or mono- or bisfunctionalized NH$_2$, wherein the mono- or bisfunctionalized NH$_2$ is functionalized at one or more H atom with (i) a moiety comprising up to 30 carbon atoms and optionally heteroatoms selected from F, Cl, Br, I, N, O, S, and/or P, or (ii) an organic polymer, wherein the organic polymer is optionally (CH$_2$—CH$_2$—O)q, wherein q is 1-2000

R2 is the C-terminal group of the peptidic compound and is selected from (i) OH or functionalized OH, or (ii) NH$_2$ or mono- or bisfunctionalized NH$_2$, wherein the functionalized OH or mono- or bisfunctionalized NH$_2$ is functionalized at one or more H atom with (i) a moiety comprising up to 40 carbon atoms and optionally heteroatoms selected from F, Cl, Br, I, N, O, S, and/or P, or (ii) an organic polymer, wherein the organic polymer is optionally of the formula R3-R4, wherein R3 is an organic polymer optionally comprising a (CH$_2$—CH$_2$—O)q, wherein q is 1-2000, and wherein R4 is selected from H, NH$_2$, NH(C1-4 alkyl), N(C1-C4 alkyl), N(C1-4 alkyl)2, OH, O(C1-4 alkyl), or SH, S(C1-4 alkyl), wherein m and n are in each case independently selected from 0 or 1, wherein when X39 or X40 or both comprise an amino acid residue having a side chain with a modified or functionalized —NH₂ group, the —NH₂ side chain group is modified or functionalized at its ε-amino group with —C(O)—R5, —S(O)₂—R5 or —R5, wherein R5 is
    (i) a moiety comprising up to 100 carbon atoms and optionally heteroatoms selected from N, O, S, and/or P, or
    (ii) an organic polymer, wherein the organic polymer optionally comprises polymers comprising a (CH₂—CH₂—O)q R6 group, wherein q is 1-2000 and R6 is H or C1-4 alkyl, or
wherein when X39 or X40 or both comprise an amino acid residue having a side chain with a modified or functionalized —SH group, the —SH side chain group is modified or functionalized at its H atom with
—Y—R7, wherein Y is a bond or a thiol linker group, and R7 is
    (i) a moiety comprising up to 100 carbon atoms and optionally heteroatoms selected from N, O, S, and/or P, or
    (ii) an organic polymer, wherein the organic polymer optionally comprises polymers comprising a (CH₂—CH₂—O)q R6 group, wherein q is 1-2000 and R6 is H or C1-4 alkyl,
or a salt or solvate thereof.

2. The compound, or salt or solvate thereof, of claim 1, wherein said functionalized Ser is Ser(OCH₃).

3. The compound, or salt or solvate thereof, of claim 1, wherein said functionalized D-Ser is D-Ser(OCH₃).

4. The compound, or salt or solvate thereof, of claim 1, wherein said C₁₋₄ alkyl is methyl.

5. The compound, or salt or solvate thereof, of claim 1, wherein said α-amino-functionalized Gln is Gln (NHCH₃).

6. The compound, or salt or solvate thereof, of claim 1, wherein said Cycloalkyl-Ala is Cyclohexyl (Chx)-Ala.

7. The compound, or salt or solvate thereof, of claim 1, wherein said amino acid residue having a side chain with an NH₂ group of X39 or X40 is Lys, Orn, Dab or Dap.

8. The compound, or salt or solvate thereof, of claim 1, wherein said amino acid residue having a side chain with an —SH group of X39 or X40 is Cys.

9. The compound, or salt or solvate thereof, of claim 1, wherein
    R1 is NH₂,
    R2 is NH₂, or
    R1 and R2 are NH₂.

10. The compound, or salt or solvate thereof, of claim 1, wherein
    m is 0 and X0 is absent.

11. The compound, or salt or solvate thereof, of claim 1, wherein
    n is 0 and X40 is absent.

12. The compound, or salt or solvate thereof, of claim 11, wherein X39 is Lys or functionalized Lys.

13. The compound, or salt or solvate thereof, of claim 1, wherein
    n is 1 and X40 is present.

14. The compound, or salt or solvate thereof, of claim 13, wherein X39 is Ser.

15. The compound, or salt or solvate thereof, of claim 13, wherein X40 is Lys or functionalized Lys.

16. The compound, or salt or solvate thereof, of claim 1, wherein X39 or X40 or both are functionalized Lys, and wherein
    the functionalized Lys is functionalized at its ε-amino group with
    —C(O)—R5, —S(O)₂—R5, or —R5
wherein —R5 is
    (i) a moiety comprising up to 100 carbon atoms and optionally heteroatoms selected from N, O, S and/or P, or
    (ii) an organic polymer.

17. The compound, or salt or solvate thereof, of claim 16, wherein —C(O)R5 is (S)-4-carboxy-4-hexadecanoyl-amino-butyryl, (S)-4-carboxy-4-octadecanoylamino-butyryl, hexadecanoyl or octadecanoyl.

18. The compound, or salt or solvate thereof, of claim 1, wherein X14 is Met or Nle.

19. The compound, or salt or solvate thereof, of claim 1, wherein
    X3 is Gln,
    X16 is Ser,
    X17 is Arg,
    X18 is Arg,
    X19 is Ala,
    X20 is Gln and
    X21 is Asp or Glu.

20. The compound, or salt or solvate thereof, of claim 1, wherein
    X2 is Ser, D-Ser or Aib.

21. The compound, or salt or solvate thereof, of claim 1, wherein
    (i) X2 is D-Ser or Aib and X40 is present and is functionalized Lys,
    (ii) X2 is Ser, D-Ser or Aib, X39 is functionalized Lys and X40 is absent,
    (iii) X2 is Ser, D-Ser or Aib and X40 is absent, or
    (iv) X2 is Ser, D-Ser or Aib and X40 is present and is functionalized Cys.

22. The compound, or salt or solvate thereof, of claim 1, wherein
    X15 is Glu.

23. The compound, or salt or solvate thereof, of claim 1, wherein
    X16 is Lys or Ser.

24. The compound, or salt or solvate thereof, of claim 1, wherein
    X19 is Ala.

25. The compound, or salt or solvate thereof, of claim 1, wherein
    X20 is Lys or Gln.

26. The compound, or salt or solvate thereof, of claim 1, wherein
   X21 is Leu or Glu.
27. The compound, or salt or solvate thereof, of claim 1, wherein
   X15 is Glu,
   X16 is Lys or Ser,
   X19 is Ala,
   X20 is Lys or Gln and
   X21 is Leu or Glu.
28. The compound, or salt or solvate thereof, of claim 1, wherein
   1, 2, 3, 4, 5 or 6 amino acid residues selected from X15, X16, X17, X18, X19, X20, or X21 are amino acid residues which differ from the corresponding amino acid residues in Exendin-4 (SEQ ID NO: 1); wherein X15 is Glu or Asp, X16 is Ser, Glu, or Lys, X17 is Arg, Glu, Gln, Aib, or Lys, X18 is Arg, Ala, or Lys, X19 is Ala or Val, X20 is Gln, Arg, Lys, His, or Aib, and X21 is Asp, Leu, or Glu.
29. The compound, or salt or solvate thereof, claim 1, wherein
   (a) X2 is D-Ser;
      X3 is Gln;
      X14 is Met;
      X15 is Asp or Glu;
      X16 is Ser;
      X17 is Arg;
      X18 is Arg or Ala;
      X19 is Ala;
      X20 is Gln or Arg;
      X21 is Asp or Leu;
      X28 is Asn, Ala, Ser, Lys, Aib, or Arg;
      X29 is Gly or D-Ala;
      X35 is Ala; and
      (i) X39 is Ser and
         X40 is present and is Lys, Orn, Dab, or Dap which are functionalized at the amino side chain group,
         or
      (ii) X39 is Lys which is functionalized at the amino side chain group, and
         n is 0 and X40 is absent,
   (b) X2 is D-Ser or Aib;
      X3 is Gln;
      X14 is Met;
      X15 is Asp or Glu;
      X16 is Ser, Glu, or Lys;
      X17 is Arg;
      X18 is Arg;
      X19 is Ala;
      X20 is Gln or Lys;
      X21 is Asp;
      X28 is Asn, Ser, Lys, or Aib;
      X29 is Gly, Thr, Ala, or D-Ala;
      X35 is Ala;
      X39 is Ser and
      (i) X40 is present and is Lys which is functionalized at the amino side chain group, or
      (ii) X39 is Lys which is functionalized at the amino side chain group, and
         n is 0 and X40 is absent,
   (c) X2 is D-Ser;
      X3 is Gln;
      X14 is Nle, Chx-Ala, Cp-Ala, or Cb-Ala;
      X15 is Asp or Glu;
      X16 is Ser;
      X17 is Arg;
      X18 is Arg or Ala;
      X19 is Ala;
      X20 is Gln or Lys;
      X21 is Asp, Glu, or Leu;
      X28 is Ala or Ser;
      X29 is Gly;
      X35 is Ala and
      (i) X39 is Ser and
         X40 is present and is Lys, Orn, Dab, or Dap which are functionalized at the amino side chain group, or
      (ii) X39 is Lys which is functionalized at the amino side chain group, and
         n is 0 and X40 is absent,
   (d) X2 is Ser or D-Ser;
      X3 is Gln;
      X14 is Met;
      X15 is Asp or Glu;
      X16 is Ser;
      X17 is Arg;
      X18 is Arg;
      X19 is Ala;
      X20 is Gln;
      X21 is Asp;
      X28 is Asn;
      X29 is Gly;
      X35 is Ala; and
      (i) X39 is Ser and
         X40 is present and is Lys which is functionalized at the amino side chain group, or
      (ii) X39 is Lys which is functionalized at the amino side chain group, and
         n is 0 and X40 is absent,
   (e) X2 is Ser or D-Ser;
      X3 is Gln;
      X14 is Met or Nle;
      X15 is Asp or Glu;
      X16 is Ser, Glu, or Lys;
      X17 is Arg or Glu;
      X18 is Arg or Ala;
      X19 is Ala;
      X20 is Gln, Arg, or Lys;
      X21 is Asp, Glu, or Leu;
      X28 is Asn;
      X29 is Gly;

X35 is Ala;
X39 is Ser and
n is 0 and X40 is absent, or
(f) X2 is Aib or D-Ser;
X3 is Gln;
X14 is Met or Nle;
X15 is Asp or Glu;
X16 is Ser, Glu, or Lys;
X17 is Arg, Lys, or Gln;
X18 is Arg or Ala;
X19 is Ala;
X20 is Gln or Lys;
X21 is Asp;
X28 is Asn, Ala, Aib, Lys, Arg, or Ser;
X29 is Gly, Ala, D-Ala, or Thr;
X35 is Ala;
X39 is Ser and
X40 is Lys or n is 0 and X40 is absent.

30. The compound, or salt or solvate thereof, of claim 29, wherein X40 or X39 is functionalized at the amino side chain group by (S)-4-carboxy-4-hexadecanoylamino-butyryl, (S)-4-carboxy-4-octadecanoylamino-butyryl, octadecanoyl, or hexadecanoyl.

31. The compound of claim 1, selected from the compounds of SEQ ID NOs: 7-238, or a salt or solvate thereof.

32. A pharmaceutical composition comprising the compound, or salt or solvate thereof, of claim 1, together with at least one pharmaceutically acceptable carrier.

33. The pharmaceutical composition of claim 32, further comprising at least one additional therapeutically active agent.

34. A method of treating type 2 diabetes or type 1 diabetes, comprising administering to a patient in need thereof a therapeutically effective amount of the pharmaceutical composition of claim 32.

35. A method for delaying disease progression in type 2 diabetes, progression from impaired glucose tolerance (IGT) to type 2 diabetes, or progression from type 2 diabetes to insulin-requiring diabetes comprising administering to a patient in need thereof a therapeutically effective amount of the pharmaceutical composition of claim 32.

36. A method for decreasing food intake, increasing energy expenditure, reducing body weight, regulating appetite, or inducing satiety comprising administering to a patient in need thereof a therapeutically effective amount of the pharmaceutical composition of claim 32.

37. The compound, or salt or solvate thereof, of claim 29, wherein X20 of (a) is Gln.

38. The composition, or salt or solvate thereof, of claim 33, wherein the additional therapeutically active agent is a GLP-1 compound, an insulinic compound, a gastrointestinal peptide or combinations thereof.

39. A compound, salt, or hydrate of claim 1.

40. A compound or salt of claim 1.

41. The compound, or salt or solvate thereof, of claim 1, wherein the compound is a dual GLP-1 and glucagon receptor agonist.

42. The compound, or salt or solvate thereof, of claim 1, wherein —C(O)—R5 is selected from the group consisting of:

(S)-4-carboxy-4-hexadecanoylamino-butyryl;
(S)-4-carboxy-4-octadecanoylamino-butyryl;
octadecanoyl;
hexadecanoyl;
(S)-4-carboxy-4-{3-[(R)-2,5,7,8-tetramethyl-2-((4R,8R)-4,8,12-trimethyl-tridecyl)-chroman-6-yloxycarbonyl]-propionylamino}-butyryl;
(S)-4-carboxy-4-(15-carboxy-pentadecanoylamino)-butyryl;
(S)-4-carboxy-4-((S)-4-carboxy-4-hexadecanoylamino-butyrylamino)-butyryl;
(S)-4-carboxy-4-octadecanoylamino-butyryl;
3-(3-hexadecanoylamino-propionylamino)-propionyl;
3-hexadecanoylamino-propionyl;
6-[(4,4-diphenyl-cyclohexyloxy)-hydroxy-phosphoryloxy]-hexanoyl;
(S)-4-carboxy-4-[(R)-4-((3R,5S,7R,8R,9R,10S,12S,13R,14R,17R)-3,7,12-trihydroxy-8,10,13-trimethyl-hexadecahydro-cyclopenta[a]phenanthren-17-yl)-pentanoylamino)-butyryl;
(S)-4-carboxy-4-[(R)-4-(3R,5R,8R,9S,10S,13R,14S,17R)-3-hydroxy-10,13-dimethyl-hexadecahydro-cyclopenta[a]phenanthren-17-yl)-pentanoylamino]-butyryl;
(S)-4-carboxy-4-(9S,10R)-9,10,16-trihydroxy-hexadecanoylamino)-butyryl;
(S)-4-carboxy-4-{3-[(R)-2,5,7,8-tetramethyl-2-((4R,8R)-4,8,12-trimethyl-tridecyl)-chroman-6-yloxycarbonyl]-propionylamino}-butyryl;
(S)-4-carboxy-4-(9Z,12Z)-octadeca-9,12-dienoylamino)-butyryl;
(S)-4-carboxy-4-(4-dodecyloxy-benzoylamino)-butyryl;
(S)-4-carboxy-4-henicosanoylamino-butyryl;
(S)-4-carboxy-4-docosanoylamino-butyryl;
(S)-4-carboxy-4-((Z)-nonadec-10-enoylamino)-butyryl;
(S)-4-carboxy-4-(4-decyloxy-benzoylamino)-butyryl;
(S)-4-carboxy-4-[(4'-octyloxy-biphenyl-4-carbonyl)-amino]-butyryl;
(S)-4-carboxy-4-(12-phenyl-dodecanoylamino)-butyryl;
acetyl;
4-hexadecanoylamino-butyryl;
(S)-4-carboxy-4-isobutyrylamino-butyryl;
(S)-4-carboxy-4-tetradecanoylamino-butyryl;
tetradecanoyl;
11-carboxy-undecanoyl;
11-benzyloxycarbonyl-undecanoyl;
(S)-4-carboxy-4-((S)-4-carboxy-4-tetradecanoylamino-butyrylamino)-butyryl;
(S)-4-carboxy-4-((S)-4-carboxy-4-octadecanoylamino-butyrylamino)-butyryl;

3-aminopropionyl;
3-(3-amino-propionylamino)-propionyl;
3-[3-(3-amino-propionylamino)-propionylamino]-propionyl;
3-{3-[3-(3-amino-propionylamino)-propionylamino]-propionylamino}-propionyl;
3-(3-{3-[(R)-2,5,7,8-tetramethyl-2-((4R,8R)-4,8,12-trimethyl-tridecyl)-chroman-6-yloxycarbonyl]-propionylamino}-propionylamino)-propionyl;
6-amino-hexanoyl;
6-(6-amino-hexanoylamino)-hexanoyl;
(2S,3R,4S,5R)-5-Carboxy-2,3,4,5-tetrahydroxy-pentanoyl;
8-amino-octanoyl;
3-{2-[2-(2-methoxy-ethoxy)-ethoxy]-ethoxy}-propionyl;
3-[2-(2-{2-[2-[2-(2-{2-[2-(2-{2-[2-(2-methoxy-ethoxy)-ethoxy]-ethoxy}-ethoxy)-ethoxy]-ethoxy}-ethoxy)-ethoxy}ethoxy)-ethoxy]-ethoxy]propionyl;
8-hexadecanoylamino-octanoyl;
6-[hydroxy-(naphthalen-2-yloxy)-phosphoryloxy]-hexanoyl;
6-[hydroxy-(5-phenyl-pentyloxy)-phosphoryloxy]-hexanoyl;
7-[4-(1-carboxy-ethyl)-phenylcarbamoyl]-heptanoyl;
4-(naphthalene-2-sulfonylamino)-4-oxo-butyryl;
4-(biphenyl-4-sulfonylamino)-4-oxo-butyryl;
(S)-4-carboxy-4-{(S)-4-carboxy-4-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-butyrylamino)-butyryl;
(S)-4-carboxy-4-[(2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-butyryl;
(S)-4-carboxy-2-{(S)-4-carboxy-2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-butyrylamino}-butyryl;
(S)-4-carboxy-2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-butyryl;
(S)-4-carboxy-4-{(S)-4-carboxy-4-[2-(2-{2-[(S)-4-carboxy-4-(17-carboxy-heptadecanoylamino)-butyrylamino]-ethoxy}-ethoxy)-acetylamino]-butyrylamino}-butyryl;
(S)-4-carboxy-4-[2-(2-{2-[(S)-4-carboxy-4-(17-carboxy-heptadecanoylamino)-butyrylamino]-ethoxy}-ethoxy)-acetylamino)-butyryl;
(S)-4-carboxy-2-{(S)-4-carboxy-2-[2-(2-{2-[(S)-4-carboxy-4-(17-carboxy-heptadecanoylamino)-butyrylamino]-ethoxy}-ethoxy)-acetylamino]-butyrylamino}-butyryl;
(S)-4-carboxy-2-[2-(2-{2-[(S)-4-carboxy-4-(17-carboxy-heptadecanoylamino)-butyrylamino]-ethoxy}-ethoxy)-acetylamino]-butyryl;
2-(2-{2-[2-(2-[2-[(S)-4-carboxy-4-(17-carboxy-heptadecanoylamino)-butyrylamino]-ethoxy}-ethoxy)-acetylamino]-ethoxy}-ethoxy)-acetyl;
2-(2-{2-[(S)-4-carboxy-4-(17-carboxy-heptadecanoylamino)-butyrylamino]-ethoxy}-ethoxy)-acetyl;
(S)-4-carboxy-4-((S)-4-carboxy-4-{(S)-4-carboxy-4-[(S)-4-carboxy-4-(19-carboxy-nonadecanoylamino)-butyrylamino]-butyrylamino}-butyrylamino)-butyryl;
2-(2-{2-[2-(2-{2-[(S)-4-carboxy-4-(16-1H-tetrazol-5-yl-hexadecanoylamino)-butyrylamino]-ethoxy}-ethoxy)-acetylamino]-ethoxy}-ethoxy)-acetyl;
2-(2-{2-[2-(2-{2-[(S)-4-carboxy-4-(16-carboxy-hexadecanoylamino)-butyrylamino]-ethoxy}-ethoxy)-acetylamino]-ethoxy}-ethoxy)-acetyl;
(S)-4-carboxy-4-{(S)-4-carboxy-4-[(S)-4-carboxy-4-(17-carboxy-heptadecanoylamino)-butyrylamino]-butyrylamino}-butyryl;
(S)-4-carboxy-4-((S)-4-carboxy-4-{2-[2-(2-{2-[2-(2-{(S)-4-carboxy-4-[10-(4-carboxy-phenoxy)-decanoylamino]-butyrylamino}-ethoxy)-ethoxy]-acetylamino}-ethoxy)-ethoxy]-acetylamino}-butyryl;
(S)-4-carboxy-4-((S)-4-carboxy-4-[2-(2-{2-[2-(2-{2-[(S)-4-carboxy-4-(7-carboxy-heptanoylamino)-butyrylamino]-ethoxy}-ethoxy)-acetylamino]-ethoxy}-ethoxy)-acetylamino]-butyrylamino}-butyryl;
(S)-4-carboxy-4-{(S)-4-carboxy-4-[2-(2-{2-[2-(2-{2-[(S)-4-carboxy-4-(11-carboxy-undecanoylamino)-butyrylamino]-ethoxy}-ethoxy)-acetylamino]-ethoxy}-ethoxy)-acetylamino]-butyrylamino}-butyryl;
(S)-4-carboxy-4-{(S)-4-carboxy-4-[2-(2-{2-[2-(2-{2-[(S)-4-carboxy-4-(13-carboxy-tridecanoylamino)-butyrylamino]-ethoxy}-ethoxy)-acetylamino]-ethoxy}-ethoxy)-acetylamino]-butyrylamino)-butyryl;
(S)-4-carboxy-4-{(S)-4-carboxy-4-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetylamino]-butyrylamino}-butyryl;
(S)-4-carboxy-4-≡(S)-4-carboxy-4-[2-(2-{2-[2-(2-{2-[(S)-4-carboxy-4-(19-carboxy-nonadecanoylamino)-butyrylamino]-ethoxyyethoxy)-acetylamino]-ethoxy}-ethoxy)-acetylamino]-butyrylamino}-butyryl; and
2-(2-[2-{2-(2-[2-{(3S,8S,9S,10R,13R,14S,17R)-10,13-dimethyl-17-((R)-1,5-dimethyl-hexyl)-2,3,4,7,8,9,10,11,12,13,14,15,16,17-tetradecahydro-1H-cyclopenta[a]phenanthren-3-yloxycarbonyl}-ethoxy]-ethoxy)-ethoxy}-ethoxy]-ethylcarbamoyl)-methyl.

43. The compound, or salt or solvate thereof, of claim 1, wherein R1 is selected from mono- or bisfunctionalized $NH_2$, wherein the mono- or bisfunctionalized $NH_2$ is functionalized at one or more H atom with a functional group selected from methyl, ethyl, formyl, acetyl, trifluoroacetyl, or benzoyl.

44. The compound, or salt or solvate thereof, of claim 1, wherein R2 is selected from
   (i) OH or functionalized OH, or
   (ii) $NH_2$ or mono- or bisfunctionalized $NH_2$, and wherein the functionalized OH or mono- or bisfunctionalized $NH_2$ is functionalized at one or more H atom with a functional group selected from 2-mercapto-ethyl, 2-tert-butyl sulfanyl-ethyl, 5-hydroxy-pentyl, 4-amino-butyl, 5-amino-pentyl, or 3-{2-[2-(5-amino-pentyloxy)-ethoxy]-ethoxy}-propyl.

* * * * *

```
SEQUENCE LISTING

<160> NUMBER OF SEQ ID NOS: 238

<210> SEQ ID NO 1
<211> LENGTH: 39
<212> TYPE: PRT
<213> ORGANISM: Heloderma suspectum
<220> FEATURE:
<221> NAME/KEY: MOD_RES
<222> LOCATION: 39
<223> OTHER INFORMATION: Ser is modified with an NH2 group

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 30
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 29
<212> TYPE: PRT
```

<213> ORGANISM: Homo sapiens

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 4
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 4

His Gly Glu Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Ser
        35

<210> SEQ ID NO 5
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 5

His Ser Gln Gly Thr Phe Thr Ser Asp Leu Ser Lys Gln Met Asp Glu
1               5                   10                  15

Arg Arg Ala Gln Asp Phe Ile Glu Trp Leu Lys Asn Gly Gly Pro Ser
            20                  25                  30

Ser Gly Ala Pro Pro Ser
        35

<210> SEQ ID NO 6
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Lys is functionalized at the amino side chain
      group as Lys(N-epsilon-(gamma-Glu(N-alfa-hexadecanoyl)))-NH2

<400> SEQUENCE: 6

His Ser Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Lys
        35

```
<210> SEQ ID NO 7
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 7

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40

<210> SEQ ID NO 8
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Serine is functionalized at the amino side
      chain group as Ser-NH-CH2-CH2-SH.

<400> SEQUENCE: 8

His Ser Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 9
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 9

His Ser Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 10
<211> LENGTH: 39
```

```
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Serine modified with an NH2.

<400> SEQUENCE: 10

His Ser Glu Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 11
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 11

His Gly Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 12
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 12

His Ser Gln Gly Thr Phe Thr Ser Asp Leu Ser Lys Gln Met Asp Ser
1               5                   10                  15

Arg Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 13
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 13
```

His Ser Gln Gly Thr Phe Thr Ser Asp Leu Ser Lys Gln Met Asp Ser
1               5                   10                  15

Arg Arg Val Arg Leu Phe Ile Glu Trp Leu Lys Asn Gly Gly Pro Ser
            20                  25                  30

Ser Gly Ala Pro Pro Pro Ser
        35

<210> SEQ ID NO 14
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 2
<223> OTHER INFORMATION: Xaa is an Aib amino acid
<220> FEATURE:
<221> NAME/KEY: MOD_RES
<222> LOCATION: 39
<223> OTHER INFORMATION: Ser is modified with an NH2 group

<400> SEQUENCE: 14

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 15
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 15

His Ser Gln Gly Thr Phe Thr Ser Asp Leu Ser Lys Gln Met Glu Glu
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 16
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 16

His Ser Gln Gly Thr Phe Thr Ser Asp Leu Ser Lys Gln Met Glu Glu
1               5                   10                  15

Arg Arg Ala Lys Asp Phe Ile Glu Trp Leu Lys Asn Gly Gly Pro Ser
            20                  25                  30

```
Ser Gly Ala Pro Pro Pro Ser
        35

<210> SEQ ID NO 17
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 17

His Ser Gln Gly Thr Phe Thr Ser Asp Leu Ser Lys Gln Met Glu Glu
1               5                   10                  15

Glu Arg Ala Lys Asp Phe Ile Glu Trp Leu Lys Asn Gly Gly Pro Ser
            20                  25                  30

Ser Gly Ala Pro Pro Pro Ser
        35

<210> SEQ ID NO 18
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 18

His Ser Gln Gly Thr Phe Thr Ser Asp Leu Ser Lys Gln Met Glu Glu
1               5                   10                  15

Glu Ala Ala Lys Leu Phe Ile Glu Trp Leu Lys Asn Gly Gly Pro Ser
            20                  25                  30

Ser Gly Ala Pro Pro Pro Ser
        35

<210> SEQ ID NO 19
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 19

His Ser Gln Gly Thr Phe Thr Ser Asp Leu Ser Lys Gln Met Asp Lys
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 20
<211> LENGTH: 39
<212> TYPE: PRT
<213> ORGANISM: Artificial Sequence
<220> FEATURE:
```

```
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Lys is functionalized at the amino side chain
      group as Lys(N-epsilon-(gamma-Glu(N-alfa-(omega-
      carboxypentadecanoyl))))-NH2

<400> SEQUENCE: 20

His Ser Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Lys
        35

<210> SEQ ID NO 21
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Lys is functionalized at the amino side chain
      group as Lys(N-epsilon-(hexadecanoyl))-NH2

<400> SEQUENCE: 21

His Ser Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Lys
        35

<210> SEQ ID NO 22
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 22

His Ser Gln Gly Thr Phe Thr Ser Asp Leu Ser Lys Gln Met Asp Ser
1               5                   10                  15

Arg Ala Ala Gln Leu Phe Ile Glu Trp Leu Lys Asn Gly Gly Pro Ser
            20                  25                  30

Ser Gly Ala Pro Pro Pro Ser
        35

<210> SEQ ID NO 23
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 1
<223> OTHER INFORMATION: Xaa is a D-His
<220> FEATURE:
<221> NAME/KEY: MOD_RES
```

```
<222> LOCATION: 39
<223> OTHER INFORMATION: Ser is modified with an NH2 group

<400> SEQUENCE: 23

Xaa Ser Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 24
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 24

His Ser Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 25
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: MOD_RES
<222> LOCATION: 3
<223> OTHER INFORMATION: Gln is an alpha-N-MeGln

<400> SEQUENCE: 25

His Ser Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 26
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
```

```
                    group as Lys(N-epsilon-(hexadecanoyl))-NH2

<400> SEQUENCE: 26

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40

<210> SEQ ID NO 27
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-(omega-
      carboxypentadecanoyl))))-NH2
<220> FEATURE:
<221> NAME/KEY: NON_STD
<222> LOCATION: 2
<223> OTHER INFORMATION: Xaa is a D-Ser

<400> SEQUENCE: 27

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40

<210> SEQ ID NO 28
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 2
<223> OTHER INFORMATION: Ser is a Ser(Me)
<220> FEATURE:
<221> NAME/KEY: MOD_RES
<222> LOCATION: 39
<223> OTHER INFORMATION: Ser is modified with an NH2 group

<400> SEQUENCE: 28

His Ser Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 29
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
```

```
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser

<400> SEQUENCE: 29

His Xaa Gln Gly Thr Phe Thr Ser Asp Leu Ser Lys Gln Met Asp Ser
1               5                   10                  15
Arg Arg Ala His Asp Phe Ile Glu Trp Leu Lys Asn Gly Gly Pro Ser
            20                  25                  30
Ser Gly Ala Pro Pro Pro Ser
        35

<210> SEQ ID NO 30
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Ser is modified with an NH2 group/

<400> SEQUENCE: 30

His Xaa Gln Gly Thr Phe Thr Ser Asp Leu Ser Lys Gln Met Asp Ser
1               5                   10                  15
Arg Arg Ala Lys Asp Phe Ile Glu Trp Leu Lys Asn Gly Gly Pro Ser
            20                  25                  30
Ser Gly Ala Pro Pro Pro Ser
        35

<210> SEQ ID NO 31
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Ser is modified with an NH2 group

<400> SEQUENCE: 31

His Xaa Gln Gly Thr Phe Thr Ser Asp Leu Ser Lys Gln Met Asp Ser
1               5                   10                  15
Arg Arg Ala Arg Asp Phe Ile Glu Trp Leu Lys Asn Gly Gly Pro Ser
            20                  25                  30
Ser Gly Ala Pro Pro Pro Ser
        35

<210> SEQ ID NO 32
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
```

```
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Ser is modified with an NH2 group

<400> SEQUENCE: 32

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Arg Gly Gly Pro Ser
            20                  25                  30

Ser Gly Ala Pro Pro Pro Ser
        35

<210> SEQ ID NO 33
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Ser is modified with an NH2 group

<400> SEQUENCE: 33

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Lys Gly Gly Pro Ser
            20                  25                  30

Ser Gly Glu Pro Pro Pro Ser
        35

<210> SEQ ID NO 34
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Ser is modified with an NH2 group

<400> SEQUENCE: 34

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Lys Gly Gly Pro Ser
            20                  25                  30

Ser Gly Glu Pro Pro Pro Ser
        35

<210> SEQ ID NO 35
<211> LENGTH: 39
<212> TYPE: PRT
<213> ORGANISM: Artificial Sequence
<220> FEATURE:
```

```
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Ser is modified with an NH2 group

<400> SEQUENCE: 35

His Xaa Gln Gly Thr Phe Thr Ser Asp Leu Ser Lys Gln Met Asp Ser
1               5                   10                  15

Arg Arg Ala Gln Leu Phe Ile Glu Trp Leu Lys Asn Gly Gly Pro Ser
            20                  25                  30

Ser Gly Ala Pro Pro Pro Ser
        35

<210> SEQ ID NO 36
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser modified as Ser-NH-CH2-CH2-S-tBu

<400> SEQUENCE: 36

His Ser Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 37
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Ser is modified with an NH2 group

<400> SEQUENCE: 37

His Xaa Gln Gly Thr Phe Thr Ser Asp Leu Ser Lys Gln Met Asp Ser
1               5                   10                  15

Arg Arg Ala Gln Glu Phe Ile Glu Trp Leu Lys Asn Gly Gly Pro Ser
            20                  25                  30

Ser Gly Ala Pro Pro Pro Ser
        35

<210> SEQ ID NO 38
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
```

```
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Aib amino acid
<220> FEATURE:
<221> NAME/KEY: MOD_RES
<222> LOCATION: 39
<223> OTHER INFORMATION: Ser is modified with an NH2 group

<400> SEQUENCE: 38

His Xaa Gln Gly Thr Phe Thr Ser Asp Leu Ser Lys Gln Xaa Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 39
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 39

His Ala Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 40
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ala
<220> FEATURE:
<221> NAME/KEY: MOD_RES
<222> LOCATION: 39
<223> OTHER INFORMATION: Ser is modified with an NH2 group

<400> SEQUENCE: 40

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 41
<211> LENGTH: 39
<212> TYPE: PRT
<213> ORGANISM: Artificial Sequence
<220> FEATURE:
```

-continued

```
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Ser is modified with an NH2 group

<400> SEQUENCE: 41

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 42
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: MOD_RES
<222> LOCATION: 28
<223> OTHER INFORMATION: Xaa is an Aib amino acid

<400> SEQUENCE: 42

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Xaa Gly Gly Pro Ser
            20                  25                  30

Ser Gly Ala Pro Pro Pro Ser
        35

<210> SEQ ID NO 43
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Ser is modified with an NH2 group

<400> SEQUENCE: 43

His Xaa Gln Gly Thr Phe Thr Ser Asp Leu Ser Lys Gln Phe Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35
```

```
<210> SEQ ID NO 44
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 44

His Ser Gln Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 45
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 45

His Gly Gln Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 46
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 46

His Ser Gln Gly Thr Phe Thr Ser Asp Leu Ser Lys Gln Met Asp Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 47
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
```

<223> OTHER INFORMATION: Ser is modified with an NH2 group

<400> SEQUENCE: 47

His Ser Gln Gly Thr Phe Thr Ser Asp Leu Ser Lys Gln Met Glu Ser
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 48
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 48

His Ser Gln Gly Thr Phe Thr Ser Asp Leu Ser Lys Gln Met Glu Glu
1               5                   10                  15

Arg Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 49
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 49

His Ser Gln Gly Thr Phe Thr Ser Asp Leu Ser Lys Gln Met Glu Glu
1               5                   10                  15

Glu Arg Val Arg Leu Phe Ile Glu Trp Leu Lys Asn Gly Gly Pro Ser
            20                  25                  30

Ser Gly Ala Pro Pro Pro Ser
        35

<210> SEQ ID NO 50
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser modified as Ser-NH-(CH2)5-OH

<400> SEQUENCE: 50

His Ser Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 51
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Lys is functionalized at the amino side chain
      group as Lys(N-epsilon-(gamma-Glu(N-alfa-hexadecanoyl)))-NH2

<400> SEQUENCE: 51

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Lys
        35

<210> SEQ ID NO 52
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Lys is functionalized at the amino side chain
      group as Lys(N-epsilon-(gamma-Glu(N-alfa-hexadecanoyl)))-NH2
<220> FEATURE:
<221> NAME/KEY: MOD_RES
<222> LOCATION: 2
<223> OTHER INFORMATION: Xaa is an Aib amino acid

<400> SEQUENCE: 52

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Lys
        35

<210> SEQ ID NO 53
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 53

His Ser Gln Gly Thr Phe Thr Ser Asp Leu Ser Lys Gln Met Glu Glu
1               5                   10                  15

Glu Ala Ala Arg Leu Phe Ile Glu Trp Leu Lys Asn Gly Gly Pro Ser
            20                  25                  30

Ser Gly Ala Pro Pro Ser
        35

<210> SEQ ID NO 54
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 54

His Ser Gln Gly Thr Phe Thr Ser Asp Leu Ser Lys Gln Met Glu Glu
1               5                   10                  15

Glu Ala Val Gln Leu Phe Ile Glu Trp Leu Lys Asn Gly Gly Pro Ser
            20                  25                  30

Ser Gly Ala Pro Pro Ser
        35

<210> SEQ ID NO 55
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 55

His Ser Gln Gly Thr Phe Thr Ser Asp Leu Ser Lys Gln Met Glu Glu
1               5                   10                  15

Glu Ala Val Arg Asp Phe Ile Glu Trp Leu Lys Asn Gly Gly Pro Ser
            20                  25                  30

Ser Gly Ala Pro Pro Ser
        35

<210> SEQ ID NO 56
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 56

His Ser Gln Gly Thr Phe Thr Ser Asp Leu Ser Lys Gln Met Glu Glu
1               5                   10                  15

Glu Ala Ala Gln Leu Phe Ile Glu Trp Leu Lys Asn Gly Gly Pro Ser
            20                  25                  30

Ser Gly Ala Pro Pro Ser
        35

<210> SEQ ID NO 57
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue

```
<220> FEATURE:
<221> NAME/KEY: MOD_RES
<222> LOCATION: 39
<223> OTHER INFORMATION: Ser is modified with an NH2 group

<400> SEQUENCE: 57

His Ser Gln Gly Thr Phe Thr Ser Asp Leu Ser Lys Gln Met Glu Glu
1               5                   10                  15

Glu Ala Ala Arg Asp Phe Ile Glu Trp Leu Lys Asn Gly Gly Pro Ser
            20                  25                  30

Ser Gly Ala Pro Pro Pro Ser
        35

<210> SEQ ID NO 58
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 58

His Ser Gln Gly Thr Phe Thr Ser Asp Leu Ser Lys Gln Met Glu Glu
1               5                   10                  15

Arg Ala Ala Arg Leu Phe Ile Glu Trp Leu Lys Asn Gly Gly Pro Ser
            20                  25                  30

Ser Gly Ala Pro Pro Pro Ser
        35

<210> SEQ ID NO 59
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 2
<223> OTHER INFORMATION: Xaa is an Aib amino acid.
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 59

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40

<210> SEQ ID NO 60
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
```

```
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 60

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser Lys
        35                  40

<210> SEQ ID NO 61
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 61

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40

<210> SEQ ID NO 62
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 2
<223> OTHER INFORMATION: Xaa is an Aib amino acid.
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 62

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40

<210> SEQ ID NO 63
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
```

```
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 63

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser Lys
        35                  40

<210> SEQ ID NO 64
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 64

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Asn Ala Gly Pro Ser
            20                  25                  30

Ser Gly Ala Pro Pro Pro Ser Lys
        35                  40

<210> SEQ ID NO 65
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 65

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 66
```

```
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 66

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Lys Gly Gly Pro Ser
            20                  25                  30

Ser Gly Ala Pro Pro Pro Ser Lys
        35                  40

<210> SEQ ID NO 67
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2/

<400> SEQUENCE: 67

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Ala Gly Pro Ser
            20                  25                  30

Ser Gly Ala Pro Pro Pro Ser Lys
        35                  40

<210> SEQ ID NO 68
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: NON_STD
<222> LOCATION: 29
<223> OTHER INFORMATION: Xaa is a D-Ala
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 68

His Xaa Gln Gly Thr Phe Thr Ser Asp Leu Ser Lys Gln Met Asp Ser
1               5                   10                  15
```

Arg Arg Ala Gln Asp Phe Ile Glu Trp Leu Lys Asn Xaa Gly Pro Ser
            20                  25                  30

Ser Gly Ala Pro Pro Pro Ser Lys
        35                  40

<210> SEQ ID NO 69
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 69

His Xaa Gln Gly Thr Phe Thr Ser Asp Leu Ser Lys Gln Met Asp Lys
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40

<210> SEQ ID NO 70
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 70

His Xaa Gln Gly Thr Phe Thr Ser Asp Leu Ser Lys Gln Met Asp Glu
1               5                   10                  15

Arg Arg Ala Lys Asp Phe Ile Glu Trp Leu Lys Asn Gly Gly Pro Ser
            20                  25                  30

Ser Gly Ala Pro Pro Pro Ser Lys
        35                  40

<210> SEQ ID NO 71
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 71

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Thr Gly Pro Ser
            20                  25                  30

Ser Gly Ala Pro Pro Pro Ser Lys
        35                  40

<210> SEQ ID NO 72
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 28
<223> OTHER INFORMATION: Xaa is an Aib amino acid
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 72

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Xaa Gly Gly Pro Ser
            20                  25                  30

Ser Gly Ala Pro Pro Pro Ser Lys
        35                  40

<210> SEQ ID NO 73
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2
<220> FEATURE:
<221> NAME/KEY: MOD_RES
<222> LOCATION: 28
<223> OTHER INFORMATION: Xaa is an Aib amino acid

<400> SEQUENCE: 73

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Xaa Gly Gly Pro Ser
            20                  25                  30

Ser Gly Ala Pro Pro Pro Ser Lys
        35                  40

<210> SEQ ID NO 74
<211> LENGTH: 40

```
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 74

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Asn Thr Gly Pro Ser
            20                  25                  30

Ser Gly Ala Pro Pro Pro Ser Lys
        35                  40

<210> SEQ ID NO 75
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 75

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Arg Gly Gly Pro Ser
            20                  25                  30

Ser Gly Ala Pro Pro Pro Ser Lys
        35                  40

<210> SEQ ID NO 76
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2
<220> FEATURE:
<221> NAME/KEY: NON_STD
<222> LOCATION: 29
<223> OTHER INFORMATION: Xaa is a D-Ala

<400> SEQUENCE: 76

His Xaa Gln Gly Thr Phe Thr Ser Asp Leu Ser Lys Gln Met Glu Ser
1               5                   10                  15
```

```
Arg Arg Ala Gln Asp Phe Ile Glu Trp Leu Lys Arg Xaa Gly Pro Ser
            20                  25                  30

Ser Gly Ala Pro Pro Pro Ser Lys
        35                  40

<210> SEQ ID NO 77
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 77

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Lys Gly Gly Pro Ser
            20                  25                  30

Ser Gly Ala Pro Pro Pro Ser Lys
        35                  40

<210> SEQ ID NO 78
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 78

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 79
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2
```

<400> SEQUENCE: 79

His Xaa Gln Gly Thr Phe Thr Ser Asp Leu Ser Lys Gln Met Glu Ser
1               5                   10                  15

Arg Ala Ala Gln Leu Phe Ile Glu Trp Leu Lys Ala Gly Gly Pro Ser
            20                  25                  30

Ser Gly Ala Pro Pro Pro Ser Lys
        35                  40

<210> SEQ ID NO 80
<211> LENGTH: 39
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 28
<223> OTHER INFORMATION: Xaa is an Aib amino acid
<220> FEATURE:
<221> NAME/KEY: MOD_RES
<222> LOCATION: 39
<223> OTHER INFORMATION: Lys is functionalized at the amino side chain
      group as Lys(N-epsilon-(gamma-Glu(N-alfa-hexadecanoyl)))-NH2

<400> SEQUENCE: 80

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Xaa Gly Gly Pro Ser
            20                  25                  30

Ser Gly Ala Pro Pro Pro Lys
        35

<210> SEQ ID NO 81
<211> LENGTH: 39
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Lys is functionalized at the amino side chain
      group as Lys(N-epsilon-(hexadecanoyl))-NH2
<220> FEATURE:
<221> NAME/KEY: MOD_RES
<222> LOCATION: 28
<223> OTHER INFORMATION: Xaa is an Aib amino acid

<400> SEQUENCE: 81

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Xaa Gly Gly Pro Ser
            20                  25                  30

Ser Gly Ala Pro Pro Pro Lys
        35

<210> SEQ ID NO 82
<211> LENGTH: 41
<212> TYPE: PRT

```
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 3
<223> OTHER INFORMATION: Xaa is a D-Ser
<220> FEATURE:
<221> NAME/KEY: MOD_RES
<222> LOCATION: 41
<223> OTHER INFORMATION: Lys is functionalized at the amino side chain
      group as Lys(N-epsilon-(gamma-Glu(N-alfa-hexadecanoyl)))-NH2

<400> SEQUENCE: 82

Gly His Xaa Gln Gly Thr Phe Thr Ser Asp Leu Ser Lys Gln Met Glu
1               5                   10                  15

Ser Arg Arg Ala Gln Asp Phe Ile Glu Trp Leu Lys Ser Gly Gly Pro
            20                  25                  30

Ser Ser Gly Ala Pro Pro Pro Ser Lys
        35                  40

<210> SEQ ID NO 83
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 1
<223> OTHER INFORMATION: His is alfa-N acylated
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 83

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 84
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-Octadecanoyl)))-NH2

<400> SEQUENCE: 84

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
```

```
                    20                  25                  30

Ser Gly Ala Pro Pro Ser Lys
        35                  40

<210> SEQ ID NO 85
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(Octadecanoyl))-NH2

<400> SEQUENCE: 85

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Ser Lys
        35                  40

<210> SEQ ID NO 86
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-tocopheryl-succinyl)))-NH2

<400> SEQUENCE: 86

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Ser Lys
        35                  40

<210> SEQ ID NO 87
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid
<220> FEATURE:
<221> NAME/KEY: MOD_RES
<222> LOCATION: 40
```

<223> OTHER INFORMATION: Lys is functionalized at the amino side chain
      group as Lys(N-epsilon-(gamma-Glu(N-alfa-hexadecanoyl)))-NH2

<400> SEQUENCE: 87

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser Lys
        35                  40

<210> SEQ ID NO 88
<211> LENGTH: 40
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Xaa is Orn(N-delta-(gamma-Glu(N-alfa-
      hexadecanoyl)))-NH2

<400> SEQUENCE: 88

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Xaa
        35                  40

<210> SEQ ID NO 89
<211> LENGTH: 40
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Xaa is Dab(N-gamma-(gamma-Glu(N-alfa-
      hexadecanoyl)))-NH2

<400> SEQUENCE: 89

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Xaa
        35                  40

<210> SEQ ID NO 90
<211> LENGTH: 40
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: NON_STD

```
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Xaa is Dap(N-beta-(gamma-Glu(N-alfa-
      hexadecanoyl)))-NH2

<400> SEQUENCE: 90

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Xaa
        35                  40

<210> SEQ ID NO 91
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 91

His Xaa Gln Gly Thr Phe Thr Ser Asp Leu Ser Lys Gln Met Glu Ser
1               5                   10                  15

Arg Arg Ala Arg Leu Phe Ile Glu Trp Leu Lys Ser Gly Gly Pro Ser
            20                  25                  30

Ser Gly Ala Pro Pro Pro Ser Lys
        35                  40

<210> SEQ ID NO 92
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 92

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Glu Gly Gly Pro Ser
            20                  25                  30

Ser Gly Arg Pro Pro Pro Ser Lys
        35                  40

<210> SEQ ID NO 93
<211> LENGTH: 40
<212> TYPE: PRT
```

```
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(gamma-Glu(N-alfa-aleuritolyl))-NH2

<400> SEQUENCE: 93

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 94
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys modified as Lys(N-alfa-aleuritolyl)-NH2

<400> SEQUENCE: 94

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 95
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Ala is a Cyclohexyl (Chx)-Ala
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 95

His Xaa Gln Gly Thr Phe Thr Ser Asp Leu Ser Lys Gln Ala Glu Ser
1               5                   10                  15

Arg Arg Ala Gln Asp Phe Ile Glu Trp Leu Lys Ala Gly Gly Pro Ser
            20                  25                  30
```

```
Ser Gly Ala Pro Pro Pro Ser Lys
        35                  40

<210> SEQ ID NO 96
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Ala is a Cyclopentyl-Ala
<220> FEATURE:
<221> NAME/KEY: MOD_RES
<222> LOCATION: 14
<223> OTHER INFORMATION: Lys is functionalized at the amino side chain
      group as Lys(N-epsilon-(gamma-Glu(N-alfa-hexadecanoyl)))-NH2

<400> SEQUENCE: 96

His Xaa Gln Gly Thr Phe Thr Ser Asp Leu Ser Lys Gln Ala Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser Lys
        35                  40

<210> SEQ ID NO 97
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-(gamma-Glu(N-alfa-
      hexadecanoyl))))-NH2

<400> SEQUENCE: 97

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 98
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
```

```
<223> OTHER INFORMATION: Lys is functionalized at the amino side chain
      group as Lys(N-epsilon-(beta-Ala(N-alfa-(beta-Ala(N-alfa-
      hexadecanoyl)))))-NH2

<400> SEQUENCE: 98

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 99
<211> LENGTH: 40
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-aminobutyroyl(N-gamma-
      hexadecanoyl)))-NH2
<220> FEATURE:
<221> NAME/KEY: NON_STD
<222> LOCATION: 2
<223> OTHER INFORMATION: Xaa is a D-Ser

<400> SEQUENCE: 99

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 100
<211> LENGTH: 39
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: NON_STD
<222> LOCATION: 39
<223> OTHER INFORMATION: Lys is functionalized at the amino side chain
      group as Lys(N-epsilon-(beta-Ala(N-alfa-(beta-Ala(N-alfa-
      hexadecanoyl)))))-NH2

<400> SEQUENCE: 100

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Lys
        35

<210> SEQ ID NO 101
<211> LENGTH: 39
<212> TYPE: PRT
<213> ORGANISM: Artificial Sequence
<220> FEATURE:
```

```
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Lys is functionalized at the amino side chain
      group as Lys(N-epsilon-(beta-Ala (N-alfa-hexadecanoyl)))-NH2

<400> SEQUENCE: 101

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Lys
        35

<210> SEQ ID NO 102
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 20
<223> OTHER INFORMATION: Xaa is an Aib amino acid
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 102

His Xaa Gln Gly Thr Phe Thr Ser Asp Leu Ser Lys Gln Met Glu Ser
1               5                   10                  15

Arg Arg Ala Xaa Asp Phe Ile Glu Trp Leu Lys Ser Gly Gly Pro Ser
            20                  25                  30

Ser Gly Ala Pro Pro Pro Ser Lys
        35                  40

<210> SEQ ID NO 103
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 103

His Xaa Gln Gly Thr Phe Thr Ser Asp Leu Ser Lys Gln Met Glu Ser
1               5                   10                  15

Arg Ala Ala Gln Asp Phe Ile Glu Trp Leu Lys Ser Gly Gly Pro Ser
            20                  25                  30
```

Ser Gly Ala Pro Pro Pro Ser Lys
        35                  40

<210> SEQ ID NO 104
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 104

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Glu Gly Gly Pro Ser
            20                  25                  30

Ser Gly Lys Pro Pro Pro Ser Lys
        35                  40

<210> SEQ ID NO 105
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-acetyl)-NH2

<400> SEQUENCE: 105

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 106
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-propionyl)))-NH2

<400> SEQUENCE: 106

His Xaa Gln Gly Thr Phe Thr Ser Asp Leu Ser Lys Gln Met Glu Ser

```
1               5                   10                  15
Arg Arg Ala Gln Asp Phe Ile Glu Trp Leu Lys Ser Gly Gly Pro Ser
            20                  25                  30

Ser Gly Ala Pro Pro Ser Lys
            35                  40
```

<210> SEQ ID NO 107
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(6-[(4,4-diphenyl-cyclohexyloxy)-hydroxy-
      phosphoryloxy]-hexanoyl)-NH2

<400> SEQUENCE: 107

```
His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Ser Lys
            35                  40
```

<210> SEQ ID NO 108
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 108

```
His Xaa Gln Gly Thr Phe Thr Ser Asp Leu Ser Lys Gln Met Glu Glu
1               5                   10                  15

Glu Ala Ala Gln Asp Phe Ile Glu Trp Leu Lys Ala Gly Gly Pro Ser
            20                  25                  30

Ser Gly Ala Pro Pro Ser Lys
            35                  40
```

<210> SEQ ID NO 109
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40

```
<223> OTHER INFORMATION: Lys is functionalized at the amino side chain
      group as Lys(N-epsilon-(gamma-Glu(N-alfa-hexadecanoyl)))-NH2

<400> SEQUENCE: 109

His Xaa Gln Gly Thr Phe Thr Ser Asp Leu Ser Lys Gln Met Glu Ser
1               5                   10                  15

Glu Ala Ala Gln Asp Phe Ile Glu Trp Leu Lys Ala Gly Gly Pro Ser
            20                  25                  30

Ser Gly Ala Pro Pro Pro Ser Lys
        35                  40

<210> SEQ ID NO 110
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 110

His Xaa Gln Gly Thr Phe Thr Ser Asp Leu Ser Lys Gln Met Glu Glu
1               5                   10                  15

Glu Ala Ala Lys Asp Phe Ile Glu Trp Leu Lys Ala Gly Gly Pro Ser
            20                  25                  30

Ser Gly Ala Pro Pro Pro Ser Lys
        35                  40

<210> SEQ ID NO 111
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2
<220> FEATURE:
<221> NAME/KEY: MOD_RES
<222> LOCATION: 17
<223> OTHER INFORMATION: Xaa is an Aib amino acid

<400> SEQUENCE: 111

His Xaa Gln Gly Thr Phe Thr Ser Asp Leu Ser Lys Gln Met Glu Ser
1               5                   10                  15

Xaa Ala Ala Gln Asp Phe Ile Glu Trp Leu Lys Ala Gly Gly Pro Ser
            20                  25                  30

Ser Gly Ala Pro Pro Pro Ser Lys
        35                  40

<210> SEQ ID NO 112
<211> LENGTH: 40
<212> TYPE: PRT
<213> ORGANISM: Artificial Sequence
```

-continued

```
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 17
<223> OTHER INFORMATION: Xaa is an Aib amino acid
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2/

<400> SEQUENCE: 112

His Xaa Gln Gly Thr Phe Thr Ser Asp Leu Ser Lys Gln Met Glu Ser
1               5                   10                  15

Xaa Ala Ala Gln Leu Phe Ile Glu Trp Leu Lys Ala Gly Gly Pro Ser
            20                  25                  30

Ser Gly Ala Pro Pro Pro Ser Lys
        35                  40

<210> SEQ ID NO 113
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 113

His Xaa Gln Gly Thr Phe Thr Ser Asp Leu Ser Lys Gln Met Glu Glu
1               5                   10                  15

Glu Ala Ala Lys Leu Phe Ile Glu Trp Leu Lys Ala Gly Gly Pro Ser
            20                  25                  30

Ser Gly Ala Pro Pro Pro Ser Lys
        35                  40

<210> SEQ ID NO 114
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 114

His Xaa Gln Gly Thr Phe Thr Ser Asp Leu Ser Lys Gln Met Glu Ser
1               5                   10                  15

Glu Ala Ala Gln Leu Phe Ile Glu Trp Leu Lys Ala Gly Gly Pro Ser
            20                  25                  30
```

Ser Gly Ala Pro Pro Pro Ser Lys
        35                  40

<210> SEQ ID NO 115
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 20
<223> OTHER INFORMATION: Xaa is an Aib amino acid
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 115

His Xaa Gln Gly Thr Phe Thr Ser Asp Leu Ser Lys Gln Met Glu Glu
1               5                   10                  15

Glu Ala Ala Xaa Asp Phe Ile Glu Trp Leu Lys Ala Gly Gly Pro Ser
            20                  25                  30

Ser Gly Ala Pro Pro Pro Ser Lys
        35                  40

<210> SEQ ID NO 116
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 3
<223> OTHER INFORMATION: Gln is an alpha N-Me-Gln
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 116

His Ser Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 117
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Lys is functionalized at the amino side chain group as Lys(N-epsilon-(gamma-Glu(N-alfa-octadecanoyl)))-NH2

<400> SEQUENCE: 117

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Lys
        35

<210> SEQ ID NO 118
<211> LENGTH: 39
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Lys(N-epsilon-(gamma-Glu(N-alfa-tocopheryl-
      succinyl)))-NH2

<400> SEQUENCE: 118

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Lys
        35

<210> SEQ ID NO 119
<211> LENGTH: 39
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Lys is functionalized at the amino side chain
      group as Lys(N-epsilon-(gamma-Glu(N-alfa-aleuritolyl)))-NH2

<400> SEQUENCE: 119

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Lys
        35

<210> SEQ ID NO 120
<211> LENGTH: 40
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: NON_STD
<222> LOCATION: 2

```
<223> OTHER INFORMATION: Xaa is a D-Ser
<220> FEATURE:
<221> NAME/KEY: MOD_RES
<222> LOCATION: 14
<223> OTHER INFORMATION: Ala is a Cyclobutyl-Ala
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2

<400> SEQUENCE: 120

His Xaa Gln Gly Thr Phe Thr Ser Asp Leu Ser Lys Gln Ala Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser Lys
        35                  40

<210> SEQ ID NO 121
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Lys is functionalized at the amino side chain
      group as Lys(N-epsilon-(gamma-Glu(N-alfa-(gamma-Glu(N-alfa-
      hexadecanoyl))))-NH2

<400> SEQUENCE: 121

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Lys
        35

<210> SEQ ID NO 122
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Ser is modified with an NH2 group

<400> SEQUENCE: 122

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35
```

```
<210> SEQ ID NO 123
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 20
<223> OTHER INFORMATION: Xaa is an Aib aminoacid
<220> FEATURE:
<221> NAME/KEY: MOD_RES
<222> LOCATION: 39
<223> OTHER INFORMATION: Ser is modified with an NH2 group

<400> SEQUENCE: 123

His Xaa Gln Gly Thr Phe Thr Ser Asp Leu Ser Lys Gln Met Glu Ser
1               5                   10                  15

Arg Arg Ala Xaa Asp Phe Ile Glu Trp Leu Lys Ala Gly Gly Pro Ser
            20                  25                  30

Ser Gly Ala Pro Pro Pro Ser
        35

<210> SEQ ID NO 124
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Lys is functionalized at the amino side chain
      group as Lys(N-epsilon-(gamma-aminobutyroyl(N-gamma-
      hexadecanoyl))-NH2

<400> SEQUENCE: 124

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Lys
        35

<210> SEQ ID NO 125
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-aminobutyroyl(N-gamma-
      hexadecanoyl))-NH2

<400> SEQUENCE: 125
```

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 126
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Lys is functionalized at the amino side chain
      group as Lys(N-epsilon-(gamma-Glu(N-alfa-cholyl)))-NH2

<400> SEQUENCE: 126

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Lys
        35

<210> SEQ ID NO 127
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Lys is functionalized at the amino side chain
      group as Lys(N-epsilon-(gamma-Glu(N-alfa-lithocholyl)))-NH2

<400> SEQUENCE: 127

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Lys
        35

<210> SEQ ID NO 128
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39

```
<223> OTHER INFORMATION: Lys is functionalized at the amino side chain
      group as Lys(N-epsilon-(gamma-Glu(N-alfa-linoleoyl)))-NH2

<400> SEQUENCE: 128

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Lys
        35

<210> SEQ ID NO 129
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Lys is functionalized at the amino side chain
      group as Lys(N-epsilon-(gamma-Glu(N-alfa-(4-dodecyclobenzoyl))))-NH2

<400> SEQUENCE: 129

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Lys
        35

<210> SEQ ID NO 130
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Lys is functionalized at the amino side chain
      group as Lys(N-epsilon-(gamma-Glu(N-alfa-heneicosanoyl)))-NH2

<400> SEQUENCE: 130

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Lys
        35

<210> SEQ ID NO 131
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
```

```
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Lys is functionalized at the amino side chain
      group as Lys(N-epsilon-(gamma-Glu(N-alfa-behenoyl)))-NH2

<400> SEQUENCE: 131

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Lys
        35

<210> SEQ ID NO 132
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Lys is functionalized at the amino side chain
      group as Lys(N-epsilon-(gamma-Glu(N-alfa-(cis-1-nonadecanoyl))))-
      NH2

<400> SEQUENCE: 132

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Lys
        35

<210> SEQ ID NO 133
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Lys is functionalized at the amino side chain
      group as Lys(N-epsilon-(gamma-Glu(N-alfa-(4-n-
      decycloxybenzoyl))))-NH2

<400> SEQUENCE: 133

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Lys
        35

<210> SEQ ID NO 134
```

```
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Lys is functionalized at the amino side chain
      group as Lys(N-epsilon-(gamma-Glu(N-alfa-(4'-octyloxy-biphenyl-4-
      carbonyl))))-NH2

<400> SEQUENCE: 134

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Lys
        35

<210> SEQ ID NO 135
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 39
<223> OTHER INFORMATION: Lys is functionalized at the amino side chain
      group as Lys(N-epsilon-(gamma-Glu(N-alfa-(12-phenyl-
      dodecanoyl))))-NH2

<400> SEQUENCE: 135

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Lys
        35

<210> SEQ ID NO 136
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-cholyl)))-NH2

<400> SEQUENCE: 136

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
```

```
                   20                  25                  30

Ser Gly Ala Pro Pro Pro Ser Lys
        35                  40

<210> SEQ ID NO 137
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-lithocholyl)))-NH2

<400> SEQUENCE: 137

His Xaa Gln Gly Thr Phe Thr Ser Asp Leu Ser Lys Gln Met Glu Ser
1               5                  10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 138
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-linoleoyl)))-NH2

<400> SEQUENCE: 138

His Xaa Gln Gly Thr Phe Thr Ser Asp Leu Ser Lys Gln Met Glu Ser
1               5                  10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 139
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-(4-dodecyclobenzoyl))))-NH2

<400> SEQUENCE: 139
```

-continued

```
His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 140
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-heneicosanoyl)))-NH2

<400> SEQUENCE: 140

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 141
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-behenoyl)))-NH2

<400> SEQUENCE: 141

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 142
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
```

```
<222> LOCATION: 40
<223> OTHER INFORMATION: Lys is functionalized at the amino side chain
      group as Lys(N-epsilon-(gamma-Glu(N-alfa-(cis-1-nonadecanoyl))))-
      NH2

<400> SEQUENCE: 142

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 143
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-(4-n-
      decycloxybenzoyl))))-NH2

<400> SEQUENCE: 143

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 144
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-(4'-octyloxy-biphenyl-4-
      carbonyl))))-NH2

<400> SEQUENCE: 144

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 145
<211> LENGTH: 40
<212> TYPE: PRT
<213> ORGANISM: Artificial Sequence
```

```
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-(12-phenyl-
      dodecanoyl))))-NH2

<400> SEQUENCE: 145

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 146
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(beta-Ala(N-alfa-hexadecanoyl)))-NH2

<400> SEQUENCE: 146

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 147
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group

<400> SEQUENCE: 147

His Ser Gln Gly Thr Phe Thr Ser Asp Leu Ser Lys Gln Met Asp Ser
1               5                   10                  15

Lys Lys Ala Gln Glu Phe Ile Glu Trp Leu Lys Asn Gly Gly Pro Ser
            20                  25                  30

Ser Gly Ala Pro Pro Pro Ser
        35

<210> SEQ ID NO 148
<211> LENGTH: 40
<212> TYPE: PRT
```

```
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Ser is modified with an NH2 group

<400> SEQUENCE: 148

Gly His Ser Gln Gly Thr Phe Thr Ser Asp Leu Ser Lys Gln Met Asp
1               5                   10                  15

Ser Arg Arg Ala Gln Asp Phe Ile Glu Trp Leu Lys Asn Gly Gly Pro
            20                  25                  30

Ser Ser Gly Ala Pro Pro Pro Ser
        35                  40

<210> SEQ ID NO 149
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is functionalized at the amino side chain
      group as Lys(N-epsilon-(PEG40kDa))-NH2
<220> FEATURE:
<221> NAME/KEY: NON_STD
<222> LOCATION: 2
<223> OTHER INFORMATION: Xaa is a D-Ser

<400> SEQUENCE: 149

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 150
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Cys is functionalized as Cys(PEG40kDa)-NH2
<220> FEATURE:
<221> NAME/KEY: NON_STD
<222> LOCATION: 2
<223> OTHER INFORMATION: Xaa is a D-Ser

<400> SEQUENCE: 150

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Cys
        35                  40

<210> SEQ ID NO 151
<211> LENGTH: 40
<212> TYPE: PRT
<213> ORGANISM: Artificial Sequence
```

```
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is functionalized at the amino side chain
      group as Lys(N-epsilon-(gamma-Glu(N-alfa-hexadecanoyl)))-NH2
<220> FEATURE:
<221> NAME/KEY: NON_STD
<222> LOCATION: 2
<223> OTHER INFORMATION: Xaa is a D-Ser

<400> SEQUENCE: 151

His Xaa Gln Gly Thr Phe Thr Ser Asp Leu Ser Lys Gln Met Glu Ser
1               5                   10                  15

Arg Arg Ala Gln Glu Phe Ile Glu Trp Leu Lys Ser Gly Gly Pro Ser
            20                  25                  30

Ser Gly Ala Pro Pro Pro Ser Lys
        35                  40

<210> SEQ ID NO 152
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 40
<223> OTHER INFORMATION: Lys is functionalized at the amino side chain
      group as Lys(N-epsilon-(hexadecanoyl))-NH2

<400> SEQUENCE: 152

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 153
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 2
<223> OTHER INFORMATION: Xaa is an Aib aminoacid
<220> FEATURE:
<221> NAME/KEY: MOD_RES
<222> LOCATION: 40
<223> OTHER INFORMATION: Lys is modified with an NH2 group

<400> SEQUENCE: 153

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40
```

```
<210> SEQ ID NO 154
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser

<400> SEQUENCE: 154

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser Lys
        35                  40

<210> SEQ ID NO 155
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser

<400> SEQUENCE: 155

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40

<210> SEQ ID NO 156
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: MOD_RES
<222> LOCATION: 2
<223> OTHER INFORMATION: Xaa is an Aib amino acid

<400> SEQUENCE: 156

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40
```

```
<210> SEQ ID NO 157
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser

<400> SEQUENCE: 157

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser Lys
        35                  40

<210> SEQ ID NO 158
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser

<400> SEQUENCE: 158

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Asn Ala Gly Pro Ser
            20                  25                  30

Ser Gly Ala Pro Pro Pro Ser Lys
        35                  40

<210> SEQ ID NO 159
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser

<400> SEQUENCE: 159

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Ser Gly Gly Pro Ser
            20                  25                  30
```

Ser Gly Ala Pro Pro Pro Ser Lys
        35                  40

<210> SEQ ID NO 160
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser

<400> SEQUENCE: 160

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Lys Gly Gly Pro Ser
            20                  25                  30

Ser Gly Ala Pro Pro Pro Ser Lys
        35                  40

<210> SEQ ID NO 161
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser

<400> SEQUENCE: 161

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Ala Gly Pro Ser
            20                  25                  30

Ser Gly Ala Pro Pro Pro Ser Lys
        35                  40

<210> SEQ ID NO 162
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: NON_STD
<222> LOCATION: 29
<223> OTHER INFORMATION: Xaa is a D-Ala

<400> SEQUENCE: 162

```
His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Xaa Gly Pro Ser
            20                  25                  30

Ser Gly Ala Pro Pro Pro Ser Lys
        35                  40

<210> SEQ ID NO 163
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser

<400> SEQUENCE: 163

His Xaa Gln Gly Thr Phe Thr Ser Asp Leu Ser Lys Gln Met Asp Lys
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40

<210> SEQ ID NO 164
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser

<400> SEQUENCE: 164

His Xaa Gln Gly Thr Phe Thr Ser Asp Leu Ser Lys Gln Met Asp Glu
1               5                   10                  15

Arg Arg Ala Lys Asp Phe Ile Glu Trp Leu Lys Asn Gly Gly Pro Ser
            20                  25                  30

Ser Gly Ala Pro Pro Pro Ser Lys
        35                  40

<210> SEQ ID NO 165
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
```

<400> SEQUENCE: 165

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Thr Gly Pro Ser
            20                  25                  30

Ser Gly Ala Pro Pro Pro Ser Lys
        35                  40

<210> SEQ ID NO 166
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 28
<223> OTHER INFORMATION: Xaa is an Aib amino acid

<400> SEQUENCE: 166

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Xaa Gly Gly Pro Ser
            20                  25                  30

Ser Gly Ala Pro Pro Pro Ser Lys
        35                  40

<210> SEQ ID NO 167
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 28
<223> OTHER INFORMATION: Xaa is an Aib amino acid

<400> SEQUENCE: 167

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Xaa Gly Gly Pro Ser
            20                  25                  30

Ser Gly Ala Pro Pro Pro Ser Lys
        35                  40

<210> SEQ ID NO 168
<211> LENGTH: 40
<212> TYPE: PRT
<213> ORGANISM: Artificial Sequence
<220> FEATURE:

<223> OTHER INFORMATION: Synthetic peptide, Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser

<400> SEQUENCE: 168

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Asn Thr Gly Pro Ser
            20                  25                  30

Ser Gly Ala Pro Pro Pro Ser Lys
        35                  40

<210> SEQ ID NO 169
<211> LENGTH: 40
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser

<400> SEQUENCE: 169

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Arg Gly Gly Pro Ser
            20                  25                  30

Ser Gly Ala Pro Pro Pro Ser Lys
        35                  40

<210> SEQ ID NO 170
<211> LENGTH: 40
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: NON_STD
<222> LOCATION: 29
<223> OTHER INFORMATION: Xaa is a D-Ala

<400> SEQUENCE: 170

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Arg Xaa Gly Pro Ser
            20                  25                  30

Ser Gly Ala Pro Pro Pro Ser Lys
        35                  40

```
<210> SEQ ID NO 171
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser

<400> SEQUENCE: 171

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Lys Gly Gly Pro Ser
            20                  25                  30

Ser Gly Ala Pro Pro Pro Ser Lys
        35                  40

<210> SEQ ID NO 172
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser

<400> SEQUENCE: 172

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 173
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser

<400> SEQUENCE: 173

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
```

```
<210> SEQ ID NO 174
<211> LENGTH: 39
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: MOD_RES
<222> LOCATION: 2
<223> OTHER INFORMATION: Xaa is an Aib amino acid

<400> SEQUENCE: 174

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 175
<211> LENGTH: 39
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser

<400> SEQUENCE: 175

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 176
<211> LENGTH: 39
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser

<400> SEQUENCE: 176

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Asn Ala Gly Pro Ser
            20                  25                  30
```

Ser Gly Ala Pro Pro Pro Ser
        35

<210> SEQ ID NO 177
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser

<400> SEQUENCE: 177

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser
        35

<210> SEQ ID NO 178
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser

<400> SEQUENCE: 178

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Ala Gly Pro Ser
            20                  25                  30

Ser Gly Ala Pro Pro Pro Ser
        35

<210> SEQ ID NO 179
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: NON_STD
<222> LOCATION: 29
<223> OTHER INFORMATION: Xaa is a D-Ala

<400> SEQUENCE: 179

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Xaa Gly Pro Ser
            20                  25                  30

Ser Gly Ala Pro Pro Pro Ser
        35

<210> SEQ ID NO 180
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser

<400> SEQUENCE: 180

His Xaa Gln Gly Thr Phe Thr Ser Asp Leu Ser Lys Gln Met Asp Lys
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 181
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser

<400> SEQUENCE: 181

His Xaa Gln Gly Thr Phe Thr Ser Asp Leu Ser Lys Gln Met Asp Glu
1               5                   10                  15

Arg Arg Ala Lys Asp Phe Ile Glu Trp Leu Lys Asn Gly Gly Pro Ser
            20                  25                  30

Ser Gly Ala Pro Pro Pro Ser
        35

<210> SEQ ID NO 182
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser

<400> SEQUENCE: 182

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Thr Gly Pro Ser
            20                  25                  30

Ser Gly Ala Pro Pro Pro Ser
        35

<210> SEQ ID NO 183
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 28
<223> OTHER INFORMATION: Xaa is an Aib amino acid

<400> SEQUENCE: 183

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Xaa Gly Gly Pro Ser
            20                  25                  30

Ser Gly Ala Pro Pro Pro Ser
        35

<210> SEQ ID NO 184
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser

<400> SEQUENCE: 184

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Asn Thr Gly Pro Ser
            20                  25                  30

Ser Gly Ala Pro Pro Pro Ser
        35

<210> SEQ ID NO 185
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES

```
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser

<400> SEQUENCE: 185

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Arg Gly Gly Pro Ser
            20                  25                  30

Ser Gly Ala Pro Pro Pro Ser
        35

<210> SEQ ID NO 186
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: NON_STD
<222> LOCATION: 29
<223> OTHER INFORMATION: Xaa is a D-Ala

<400> SEQUENCE: 186

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Arg Xaa Gly Pro Ser
            20                  25                  30

Ser Gly Ala Pro Pro Pro Ser
        35

<210> SEQ ID NO 187
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser

<400> SEQUENCE: 187

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Lys Gly Gly Pro Ser
            20                  25                  30

Ser Gly Ala Pro Pro Pro Ser
        35

<210> SEQ ID NO 188
<211> LENGTH: 39
```

```
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser

<400> SEQUENCE: 188

His Xaa Gln Gly Thr Phe Thr Ser Asp Leu Ser Lys Gln Met Glu Ser
 1               5                  10                  15

Arg Arg Ala Gln Asp Phe Ile Glu Trp Leu Lys Ser Gly Gly Pro Ser
            20                  25                  30

Ser Gly Ala Pro Pro Pro Ser
        35

<210> SEQ ID NO 189
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: MOD_RES
<222> LOCATION: 2
<223> OTHER INFORMATION: Xaa is an Aib amino acid
<220> FEATURE:
<221> NAME/KEY: MOD_RES
<222> LOCATION: 14
<223> OTHER INFORMATION: Xaa is an Nle amino acid

<400> SEQUENCE: 189

His Xaa Gln Gly Thr Phe Thr Ser Asp Leu Ser Lys Gln Xaa Asp Ser
 1               5                  10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40

<210> SEQ ID NO 190
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 190

His Xaa Gln Gly Thr Phe Thr Ser Asp Leu Ser Lys Gln Xaa Asp Ser
 1               5                  10                  15
```

Arg Arg Ala Gln Asp Phe Ile Glu Trp Leu Lys Ala Gly Gly Pro Ser
            20                  25                  30

Ser Gly Ala Pro Pro Pro Ser Lys
        35                  40

<210> SEQ ID NO 191
<211> LENGTH: 40
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 191

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40

<210> SEQ ID NO 192
<211> LENGTH: 40
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: MOD_RES
<222> LOCATION: 2
<223> OTHER INFORMATION: Xaa is an Aib amino acid
<220> FEATURE:
<221> NAME/KEY: MOD_RES
<222> LOCATION: 14
<223> OTHER INFORMATION: Xaa is an Nle amino acid

<400> SEQUENCE: 192

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40

<210> SEQ ID NO 193
<211> LENGTH: 40
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: MOD_RES
<222> LOCATION: 40

```
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 193

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser Lys
        35                  40

<210> SEQ ID NO 194
<211> LENGTH: 40
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 194

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Asn Ala Gly Pro Ser
            20                  25                  30

Ser Gly Ala Pro Pro Pro Ser Lys
        35                  40

<210> SEQ ID NO 195
<211> LENGTH: 40
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 195

His Xaa Gln Gly Thr Phe Thr Ser Asp Leu Ser Lys Gln Xaa Asp Ser
1               5                   10                  15

Arg Arg Ala Gln Asp Phe Ile Glu Trp Leu Lys Ser Gly Gly Pro Ser
            20                  25                  30
```

Ser Gly Ala Pro Pro Pro Ser Lys
        35                  40

<210> SEQ ID NO 196
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 196

His Xaa Gln Gly Thr Phe Thr Ser Asp Leu Ser Lys Gln Xaa Asp Ser
1               5                   10                  15

Arg Arg Ala Gln Asp Phe Ile Glu Trp Leu Lys Lys Gly Gly Pro Ser
            20                  25                  30

Ser Gly Ala Pro Pro Pro Ser Lys
        35                  40

<210> SEQ ID NO 197
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 197

His Xaa Gln Gly Thr Phe Thr Ser Asp Leu Ser Lys Gln Xaa Asp Ser
1               5                   10                  15

Arg Arg Ala Gln Asp Phe Ile Glu Trp Leu Lys Asn Ala Gly Pro Ser
            20                  25                  30

Ser Gly Ala Pro Pro Pro Ser Lys
        35                  40

<210> SEQ ID NO 198
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: NON_STD
<222> LOCATION: 29
<223> OTHER INFORMATION: Xaa is a D-Ala
<220> FEATURE:
<221> NAME/KEY: MOD_RES
<222> LOCATION: 14
<223> OTHER INFORMATION: Xaa is an Nle amino acid

<400> SEQUENCE: 198

His Xaa Gln Gly Thr Phe Thr Ser Asp Leu Ser Lys Gln Xaa Asp Ser
1               5                   10                  15

Arg Arg Ala Gln Asp Phe Ile Glu Trp Leu Lys Asn Xaa Gly Pro Ser
            20                  25                  30

Ser Gly Ala Pro Pro Pro Ser Lys
        35                  40

<210> SEQ ID NO 199
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 199

His Xaa Gln Gly Thr Phe Thr Ser Asp Leu Ser Lys Gln Xaa Asp Lys
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40

<210> SEQ ID NO 200
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 200

His Xaa Gln Gly Thr Phe Thr Ser Asp Leu Ser Lys Gln Xaa Asp Glu
1               5                   10                  15

Arg Arg Ala Lys Asp Phe Ile Glu Trp Leu Lys Asn Gly Gly Pro Ser

```
Ser Gly Ala Pro Pro Pro Ser Lys
        35                  40

<210> SEQ ID NO 201
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 201

His Xaa Gln Gly Thr Phe Thr Ser Asp Leu Ser Lys Gln Xaa Asp Ser
1               5                   10                  15

Arg Arg Ala Gln Asp Phe Ile Glu Trp Leu Lys Asn Thr Gly Pro Ser
            20                  25                  30

Ser Gly Ala Pro Pro Pro Ser Lys
        35                  40

<210> SEQ ID NO 202
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 28
<223> OTHER INFORMATION: Xaa is an Aib amino acid
<220> FEATURE:
<221> NAME/KEY: MOD_RES
<222> LOCATION: 14
<223> OTHER INFORMATION: Xaa is an Nle amino acid

<400> SEQUENCE: 202

His Xaa Gln Gly Thr Phe Thr Ser Asp Leu Ser Lys Gln Xaa Asp Ser
1               5                   10                  15

Arg Arg Ala Gln Asp Phe Ile Glu Trp Leu Lys Xaa Gly Gly Pro Ser
            20                  25                  30

Ser Gly Ala Pro Pro Pro Ser Lys
        35                  40

<210> SEQ ID NO 203
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
```

```
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 28
<223> OTHER INFORMATION: Xaa is an Aib amino acid
<220> FEATURE:
<221> NAME/KEY: MOD_RES
<222> LOCATION: 14
<223> OTHER INFORMATION: Xaa is an Nle amino acid

<400> SEQUENCE: 203

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Xaa Gly Gly Pro Ser
            20                  25                  30

Ser Gly Ala Pro Pro Pro Ser Lys
        35                  40

<210> SEQ ID NO 204
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 204

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Asn Thr Gly Pro Ser
            20                  25                  30

Ser Gly Ala Pro Pro Pro Ser Lys
        35                  40

<210> SEQ ID NO 205
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 205
```

```
His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Arg Gly Gly Pro Ser
            20                  25                  30

Ser Gly Ala Pro Pro Pro Ser Lys
        35                  40

<210> SEQ ID NO 206
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: NON_STD
<222> LOCATION: 29
<223> OTHER INFORMATION: Xaa is a D-Ala
<220> FEATURE:
<221> NAME/KEY: MOD_RES
<222> LOCATION: 14
<223> OTHER INFORMATION: Xaa is an Nle amino acid

<400> SEQUENCE: 206

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Arg Xaa Gly Pro Ser
            20                  25                  30

Ser Gly Ala Pro Pro Pro Ser Lys
        35                  40

<210> SEQ ID NO 207
<211> LENGTH: 40
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 207

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Lys Gly Gly Pro Ser
            20                  25                  30

Ser Gly Ala Pro Pro Pro Ser Lys
        35                  40

<210> SEQ ID NO 208
<211> LENGTH: 40
```

```
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 40
<223> OTHER INFORMATION: Lys is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 208

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser Lys
        35                  40

<210> SEQ ID NO 209
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: MOD_RES
<222> LOCATION: 2
<223> OTHER INFORMATION: Xaa is an Aib amino acid
<220> FEATURE:
<221> NAME/KEY: MOD_RES
<222> LOCATION: 14
<223> OTHER INFORMATION: Xaa is an Nle amino acid

<400> SEQUENCE: 209

His Xaa Gln Gly Thr Phe Thr Ser Asp Leu Ser Lys Gln Xaa Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 210
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid
```

<400> SEQUENCE: 210

His Xaa Gln Gly Thr Phe Thr Ser Asp Leu Ser Lys Gln Xaa Asp Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 211
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 211

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 212
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: MOD_RES
<222> LOCATION: 2
<223> OTHER INFORMATION: Xaa is an Aib amino acid
<220> FEATURE:
<221> NAME/KEY: MOD_RES
<222> LOCATION: 14
<223> OTHER INFORMATION: Xaa is an Nle amino acid

<400> SEQUENCE: 212

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 213
<211> LENGTH: 39
<212> TYPE: PRT
<213> ORGANISM: Artificial Sequence
<220> FEATURE:

<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 213

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 214
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 214

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Asn Ala Gly Pro Ser
            20                  25                  30

Ser Gly Ala Pro Pro Pro Ser
        35

<210> SEQ ID NO 215
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 215

His Xaa Gln Gly Thr Phe Thr Ser Asp Leu Ser Lys Gln Xaa Asp Ser

```
                1               5                  10                 15
Arg Arg Ala Gln Asp Phe Ile Glu Trp Leu Lys Ser Gly Gly Pro Ser
                20                 25                 30
Ser Gly Ala Pro Pro Ser
        35

<210> SEQ ID NO 216
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 216

His Xaa Gln Gly Thr Phe Thr Ser Asp Leu Ser Lys Gln Xaa Asp Ser
1               5                  10                 15
Arg Arg Ala Gln Asp Phe Ile Glu Trp Leu Lys Lys Gly Gly Pro Ser
                20                 25                 30
Ser Gly Ala Pro Pro Ser
        35

<210> SEQ ID NO 217
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 217

His Xaa Gln Gly Thr Phe Thr Ser Asp Leu Ser Lys Gln Xaa Asp Ser
1               5                  10                 15
Arg Arg Ala Gln Asp Phe Ile Glu Trp Leu Lys Asn Ala Gly Pro Ser
                20                 25                 30
Ser Gly Ala Pro Pro Ser
        35

<210> SEQ ID NO 218
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
```

```
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid
<220> FEATURE:
<221> NAME/KEY: NON_STD
<222> LOCATION: 29
<223> OTHER INFORMATION: Xaa is a D-Ala

<400> SEQUENCE: 218

His Xaa Gln Gly Thr Phe Thr Ser Asp Leu Ser Lys Gln Xaa Asp Ser
1               5                   10                  15

Arg Arg Ala Gln Asp Phe Ile Glu Trp Leu Lys Asn Xaa Gly Pro Ser
            20                  25                  30

Ser Gly Ala Pro Pro Pro Ser
        35

<210> SEQ ID NO 219
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 219

His Xaa Gln Gly Thr Phe Thr Ser Asp Leu Ser Lys Gln Xaa Asp Lys
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 220
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 220
```

-continued

```
His Xaa Gln Gly Thr Phe Thr Ser Asp Leu Ser Lys Gln Xaa Asp Glu
1               5                   10                  15

Arg Arg Ala Lys Asp Phe Ile Glu Trp Leu Lys Asn Gly Gly Pro Ser
            20                  25                  30

Ser Gly Ala Pro Pro Pro Ser
        35

<210> SEQ ID NO 221
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 221

His Xaa Gln Gly Thr Phe Thr Ser Asp Leu Ser Lys Gln Xaa Asp Ser
1               5                   10                  15

Arg Arg Ala Gln Asp Phe Ile Glu Trp Leu Lys Asn Thr Gly Pro Ser
            20                  25                  30

Ser Gly Ala Pro Pro Pro Ser
        35

<210> SEQ ID NO 222
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 28
<223> OTHER INFORMATION: Xaa is an Aib amino acid
<220> FEATURE:
<221> NAME/KEY: MOD_RES
<222> LOCATION: 14
<223> OTHER INFORMATION: Xaa is an Nle amino acid

<400> SEQUENCE: 222

His Xaa Gln Gly Thr Phe Thr Ser Asp Leu Ser Lys Gln Xaa Asp Ser
1               5                   10                  15

Arg Arg Ala Gln Asp Phe Ile Glu Trp Leu Lys Xaa Gly Gly Pro Ser
            20                  25                  30

Ser Gly Ala Pro Pro Pro Ser
        35

<210> SEQ ID NO 223
<211> LENGTH: 39
<212> TYPE: PRT
```

```
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 28
<223> OTHER INFORMATION: Xaa is an Aib amino acid
<220> FEATURE:
<221> NAME/KEY: MOD_RES
<222> LOCATION: 14
<223> OTHER INFORMATION: Xaa is an Nle amino acid

<400> SEQUENCE: 223

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Xaa Gly Gly Pro Ser
            20                  25                  30

Ser Gly Ala Pro Pro Pro Ser
        35

<210> SEQ ID NO 224
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 224

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Asn Thr Gly Pro Ser
            20                  25                  30

Ser Gly Ala Pro Pro Pro Ser
        35

<210> SEQ ID NO 225
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
```

<222> LOCATION: 14
<223> OTHER INFORMATION: Xaa is an Nle amino acid

<400> SEQUENCE: 225

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Arg Gly Gly Pro Ser
            20                  25                  30

Ser Gly Ala Pro Pro Pro Ser
        35

<210> SEQ ID NO 226
<211> LENGTH: 39
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: NON_STD
<222> LOCATION: 29
<223> OTHER INFORMATION: Xaa is a D-Ala
<220> FEATURE:
<221> NAME/KEY: MOD_RES
<222> LOCATION: 14
<223> OTHER INFORMATION: Xaa is an Nle amino acid

<400> SEQUENCE: 226

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Arg Xaa Gly Pro Ser
            20                  25                  30

Ser Gly Ala Pro Pro Pro Ser
        35

<210> SEQ ID NO 227
<211> LENGTH: 39
<212> TYPE: PRT
<213> ORGANISM: Artificial Sequence
<220> FEATURE:
<223> OTHER INFORMATION: Synthetic peptide, Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 227

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Lys Gly Gly Pro Ser
            20                  25                  30

Ser Gly Ala Pro Pro Pro Ser
        35

```
<210> SEQ ID NO 228
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 228

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser
        35

<210> SEQ ID NO 229
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser

<400> SEQUENCE: 229

His Xaa Gln Gly Thr Phe Thr Ser Asp Leu Ser Lys Gln Met Glu Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 230
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid
```

```
<400> SEQUENCE: 230

His Xaa Gln Gly Thr Phe Thr Ser Asp Leu Ser Lys Gln Xaa Glu Ser
1               5                   10                  15

Gln Ala Ala Gln Asp Phe Ile Glu Trp Leu Lys Ala Gly Gly Pro Ser
            20                  25                  30

Ser Gly Ala Pro Pro Ser
        35

<210> SEQ ID NO 231
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: MOD_RES
<222> LOCATION: 2
<223> OTHER INFORMATION: Xaa is an Aib amino acid

<400> SEQUENCE: 231

His Xaa Gln Gly Thr Phe Thr Ser Asp Leu Ser Lys Gln Met Glu Ser
1               5                   10                  15

Gln Ala Ala Gln Asp Phe Ile Glu Trp Leu Lys Ala Gly Gly Pro Ser
            20                  25                  30

Ser Gly Ala Pro Pro Ser
        35

<210> SEQ ID NO 232
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: MOD_RES
<222> LOCATION: 2
<223> OTHER INFORMATION: Xaa is an Aib amino acid
<220> FEATURE:
<221> NAME/KEY: MOD_RES
<222> LOCATION: 14
<223> OTHER INFORMATION: Xaa is an Nle amino acid

<400> SEQUENCE: 232

His Xaa Gln Gly Thr Phe Thr Ser Asp Leu Ser Lys Gln Xaa Glu Ser
1               5                   10                  15

Gln Ala Ala Gln Asp Phe Ile Glu Trp Leu Lys Ala Gly Gly Pro Ser
            20                  25                  30

Ser Gly Ala Pro Pro Ser
        35

<210> SEQ ID NO 233
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
```

```
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser

<400> SEQUENCE: 233

His Xaa Gln Gly Thr Phe Thr Ser Asp Leu Ser Lys Gln Met Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 234
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 234

His Xaa Gln Gly Thr Phe Thr Ser Asp Leu Ser Lys Gln Xaa Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 235
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser

<400> SEQUENCE: 235

His Xaa Gln Gly Thr Phe Thr Ser Asp Leu Ser Lys Gln Met Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 236
<211> LENGTH: 39
<212> TYPE: PRT
```

```
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: NON_STD
<222> LOCATION: 2
<223> OTHER INFORMATION: Xaa is a D-Ser
<220> FEATURE:
<221> NAME/KEY: MOD_RES
<222> LOCATION: 14
<223> OTHER INFORMATION: Xaa is an Nle amino acid

<400> SEQUENCE: 236

His Xaa Gln Gly Thr Phe Thr Ser Asp Leu Ser Lys Gln Xaa Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 237
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: MOD_RES
<222> LOCATION: 2
<223> OTHER INFORMATION: Xaa is an Aib amino acid

<400> SEQUENCE: 237

His Xaa Gln Gly Thr Phe Thr Ser Asp Leu Ser Lys Gln Met Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 238
<211> LENGTH: 39
<212> TYPE: PRT
<213> ORGANISM: Artificial Sequence
<220> FEATURE:
<223> OTHER INFORMATION: Synthetic peptide,Exendin-4 peptide analogue
<220> FEATURE:
<221> NAME/KEY: MOD_RES
<222> LOCATION: 39
<223> OTHER INFORMATION: Ser is modified with an NH2 group
<220> FEATURE:
<221> NAME/KEY: MOD_RES
<222> LOCATION: 2
<223> OTHER INFORMATION: Xaa is an Aib amino acid
<220> FEATURE:
<221> NAME/KEY: MOD_RES
<222> LOCATION: 14
<223> OTHER INFORMATION: Xaa is an Nle amino acid

<400> SEQUENCE: 238

His Xaa Gln Gly Thr Phe Thr Ser Asp Leu Ser Lys Gln Xaa Glu Ser
1               5                   10                  15
```

```
Lys Ala Ala Gln Asp Phe Ile Glu Trp Leu Lys Ala Gly Gly Pro Ser
            20                  25                  30

Ser Gly Ala Pro Pro Pro Ser
        35
```